(12) United States Patent
Thompson et al.

(10) Patent No.: US 8,021,379 B2
(45) Date of Patent: Sep. 20, 2011

(54) OBSTRUCTION REMOVAL SYSTEM

(75) Inventors: Dustin Thompson, Santa Rosa, CA (US); D.H. Perkins, Santa Rosa, CA (US); Jeeremy Johnson, San Francisco, CA (US); Michele Silver, Windsor, CA (US); Kevin Mauch, Windsor, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 379 days.

(21) Appl. No.: 11/972,743

(22) Filed: Jan. 11, 2008

(65) Prior Publication Data

US 2009/0182361 A1   Jul. 16, 2009

(51) Int. Cl.
*A61B 17/22* (2006.01)

(52) U.S. Cl. .......................... 606/159; 606/128; 606/170

(58) Field of Classification Search .......... 606/110–115, 606/127–128, 159, 161, 167, 170, 168, 171, 606/176, 177, 178, 180, 200; 604/266, 267
See application file for complete search history.

(56) References Cited

U.S. PATENT DOCUMENTS

| | | | |
|---|---|---|---|
| 1,374,638 A * | 4/1921 | De Cew et al. ................. 30/380 |
| 1,543,195 A * | 6/1925 | Thygesen et al. ............. 606/176 |
| 3,435,826 A | 4/1969 | Fogarty |
| 4,403,612 A | 9/1983 | Fogarty |
| 4,700,702 A * | 10/1987 | Nilsson .......................... 606/171 |
| 5,163,942 A * | 11/1992 | Rydell .......................... 606/113 |
| 5,197,918 A * | 3/1993 | Klaassen ....................... 452/171 |
| 5,584,843 A * | 12/1996 | Wulfman et al. ............. 606/159 |
| 5,725,530 A * | 3/1998 | Popken ............................ 606/82 |
| 6,663,650 B2 | 12/2003 | Sepetka et al. |
| 6,702,782 B2 | 3/2004 | Miller et al. |
| 6,730,104 B1 | 5/2004 | Sepetka et al. |
| 7,285,126 B2 | 10/2007 | Sepetka et al. |
| 7,534,252 B2 * | 5/2009 | Sepetka et al. ................ 606/200 |
| 2002/0123698 A1 * | 9/2002 | Garibotto et al. ............. 600/585 |
| 2005/0228417 A1 * | 10/2005 | Teitelbaum et al. .......... 606/159 |
| 2006/0095059 A1 * | 5/2006 | Bleich et al. .................. 606/170 |
| 2006/0195137 A1 | 8/2006 | Sepetka et al. |
| 2006/0282065 A1 | 12/2006 | Cohen |
| 2007/0100361 A1 * | 5/2007 | Cohen .......................... 606/167 |
| 2008/0234690 A1 | 9/2008 | Hawkins et al. |
| 2009/0112238 A1 * | 4/2009 | Pitts et al. ..................... 606/159 |

* cited by examiner

Primary Examiner — S. Thomas Hughes
Assistant Examiner — David Eastwood

(57) ABSTRACT

An obstruction removal system for percutaneous removal of clots or obstructions within the vascular system is disclosed. The obstruction removal system includes a multi-lumen catheter with a plurality of circulating capture devices occurring along a drive belt. The plurality of capture devices may be basket-like devices attached to the drive belt, or may be formed by integral coiled or protuberant sections of the drive belt. The circulating capture or interference devices affect removal of the clot or obstruction bit-by-bit through a series of passes.

16 Claims, 38 Drawing Sheets

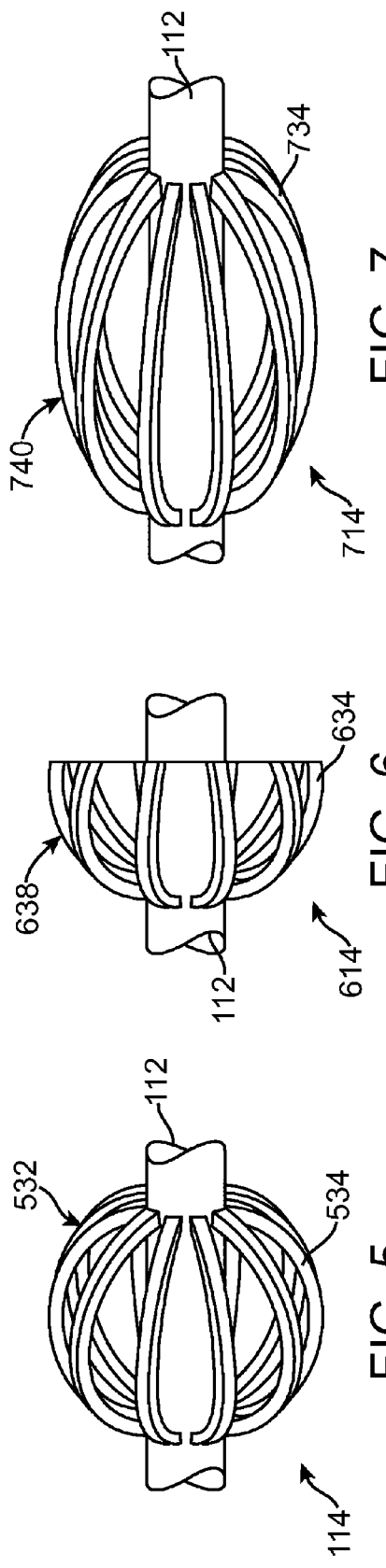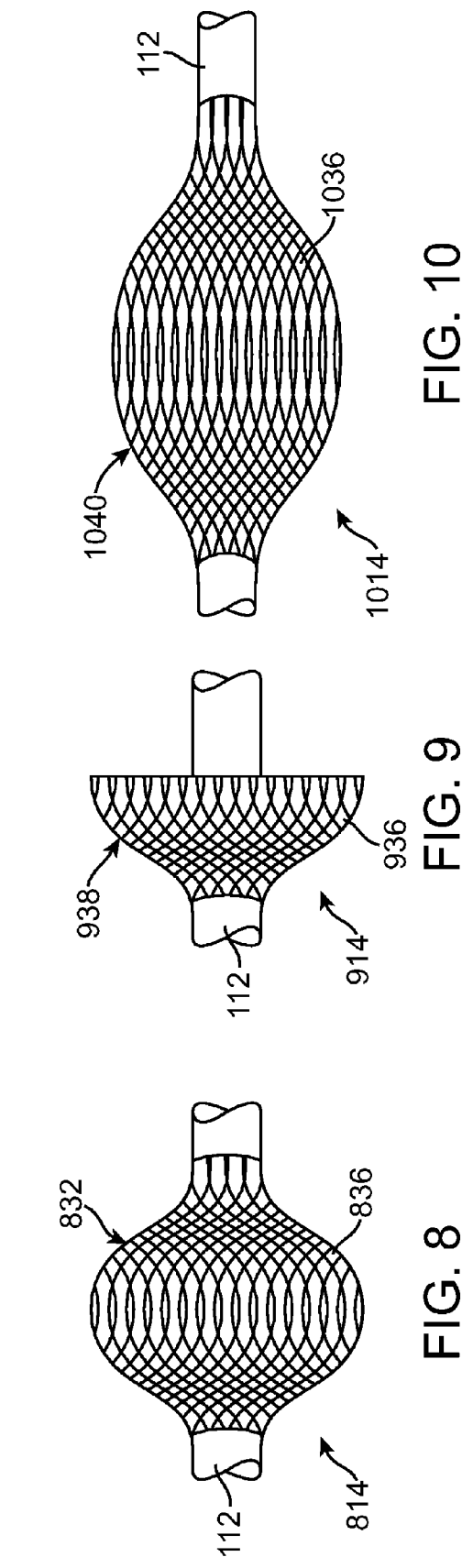

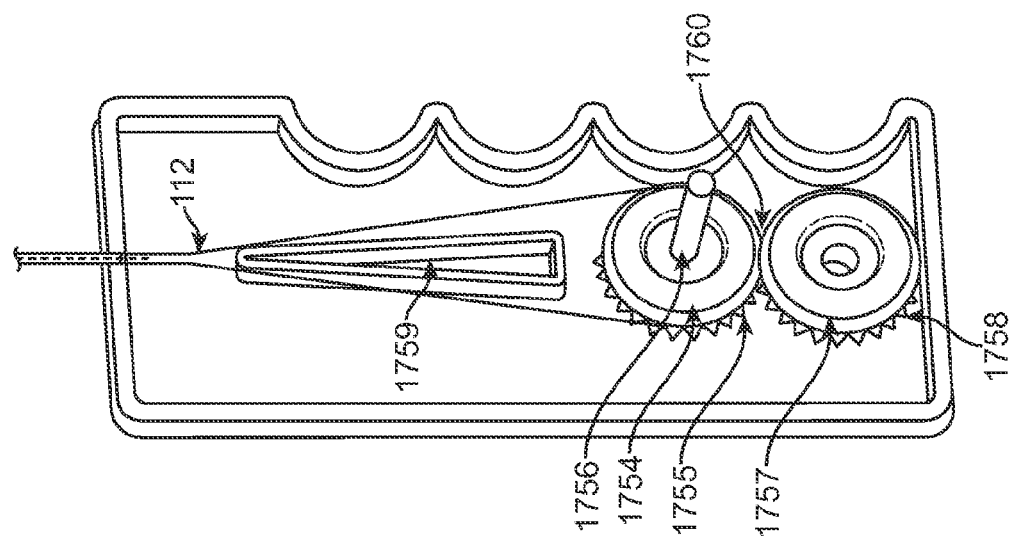
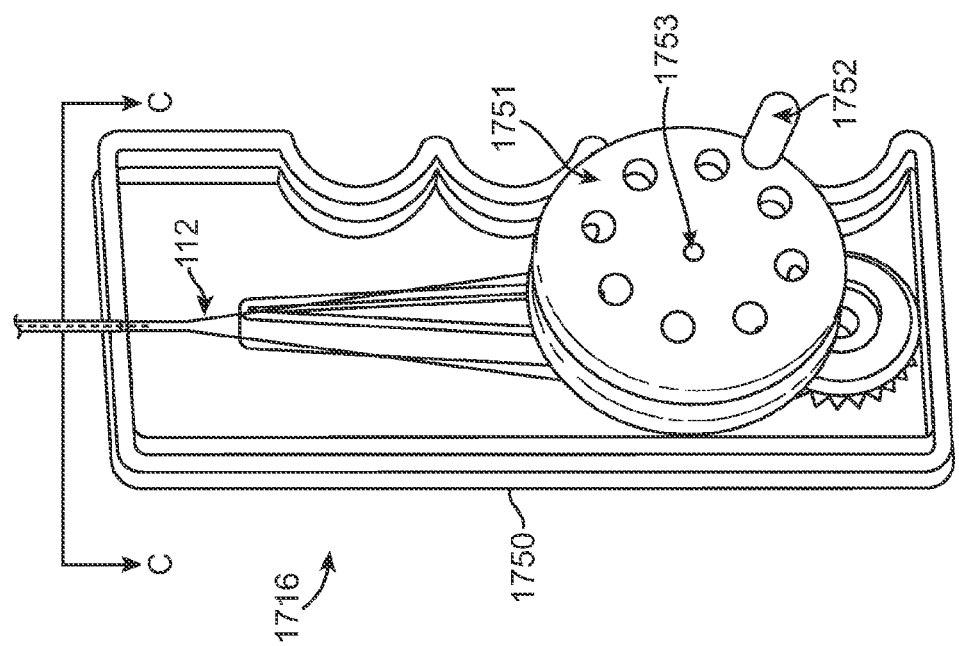
FIG. 17A
FIG. 17B

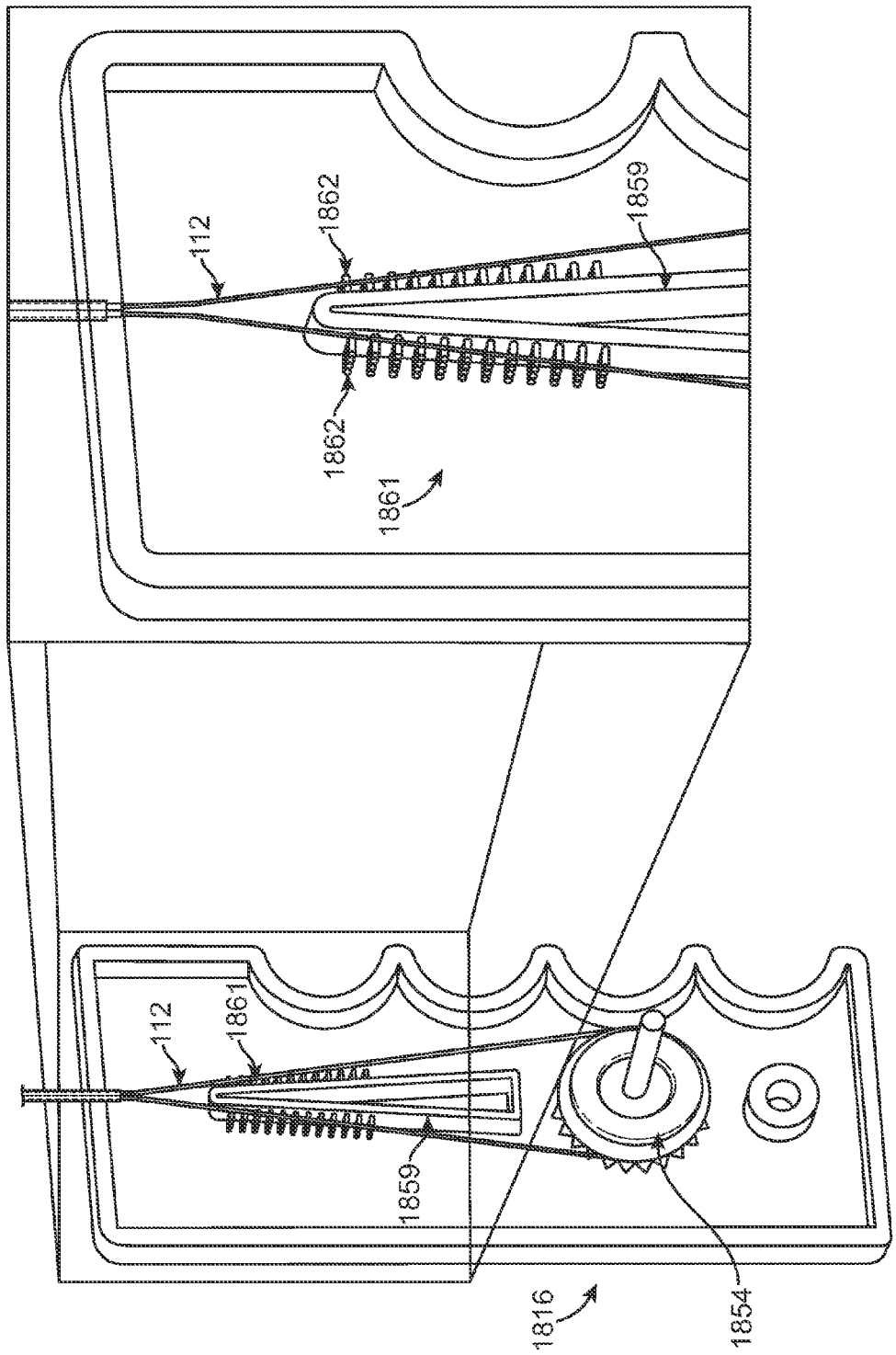

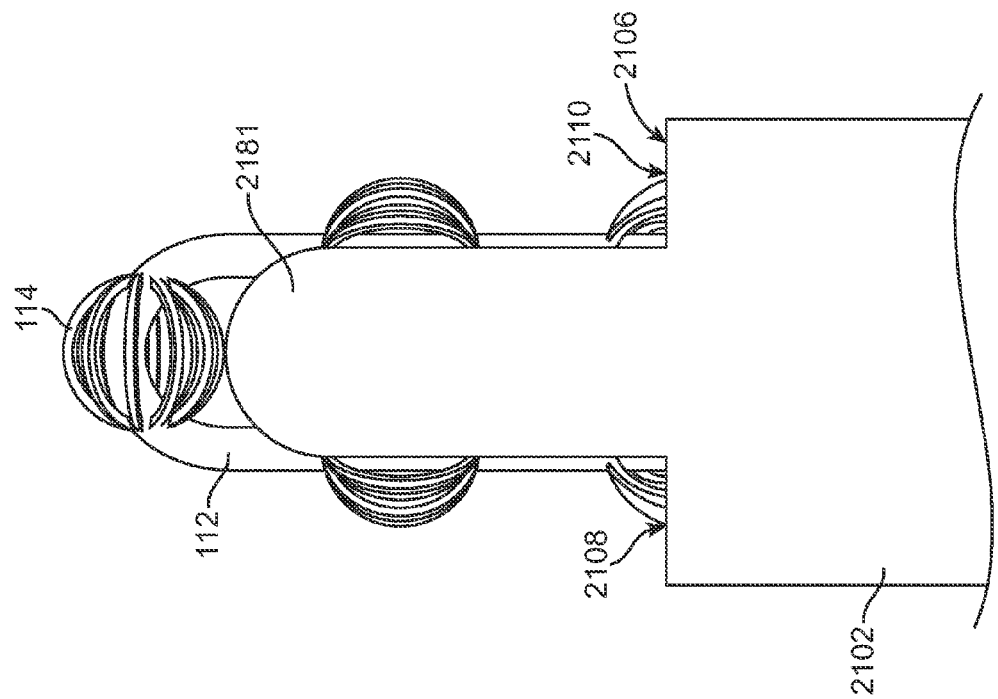
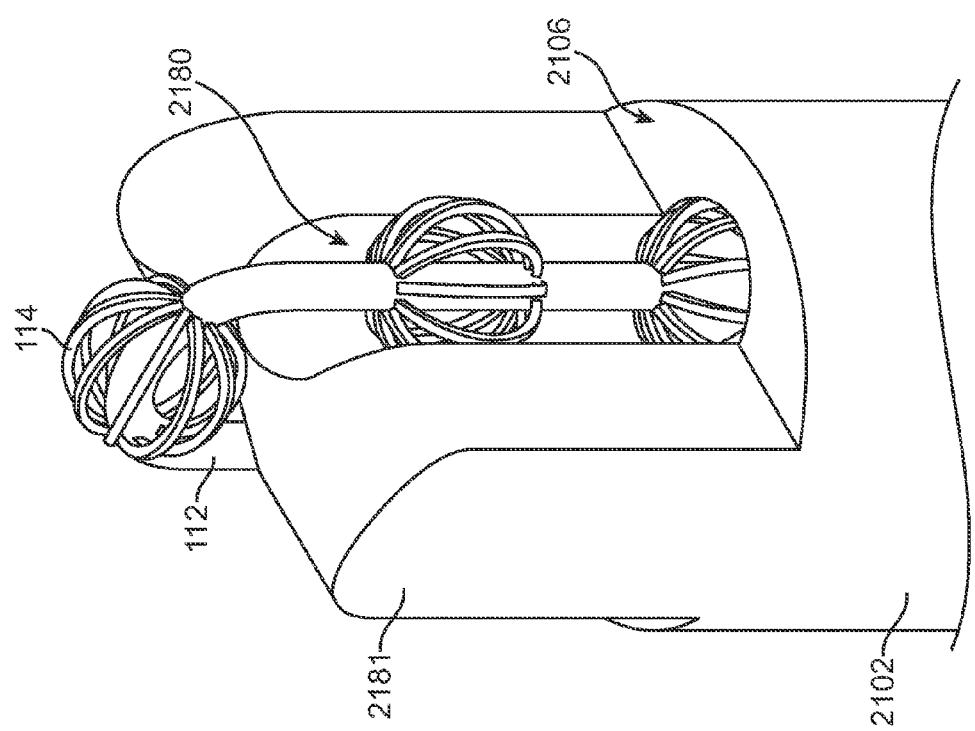

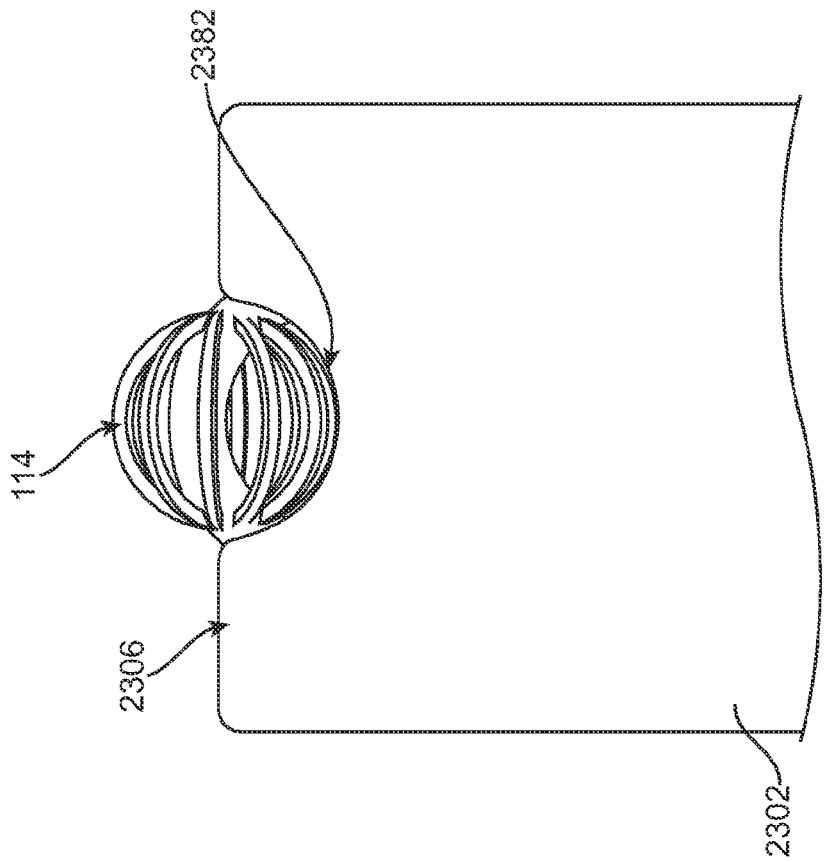
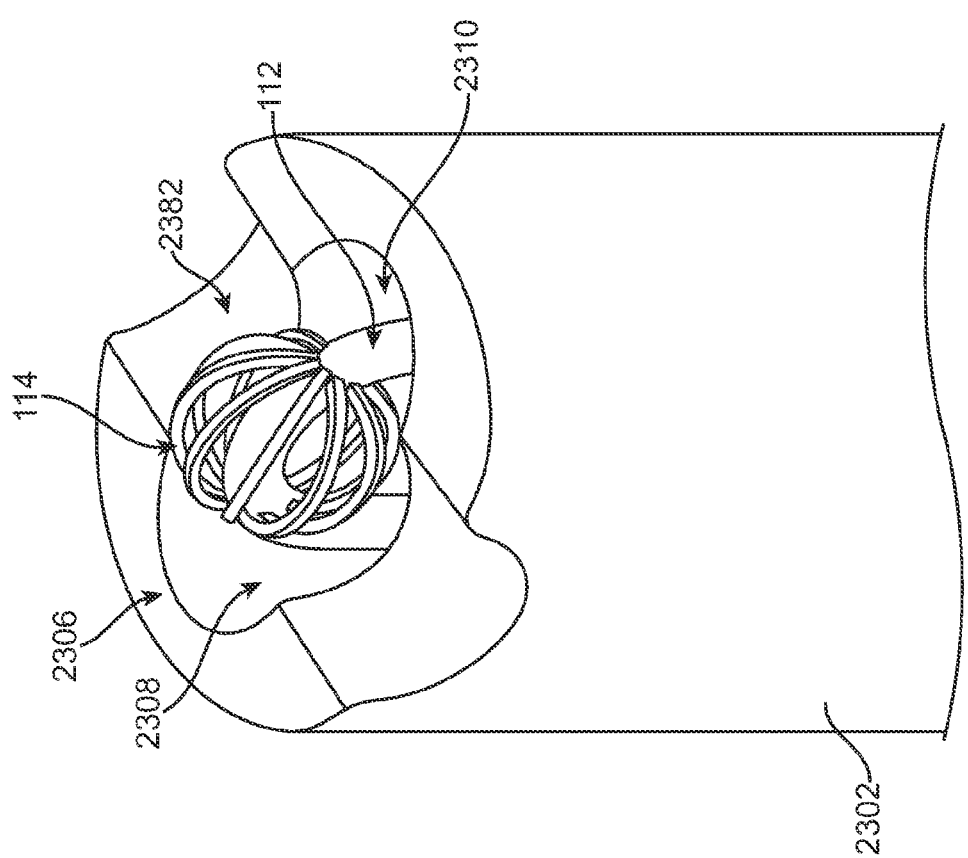
FIG. 23B
FIG. 23A

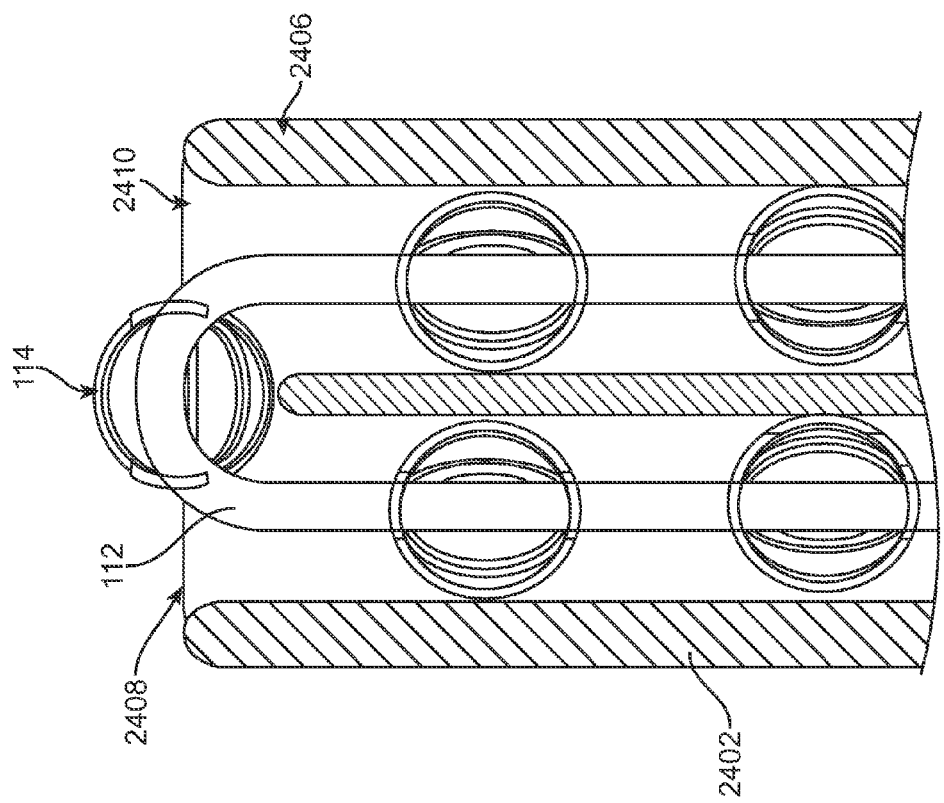
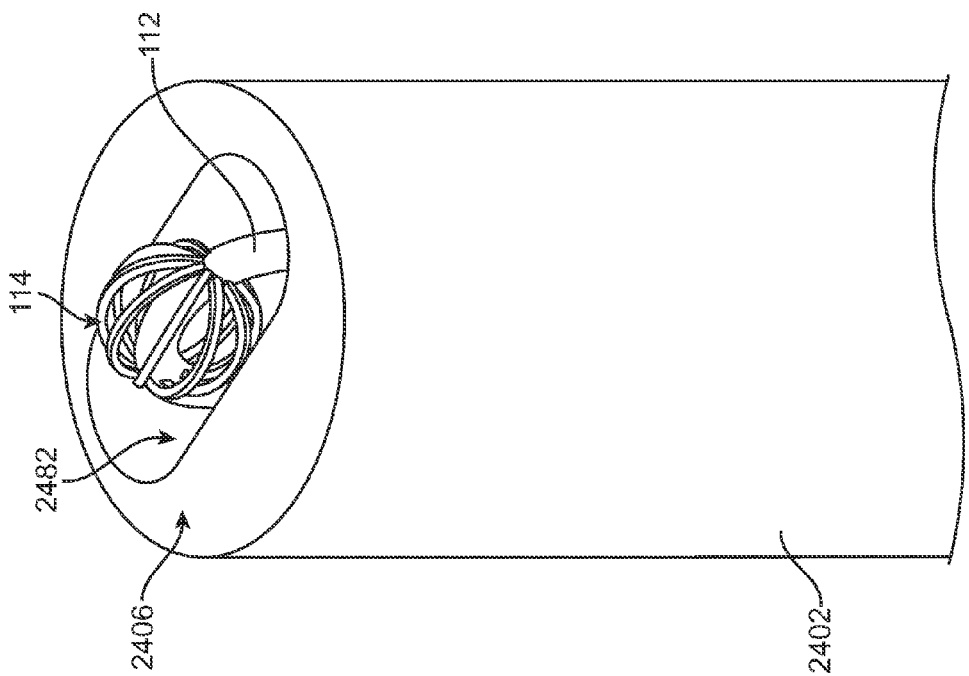
FIG. 24B
FIG. 24A

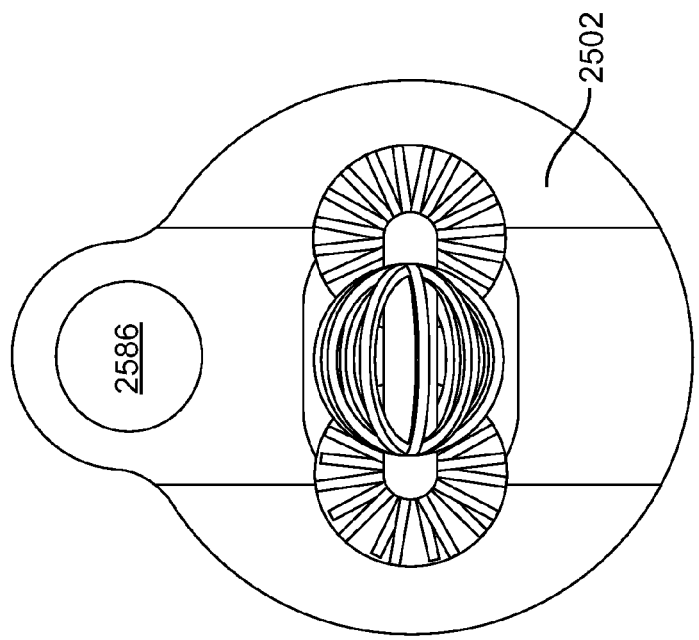
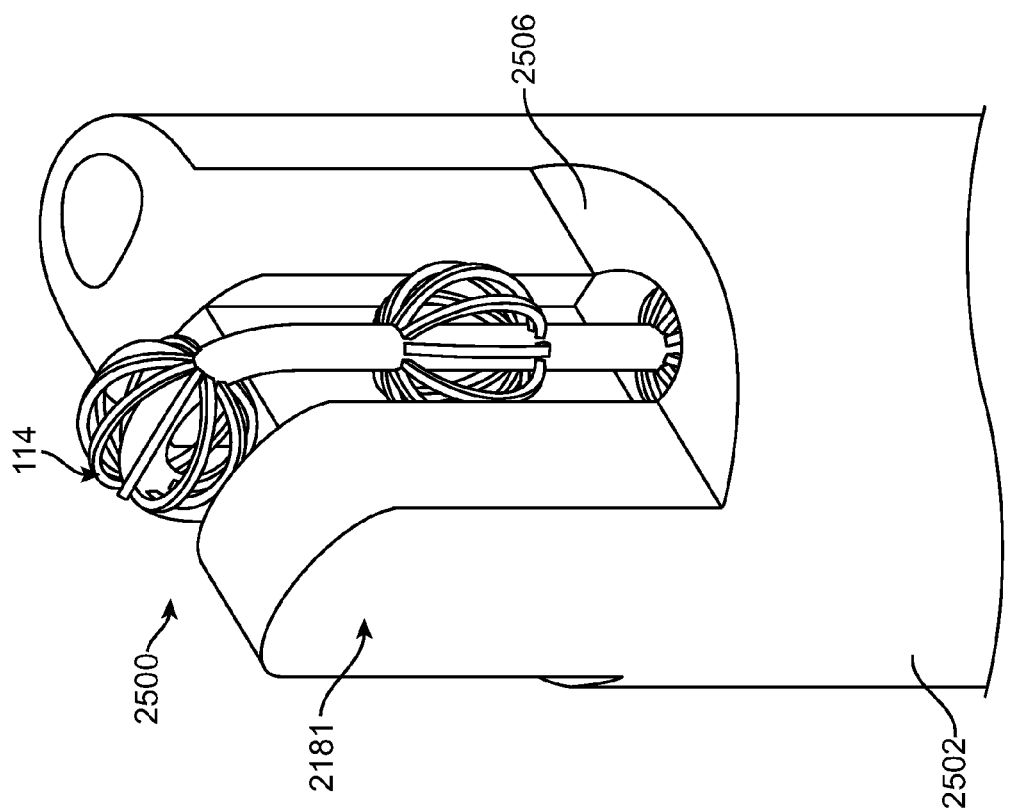
FIG. 25B
FIG. 25A

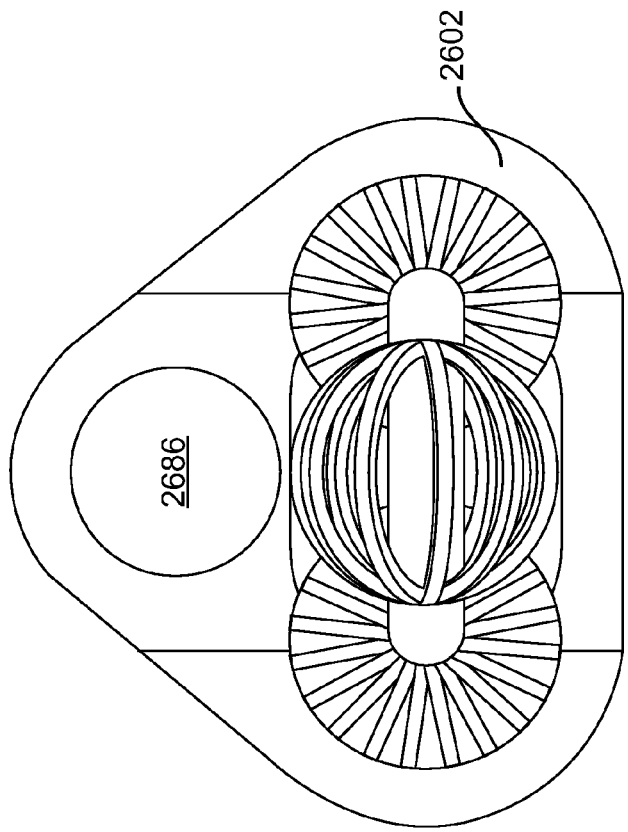
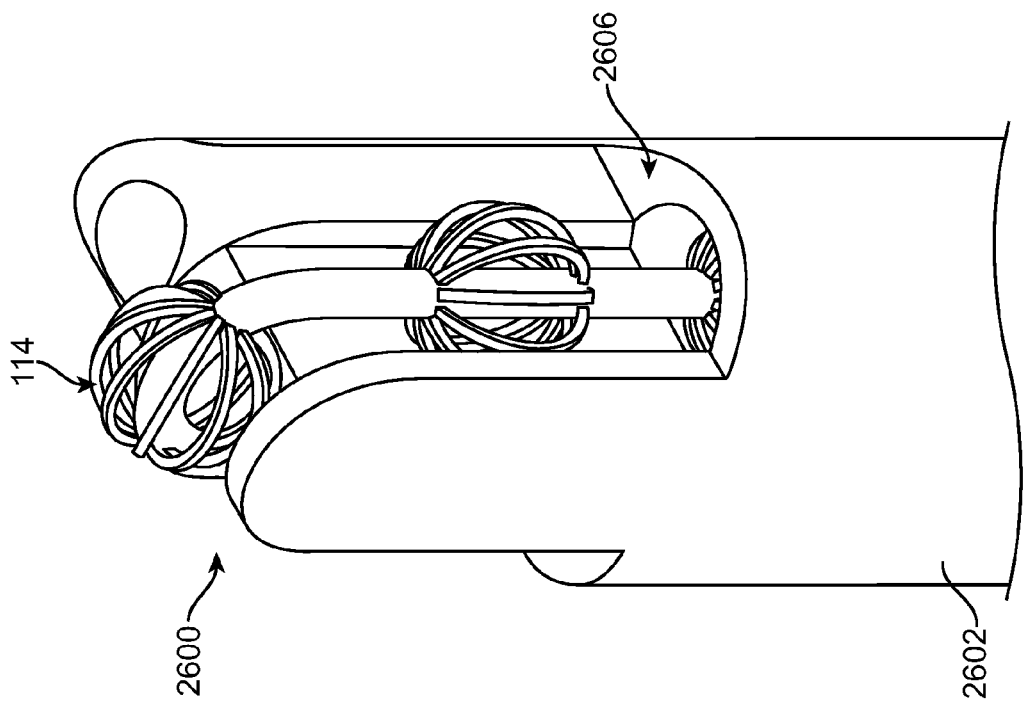
FIG. 26B
FIG. 26A

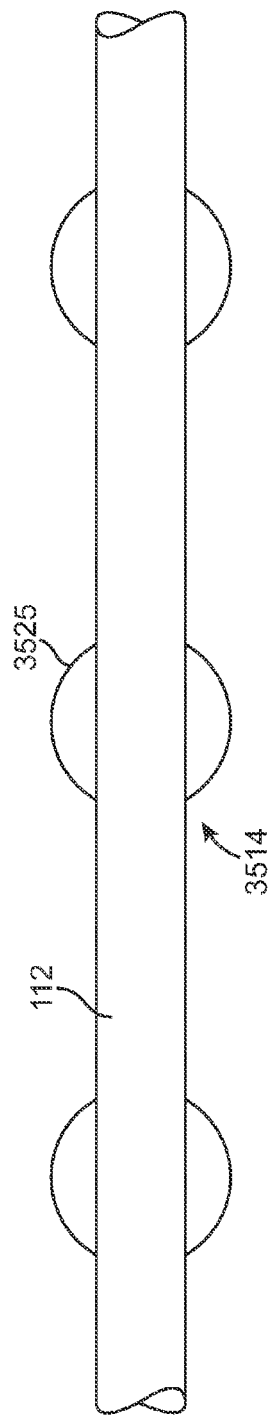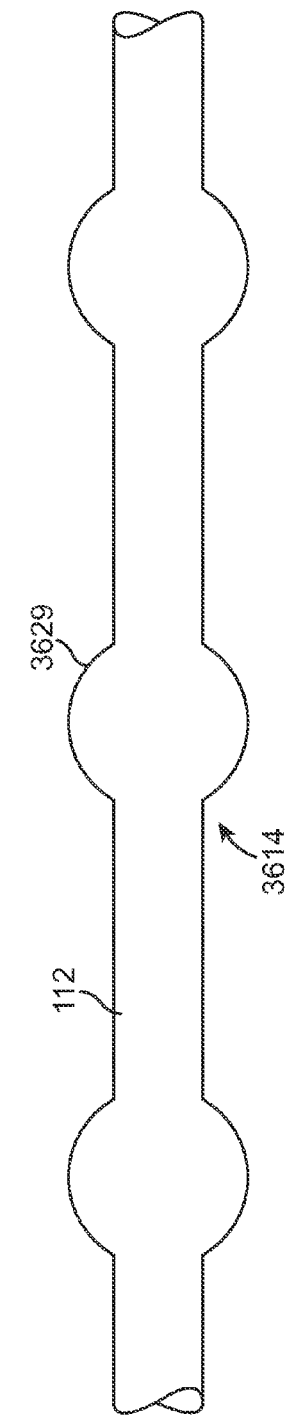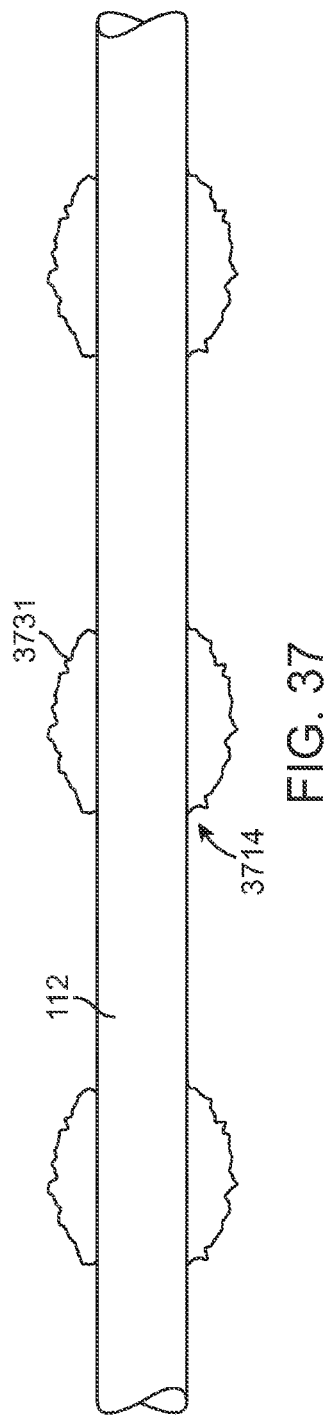

OBSTRUCTION REMOVAL SYSTEM

FIELD OF THE INVENTION

The invention relates to an obstruction removal system for percutaneous removal of clots or obstructions within the vascular system.

BACKGROUND OF THE INVENTION

A number of vascular disorders, such as stroke, pulmonary embolism, peripheral thrombosis, and atherosclerosis, are characterized by formation of occlusions that prevent normal blood flow in blood vessels. For example, an ischemic stroke is a neurological dysfunction caused by a blockage of one of the major arteries of the brain. Hemodynamically significant restriction of arterial blood flow can lead to oxygen deprivation in tissue, referred to as ischemia, and can quickly lead to cell death and organ dysfunction. The brain is the organ most sensitive to ischemia, followed by the heart, the abdominal organs, and the extremities. The brain will usually not tolerate ischemia for very long without massive neuron death (stroke). When treating ischemic events in the brain, it is imperative to restore blood flow quickly and safely. The blockage can be the result of emboli or pieces of thrombotic tissue that have dislodged from other body sites (formed in the heart, carotid artery, or elsewhere) or from the cerebral vessels themselves. The emboli or pieces of thrombotic tissue may migrate downstream to occlude in the narrow cerebral arteries. The blockage may also be caused by the formation of a blood clot at the site of blockage (thrombosis) or the obliteration of the lumen of a blood vessel caused by atherosclerosis.

Stroke is the third most common cause of death in the United States and the most disabling neurologic disorder. Hemorrhagic stroke accounts for 20% of the annual stroke population. Hemorrhagic stroke often occurs due to rupture of an aneurysm or arteriovenous malformation bleeding into the brain tissue, resulting in cerebral infarction. The remaining 80% of the stroke population are ischemic strokes and are caused by occluded vessels that deprive the brain of oxygen-carrying blood.

When a patient presents with neurological deficit, a diagnostic hypothesis for the cause of stroke can be generated based on the patient's history, a review of stroke risk factors, and a neurologic examination. If an ischemic event is suspected, a clinician can tentatively assess whether the patient has a cardiogenic source of emboli, large artery extracranial or intracranial disease, small artery intraparenchymal disease, or a hematologic or other systemic disorder. A head CT scan is often performed to determine whether the patient has suffered an ischemic or hemorrhagic insult. Blood would be present on the CT scan in subarachnoid hemorrhage, intraparenchymal hematoma, or intraventricular hemorrhage.

Traditionally, emergent management of acute ischemic stroke consisted mainly of general supportive care, e.g., hydration, monitoring neurological status, blood pressure control, and/or anti-platelet or anti-coagulation therapy. In 1996, the Food and Drug Administration approved the use of Genentech Inc.'s thrombolytic drug, tissue plasminogen activator (t-PA) or ActivaseB, for treating acute stroke. However, the success rate of this approach is still very low. With this form of therapy, only 30% of patients are expected to realize a good or excellent clinical outcome several months following infusion, and patients who demonstrate signs of intracranial hemorrhage at the time of presentation (on a CT study of their heads) are not candidates for t-PA therapy. Also, intravenous t-PA therapy is associated with an almost 6% fatal intracranial hemorrhage rate.

Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include the following: if the patient has had a previous stroke or serious head trauma in the preceding 3 months, if the patient has a systolic blood pressure above 185 mm Hg or diastolic blood pressure above 110 mm Hg, if the patient requires aggressive treatment to reduce the blood pressure to the specified limits, if the patient is taking anticoagulants or has a propensity to hemorrhage, and/or if the patient has had a recent invasive surgical procedure. Therefore, only a small percentage of selected stroke patients are qualified to receive t-PA.

New classes of "neuroprotectant" agents and "angiogenesis promoters" are being developed and tested. These drugs may extend the effective therapeutic window for stroke therapy and permit better long term outcomes. Their use, however, may require novel delivery systems and often require that the patient be stabilized and ischemia relieved in order to obtain a lasting clinical improvement.

Obstructive emboli have also been mechanically removed from various sites in the vasculature for years. For example, the "Fogarty catheter" or variations thereof has been used, typically in the periphery, to remove clots from arteries found in legs and in arms. These well known devices are described, for example, in U.S. Pat. No. 3,435,826 to Fogarty and in U.S. Pat. No. 4,403,612 to Fogarty, each of which is incorporated by reference herein in its entirety. In general, these patents describe a balloon catheter in which a balloon material is longitudinally stretched when deflated. In procedures for removing emboli using the Fogarty catheter or other similar catheters, it is typical, first, to locate the clot using fluoroscopy. The embolectomy catheter is then inserted and directed to the clot. The distal tip of the balloon catheter is then carefully moved through the center of the clot. Once the balloon has passed through the distal side of the clot, the balloon is inflated. The balloon catheter is then gradually proximally withdrawn. The balloon, in this way, acts to pull the clot proximally ahead of the balloon to a point where it can be retrieved. The majority of procedures using a Fogarty type catheter repeat these steps until the pertinent vessel is cleared of clot material.

A variety of alternative emboli retrieval catheters have also been developed, in which various wire corkscrews and baskets must be advanced distally through the embolic material in order to achieve capture and removal. For example, Concentric Medical, Inc. (located in Mountain View, Calif.) has created an intraluminal clot retrieval system consisting of a nitinol-(Nickel-Titanium alloy) shape memory corkscrew-like coil that is advanced into an occluding clot, such as shown in U.S. Pat. No. 6,663,650; U.S. Pat. No. 6,730,104; and U.S. Pat. No. 7,285,126, each of which is incorporated by reference herein in its entirety. The coil and its attached wire are then withdrawn from the affected vessel, retrieving the thrombus material into a balloon-tipped guiding catheter positioned in the internal carotid artery. However, removal of emboli using such catheters carries potential problems. One such problem occurs when advancing the catheter through the clot dislodges material to a more remote site where removal may become more difficult or impossible.

New devices and methods are thus needed in treating vasculature occlusions in the body, including treating patients with acute ischemic stroke and occlusive cerebrovascular disease, and treating symptomatic patients with embolization or hemodynamic compromise. There are a number of significant problems faced in designing a system which will quickly and easily, yet effectively, evacuate emboli from a treatment location within a blood vessel. First, the small size of certain vessels in which such therapy occurs is a limiting factor in the design of emboli removal systems. Vessels as small as 3 mm in diameter are quite commonly found in the cerebral arteries, coronary arteries, and even certain saphenous vein graph bypass vessels can also be as small as 3 mm or 4 mm; although some can range as high as 7 mm. Nevertheless, a successful emboli removal system must be effective within extremely small working areas and safely traverse the tortuous cerebral vasculature. The system must also be equally effective in larger vessels, those of 5 mm or more in diameter.

Another obstacle is the wide variety in emboli dimensions. Although definitive studies are not available, it is believed that emboli may have approximate diameters ranging anywhere from tens of micrometers to a few hundred micrometers and lengths over 5 cm. More specifically, emboli that are considered dangerous to the patient may have diameters as large as 200 to 300 micrometers or even larger. Often obstruction removal systems have only a single capture device on the distal end to capture and contain the entire obstruction. Such a capture device must be of a relatively large size in order to effectively remove the entire source of vascular occlusion in one pass. However, the relatively large size of the single capture device may not accommodate small vessels.

Thus, an effective emboli removal system must be able to retrieve relatively large embolic particles and clots, at the same time, fit within relatively small vessels. In order to minimize the size of the obstruction removal system, the obstruction removal system of the present invention utilizes a plurality of relatively smaller capture devices that each capture a small portion of the clot or obstruction in order to remove the source of vascular occlusion in a piecemeal or gradual fashion.

BRIEF SUMMARY OF THE INVENTION

Embodiments of the present invention are directed to a system for removing an obstruction within a body lumen. The obstruction removal system includes a catheter shaft and a drive belt. The catheter shaft has a proximal end, a distal end, a first lumen having a distal exit port, and a second lumen having a distal reentry port. The first and second lumens extend side-by-side from the proximal end to the distal end of the catheter shaft. The drive belt is disposed within the catheter shaft in a circulating manner through the first lumen, the distal exit port, the distal reentry port and the second lumen. A plurality of capture devices occur along at least a portion of the drive belt for removing the obstruction from the body lumen when the drive belt is circulated through the catheter shaft. Each capture device is capable of removing at least a portion of the obstruction as the capture device travels between the distal exit port and the distal reentry port of the catheter shaft. In one embodiment of the present invention, the drive belt has integral sections forming the plurality of capture devices thereon for removing the obstruction from the body lumen when the drive belt is circulated through the catheter shaft. In another embodiment of the present invention, the plurality of capture devices are attached to the drive belt for removing the obstruction from the body lumen when the drive belt is circulated through the catheter shaft.

Embodiments of the present invention are also directed to a method for removing an obstruction within a body lumen. An obstruction removal system is positioned near the obstruction within the body lumen. The obstruction removal system includes a catheter shaft, a drive belt, and a plurality of capture devices occurring along at least a portion of the drive belt. The catheter shaft has a proximal end, a distal end, a first lumen having a distal exit port, and a second lumen having a distal reentry port. The first and second lumens extend side-by-side from the proximal end to the distal end of the catheter shaft. The drive belt is circulated though the catheter shaft such that the plurality of capture devices are advanced through the first lumen, through the distal exit port, through the distal reentry port and through the second lumen. At least a portion of the obstruction from the body lumen is removed in a bit-by-bit fashion as each capture device travels between the distal exit port and the distal reentry port of the catheter shaft. The entire obstruction may be removed from the body lumen after the plurality of capture devices are circulated through the catheter shaft in one or more series of passes.

BRIEF DESCRIPTION OF DRAWINGS

The foregoing and other features and advantages of the invention will be apparent from the following description of the invention as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 5 is a perspective view of a capture device in accordance with an embodiment of the present invention.

FIG. 6 is a perspective view of a capture device in accordance with another embodiment of the present invention.

FIG. 7 is a perspective view of a capture device in accordance with another embodiment of the present invention.

FIG. 8 is a perspective view of a capture device in accordance with another embodiment of the present invention.

FIG. 9 is a perspective view of a capture device in accordance with another embodiment of the present invention.

FIG. 10 is a perspective view of a capture device in accordance with another embodiment of the present invention.

FIG. 17A is a perspective view of a proximal portion of an obstruction removal system in accordance with an embodiment of the present invention.

FIG. 17B is a perspective view of the proximal portion of an obstruction removal system taken along line C-C of FIG. 17A.

FIG. 18A is a perspective view of a proximal portion of an obstruction removal system in accordance with another embodiment of the present invention.

FIG. 18B is enlarged perspective view of the proximal portion of an obstruction removal system illustrated in FIG. 18A.

FIG. 21A is a perspective view of a distal portion of an obstruction removal system in accordance with an embodiment of the present invention.

FIG. 21B is a side view of the distal portion of an obstruction removal system illustrated in FIG. 21A.

FIG. 23A is a perspective view of a distal portion of an obstruction removal system in accordance with another embodiment of the present invention.

FIG. 23B is a side view of the distal portion of an obstruction removal system illustrated in FIG. 23A.

FIG. 24A is a perspective view of a distal portion of an obstruction removal system in accordance with another embodiment of the present invention.

FIG. 24B is a side sectional view of the distal portion of an obstruction removal system illustrated in FIG. 24A.

FIG. 25A is a perspective view of a distal portion of an obstruction removal system including a guidewire lumen in accordance with an embodiment of the present invention.

FIG. 25B is a top view of the distal portion of an obstruction removal system illustrated in FIG. 25A.

FIG. 26A is a perspective view of a distal portion of an obstruction removal system including a guidewire lumen in accordance with another embodiment of the present invention.

FIG. 26B is a top view of the distal portion of an obstruction removal system illustrated in FIG. 26A.

FIG. 35 is a side elevational view of a capture device in accordance with another embodiment of the present invention.

FIG. 36 is a side elevational view of a capture device in accordance with another embodiment of the present invention.

FIG. 37 is a side elevational view of a capture device in accordance with another embodiment of the present invention.

DETAILED DESCRIPTION OF THE INVENTION

Figure 1:
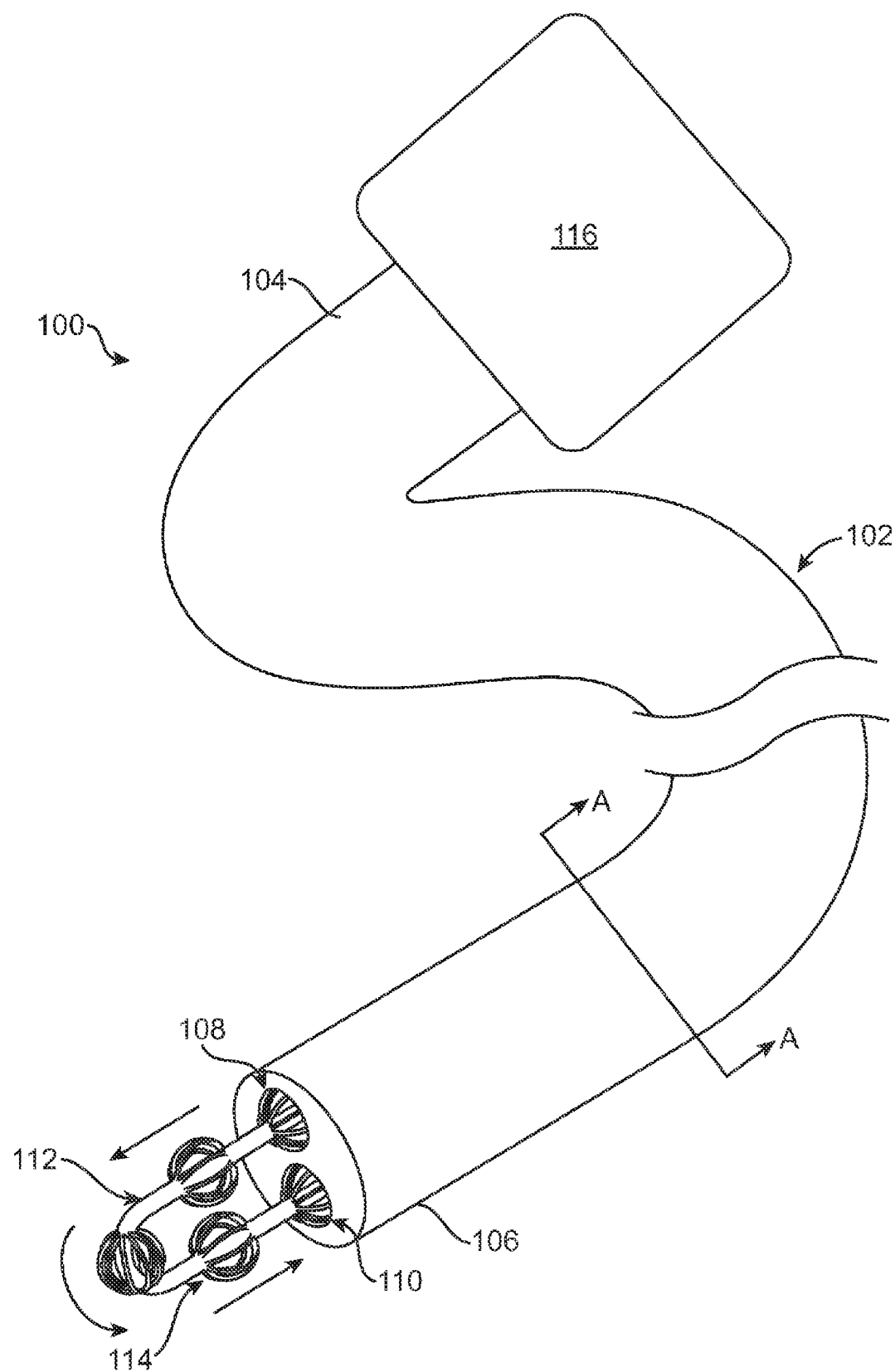
FIG. 1 is a perspective of an obstruction removal system in accordance with an embodiment of the present invention.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels, arteries and veins, such as the cerebral, coronary, iliac, femoral, saphenous, carotid and renal, the invention may also be used in any other body passageways where it is deemed useful. Furthermore, there is no intention to be bound by any expressed or implied theory presented in the preceding technical field, background, brief summary or the following detailed description.

Embodiments of the present invention are related to an obstruction removal system for percutaneous removal of clots or obstructions within the vascular system using a plurality of capture or interference devices on a band. The device may be used for treatment of acute stroke, by removing the source of a vascular occlusion. In one embodiment, the obstruction removal system consists of three main components: a multi-lumen catheter, a plurality of circulating capture or interference devices, and a drive belt. The capture devices exit the catheter body via a first lumen of the catheter, pass through the clot or obstruction while capturing small particles of the obstruction, and pull the clot particles into a second lumen of the catheter. Rather than a single capture device that attempts to remove the entire clot or obstruction, the obstruction removal system of the present invention utilizes a plurality of capture or interference devices that each retrieve a small portion of the clot or obstruction in order to remove the source of vascular occlusion in a bit-by-bit or piecemeal fashion. The plurality of capture or interference devices operate in a circulating or conveyor-like manner, meaning that the plurality of capture or interference devices continuously move and advance through a circuit defined by the lumens of the catheter. After a series of passes, the plurality of capture or interference devices collectively remove the entire source of the vascular occlusion.

The plurality of capture or interference devices may be, for example, basket or cage-like devices fixed to the drive belt. The capture devices may be cylindrical, spherical, bowl or umbrella shaped, elongated oval shaped (i.e., watermelon-shaped), crescent or scoop shaped, spool shaped, or any other appropriate configuration which may retrieve the obstruction material. The capture devices may be a mesh design or may include strands that extend parallel to the drive belt. In another embodiment, the plurality of capture or interference devices may be hairbrush-like or wire-brush devices having a plurality of bristles that ensnare portions of the clot or obstruction. The capture or interference devices may be fabricated out of a flexible material that allows them to deploy or expand upon exiting the first lumen of the catheter and contract upon re-entry into the second lumen of the catheter. The number of capture or interference devices, the geometry of such devices, the size of such devices, and the spacing between adjacent devices may be varied to optimize the clot or obstruction retrieval.

In one embodiment of the present invention, the drive belt may be a wire. The plurality of capture devices may be formed by integral curly, protuberant or coiled sections of the wire. For example, the drive belt may be a continuous wire coil, may include periodic coiled sections, or may include a random protuberant or curly pattern. The drive belt and integral capture devices may be fabricated out of a flexible, shape-memory material such as Nitinol. When formed from a shape memory material, the wire drive belt may travel in a straightened configuration within the first lumen of the catheter during travel to the target site. Upon exiting a distal end of the catheter, the drive belt returns to its coiled or curly configuration in order to form the capture devices and retrieve small particles of the obstruction. Upon re-entry into the catheter via the second lumen, the drive belt remains in the coiled, protuberant, or curly configuration in order to retain the captured clot particles.

In an embodiment, the obstruction removal system has a drive mechanism at its proximal end for driving the drive belt and capture devices through the catheter. The drive mechanism may be a mechanical pulley-like system manually, electronically, hydraulically, pneumatically, etc. operated by the device operator, which advances the drive belt and capture devices located thereon through the catheter in a circulating or conveyor-like manner. "Circulating manner" as used herein is intended to mean that the drive belt and capture devices located thereon move in a continuous manner through a cycle or circuit defined by the lumens of the catheter. In another embodiment, the drive mechanism may be an aspiration or vacuum source and/or a pressurization source at the proximal end of the obstruction removal system in order to advance the drive belt and capture devices located thereon through the catheter in a circulating or conveyor-like manner. In one embodiment, the pressurization source may include a fluid in order to provide further breakdown of the clot or obstruction in addition to the mechanical breakdown provided by the capture devices.

In an embodiment, the obstruction removal system includes means for removing or cleaning the captured clot pieces from the capture devices. For example, in one embodiment of the present invention, the captured clot is removed by a vacuum in communication with the proximal end of the obstruction removal system for pulling the captured clot particles from the capture devices. The vacuum provides a suction force along the second lumen of the catheter, ensuring that loose clot particles do not migrate downstream. In addition, the vacuum creates a negative pressure at the distal reentry port of the second lumen and thus may pull clot material towards the capture devices, thus facilitating clot retrieval. In another embodiment, a fluid under pressure may be applied at the proximal end of the obstruction removal system in order to clean the captured clot particles from the drive belt and the capture devices as they pass through the drive mechanism. In another example, the drive mechanism may include collinear pulleys in which the second pulley squeegees or wipes the captured clot particles from the capture devices as they pass through the intersection of the first and second pulleys. In yet another example, the drive mechanism is a single pulley and a brush-like element removes the captured clot particles from the capture devices prior to reaching the single pulley.

In another embodiment of the present invention, a linear band having two opposite ends is passed through the catheter via a dual-spool configuration. The linear band may be a wire. One end of the band is secured to a first spool, and the other end of the band is secured to a second spool. The band is wound around the first spool prior to usage, and the band is transferred to the second spool as it is advanced through the catheter. In this embodiment, the captured clot particles would not have to be removed from the band and capture devices since the band operates in a non-circulating manner. "Non-circulating manner" as used herein is intended to mean that the band and capture devices located thereon move through a path defined by the lumens of the catheter but do not operate in a continuous manner through a cycle or circuit. Further details and description of embodiments of the present invention are provided below with reference to FIGS. 1-56.

Obstruction Removal System

Referring to FIG. 1, obstruction removal system 100 is illustrated according to an embodiment of the present invention. Obstruction removal system 100 includes a catheter with an elongate multi-lumen shaft 102 having a proximal end 104 and a distal end 106. A distal exit port 108 and a distal reentry port 110 are located at the distal end 106 of catheter shaft 102. A drive belt 112 carries a plurality of capture or interference devices 114 in a circulating or conveyor-like manner through catheter shaft 102 via a drive mechanism 116 located at the proximal end 104 of catheter shaft 102. Drive belt 112 is an endless loop having the plurality of capture or interference devices 114 occurring along the length thereof that continuously moves and advances the capture devices 114 through a circuit or cycle defined by the lumens of catheter 102. Obstruction removal system 100 utilizes the plurality of capture or interference devices 114 to remove a clot or obstruction in a bit-by-bit or piecemeal fashion. More particularly, following the directional arrows labeled on FIG. 1, drive belt 112 carrying capture devices 114 exit catheter shaft 102 via distal exit port 108 of catheter shaft 102, pass through a clot or obstruction while retrieving small particles of the obstruction, and pull the captured clot particles back into catheter shaft 102 via distal reentry port 110 of catheter shaft 102. After a series of passes or cycles, the plurality of capture or interference devices 114 collectively remove the entire source of the vascular occlusion.

Figure 2B:
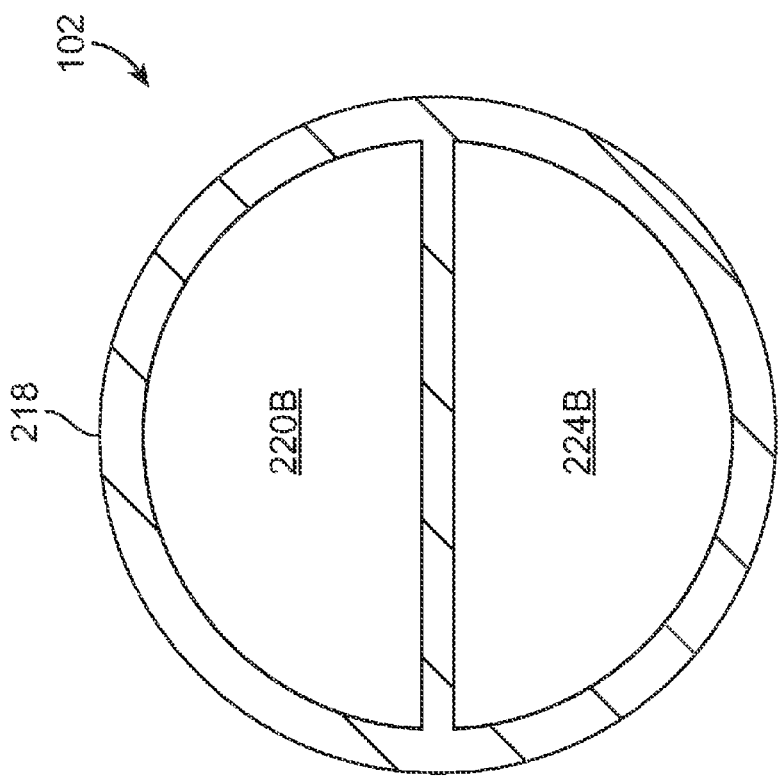
FIG. 2B is a cross-sectional view of an obstruction removal system in accordance with another embodiment of the present invention taken along line A-A of FIG. 1.
Figure 2A:
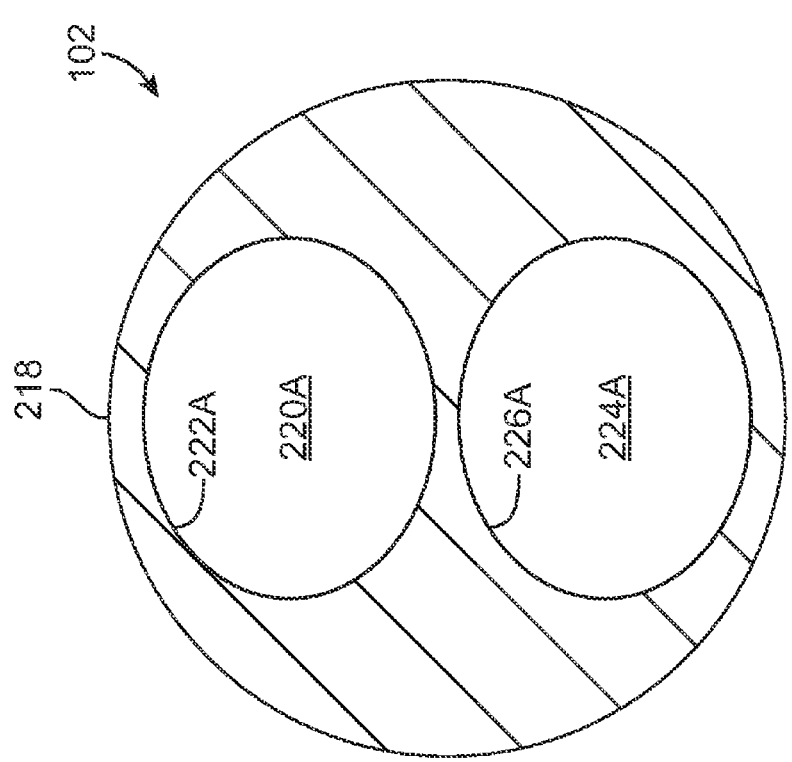
FIG. 2A is a cross-sectional view of an obstruction removal system in accordance with an embodiment of the present invention taken along line A-A of FIG. 1.

FIG. 2A is a cross-sectional view of obstruction removal system 100 taken along line A-A of FIG. 1 in accordance with an embodiment of the present invention. Catheter shaft 102 has an outside surface 218 and defines dual side-by-side lumens extending there through. First lumen 220A is formed via an inside surface 222A and extends the length of catheter shaft 102 from the proximal end 104 to the distal end 106, terminating in distal exit port 108. Second lumen 224A is formed via an inside surface 226A and extends the length of catheter shaft 102 from the proximal end 104 to the distal end 106, terminating in distal reentry port 110. As shown in FIG. 2A, side-by-side first lumen 220A and second lumen 224A may each have a circular cross-section and be of an approximately equal size or diameter. The size or diameter of first lumen 220A and second lumen 224A must each be sufficient to receive the plurality of capture devices 114. In addition, it will be apparent to those of ordinary skill in the art that first lumen 220A and second lumen 224A may have any appropriate cross-sectional shape. For example, as shown in FIG. 2B, first lumen 220B and second lumen 224B may alternatively each have a semi-circular cross-section.

Figure 3:
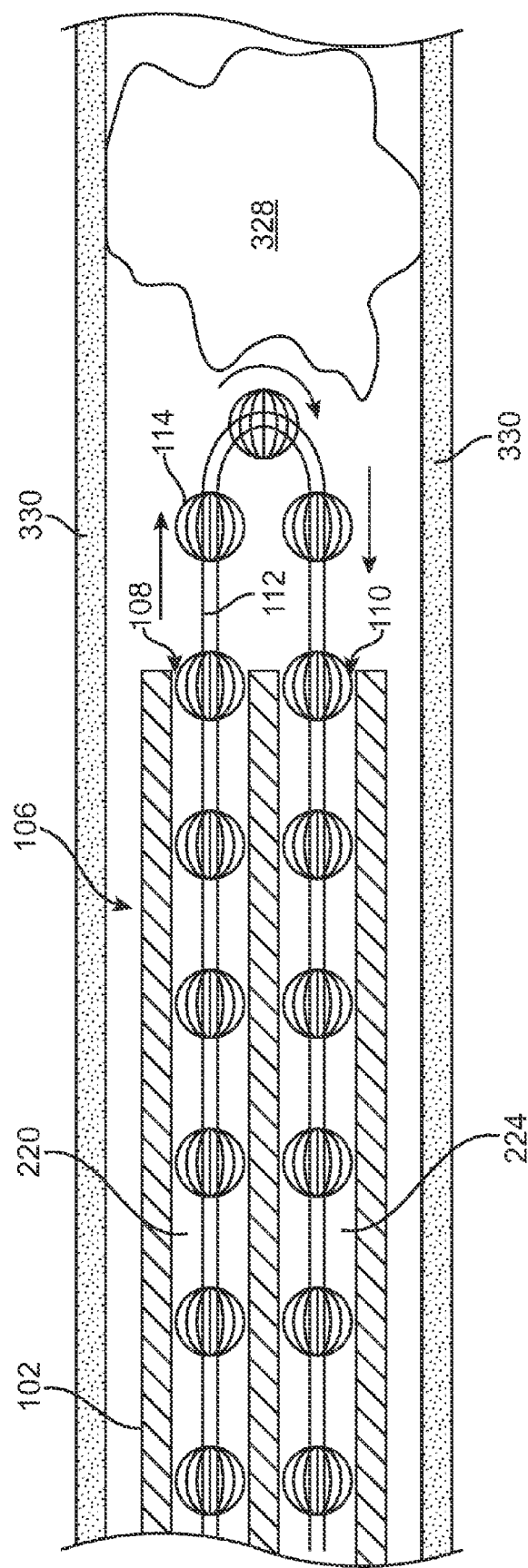
FIG. 3 is a sectional view of a distal portion of an obstruction removal system in accordance with an embodiment of the present invention.

FIG. 3 is a sectional view of the distal end 106 of catheter shaft 102 placed within a blood vessel 330 such that obstruction removal system 100 may be utilized to remove clot or obstruction 328. Drive belt 112 having a plurality of capture or interference devices 114 thereon extends through first lumen 220 and second lumen 224 of catheter shaft 102. Drive mechanism 116 operates to circulate the plurality of capture devices 114 through catheter shaft 102 in a conveyor-like manner. More specifically, following the directional arrows labeled on FIG. 3, drive mechanism 116 operates to essentially pull the plurality of capture devices 114 through second lumen 224 such that they exit catheter shaft 102 via distal exit port 108. The plurality of capture devices 114 then pass through clot or obstruction 328 while capturing small particles thereof. Capture devices 114 re-enter catheter shaft 102 via distal reentry port 110 and carry or direct the captured clot particles through second lumen 224 of the catheter shaft 102 to be cleansed or removed there from.

Thus, obstruction 328 within a body lumen is removed by positioning obstruction removal system 100 near the obstruction within the body lumen and circulating drive belt 112 though catheter shaft 102 such that the plurality of capture devices 114 are advanced through the first lumen 220, through the distal exit port 108, through the distal reentry port 110 and through the second lumen 224. At least a portion of obstruction 328 is removed from the body lumen in a bit-by-bit fashion as each capture device 114 travels between distal exit port 108 and distal reentry port 110 of catheter shaft 102. The entire obstruction 328 is removed from the body lumen after drive belt 112 and the plurality of capture devices 114 located thereon are circulated through catheter shaft 102 in a series of passes.

Catheter Shaft

FIGS. 21A-24B illustrate alternative embodiments for catheter shaft 102, which guide or track drive belt 112 with capture devices 114. One embodiment illustrated in FIGS. 21A-21B contains a track 2180 created by an extension 2181 of distal end 2106 of catheter shaft 2102. Extension 2181 is a band of material that distally extends from distal end 2106 of catheter shaft 2102 and spans the entire diameter of catheter shaft 2102. Track 2180 is a semi-circular groove formed on opposing sides of extension 2181 that is coaxially aligned with the first lumen (not shown) and the second lumen (not shown) in order to guide capture devices 114 between distal exit port 2108 and distal reentry port 2110 of catheter shaft 2102. Extension 2181 and track 2180 may be formed by removing a portion of catheter shaft 2102, or may be formed as a separate piece and attached to the distal end 2106 of catheter shaft 2102.

Figure 22B:
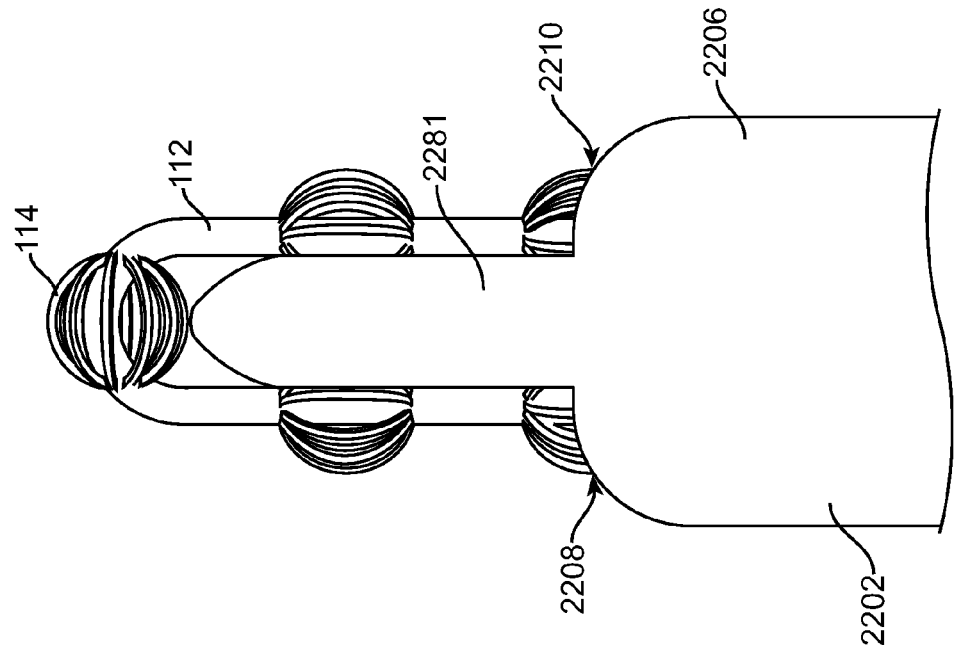
FIG. 22B is a side view of the distal portion of an obstruction removal system illustrated in FIG. 22A.
Figure 22A:
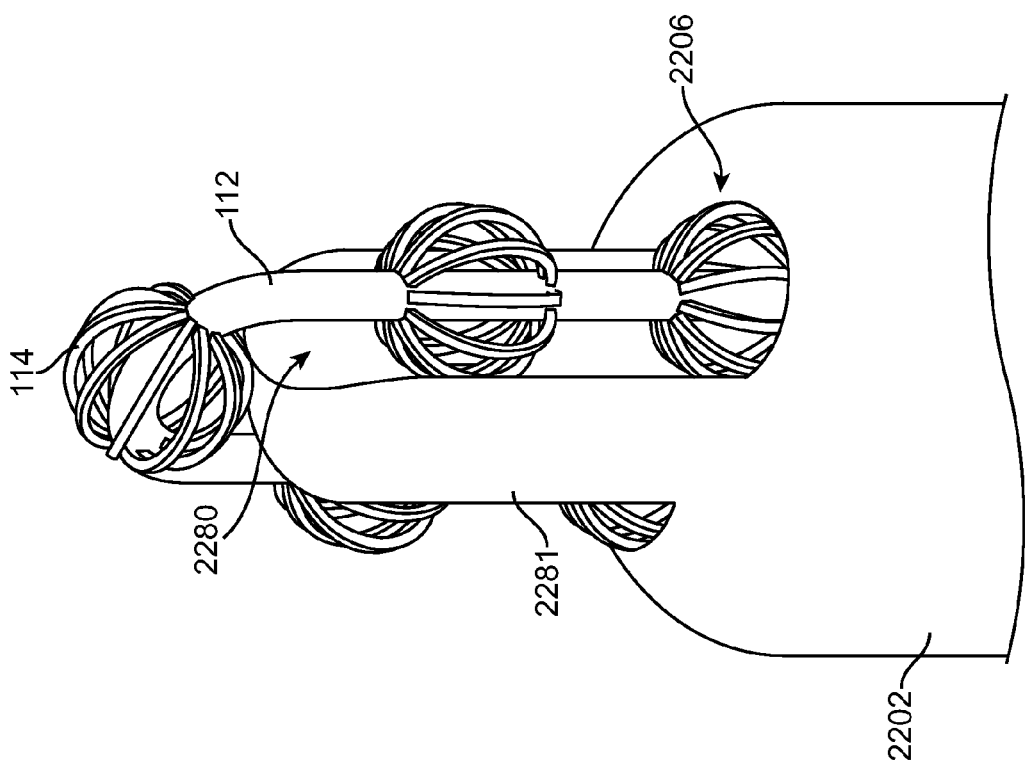
FIG. 22A is a perspective view of a distal portion of an obstruction removal system in accordance with another embodiment of the present invention.

Another embodiment illustrated in FIGS. 22A-22B contains a track 2280 created by extension 2281 of distal end 2206 of catheter shaft 2202. Track 2280 is similar to track 2180 in that extension 2281 is a band of material that distally extends from distal end 2206 of catheter shaft 2202. However, extension 2281 does not span the entire diameter of catheter shaft 2202 and includes tapered outer surfaces rather than semi-circular outer surfaces as in the embodiment of FIGS. 21A-21B. Track 2280 is a semi-circular groove formed on opposing sides of extension 2281 that is coaxially aligned with the first lumen (not shown) and the second lumen (not shown) in order to guide capture devices 114 between distal exit port 2208 and distal reentry port 2210 of catheter shaft 2202. Extension 2281 and track 2280 may be formed by removing a portion of catheter shaft 2202, or may be formed as a separate piece and attached to the distal end 2206 of catheter shaft 2202.

Another embodiment for guiding or tracking drive belt 112 with capture devices 114 thereon over distal end 106 of catheter shaft 102 is illustrated in FIGS. 23A-23B. This embodiment includes a notch or ridge 2382 that is cut out of distal end 2306 of catheter shaft 2302 and spans the entire diameter of catheter shaft 2302. Notch 2382 has a depth approximately equal to half the outer diameter of a capture device 114 so that half of each capture device 114 will extend beyond distal end 2306 of catheter shaft 2302 in order to retrieve the target clot material. Capture devices 114 ride along notch 2382 which thus helps to guide capture devices 114 between distal exit port 2308 and distal reentry port 2310 of catheter shaft 102. When notch 2382 spans the entire diameter of catheter shaft 2302, the entire capture device 114 is exposed from the catheter shaft, as shown in FIG. 23B. Notch 2382 may be formed by removing a portion of catheter shaft 2302.

Another embodiment illustrated in FIGS. 24A-24B contains a notch or ridge 2482 that is cut out of distal end 2406 of catheter shaft 2402. Notch 2482 is similar to notch 2382 except that notch 2482 does not span the entire diameter of catheter shaft 2402. Since notch 2482 does not span the entire diameter of catheter shaft 2402, only a portion of capture device 114 is exposed from the catheter shaft, as shown in FIG. 24B. Notch 2482 has a depth approximately equal to half the outer diameter of a capture device 114 so that half of each capture device 114 will extend beyond distal end 2406 of catheter shaft 2402 in order to retrieve the target clot material. Capture devices 114 ride along notch 2482 which thus helps to guide capture devices 114 between distal exit port 2408 and distal reentry port 2410 of catheter shaft 2402. Notch 2482 may be formed by removing a portion of catheter shaft 2402.

Catheter shaft 102 may be an extruded multi-lumen shaft formed of any suitable flexible polymeric material. Non-exhaustive examples of material for catheter shaft 102 are polyethylene terephalate (PET), nylon, polyethylene, PEBAX, or combinations of any of these, either blended or co-extruded. Optionally, a portion of catheter shaft 102 may be formed as a composite having a reinforcement material incorporated within a polymeric body in order to enhance strength, flexibility, and/or toughness. Suitable reinforcement layers include braiding, wire mesh layers, embedded axial wires, embedded helical or circumferential wires, and the like. In an embodiment, proximal end 104 of catheter shaft 102 may in some instances be formed from a reinforced polymeric tube, for example, as shown and described in U.S. Pat. No. 5,827,242 to Follmer et al. which is incorporated by reference herein in its entirety.

Catheter shaft 102 may include a separate guidewire lumen in order to track obstruction removal system 100 to the target obstruction. For example, in one embodiment illustrated in FIGS. 25A-25B, catheter shaft 2502 includes a guidewire lumen 2586 for receiving a guidewire (not shown). In such an embodiment, obstruction removal system 2500 includes three lumens extruded within catheter shaft 2502: the first lumen (not shown) and the second lumen (not shown) for tracking capture devices 114 and drive belt 112 through catheter shaft 102, and guidewire lumen 2586. In FIGS. 25A-25B, catheter 2502 has a substantially circular cross-section with a semi-circular protrusion extending therefrom in which guidewire lumen 2586 is at least partial situated. Guidewire lumen 2586 may extend the entire length of catheter shaft 2502 in an over-the-wire configuration. However, as would be understood by one of ordinary skill in the art, guidewire lumen 2586 may alternately extend only within the distal portion of catheter shaft 2502 in a rapid-exchange configuration. Guidewire lumen 2586 is off-center to catheter shaft 2502 in order to reduce the incidence of capture devices 114 and/or drive belt 112 from coming into contact with the guidewire. During operation, the guidewire may be pulled proximally within guidewire lumen 2586 in order to further prevent interruption with the clot retrieving function of obstruction removal system 2500. FIGS. 25A-25B illustrate catheter shaft 2502 including an extension 2181 of distal end 2506 of catheter shaft 2502, which forms a track for guiding the capture devices and drive belt similar to that described above with respect to FIGS. 21A-21B.

Another embodiment of an obstruction removal system with a guidewire lumen is illustrated in FIGS. 26A-26B. Catheter shaft 2602 includes a guidewire lumen 2686 for receiving a guidewire (not shown). In such an embodiment, obstruction removal system 2600 includes three lumens extruded within catheter shaft 2602: the first lumen (not shown) and the second lumen (not shown) for tracking capture devices 114 and drive belt 112 through catheter shaft 102, and guidewire lumen 2686. In FIGS. 26A-26B, catheter shaft 2602 has a substantially triangular cross-section to accommodate the three lumens. The triangular cross-section minimizes the crossing profile of the catheter shaft 2602. Guidewire lumen 2686 may extend the entire length of catheter shaft 2602 in an over-the-wire configuration or may alternately extend only within the distal portion of catheter 2602 in a rapid-exchange configuration. Guidewire lumen 2686 is off-center to catheter shaft 2602 in order to reduce the incidence of capture devices 114 and/or drive belt 112 from coming into contact with the guidewire. During operation, the guidewire may be pulled proximally within guidewire lumen 2686 in order to further prevent interruption with the clot retrieving function of obstruction removal system 2600. FIGS. 26A-26B illustrate catheter shaft 2602 including an extension of distal end 2606 of catheter shaft 2602, which forms a track for guiding the capture devices and drive belt similar to that described above with respect to FIGS. 21A-21B.

Figure 27A:
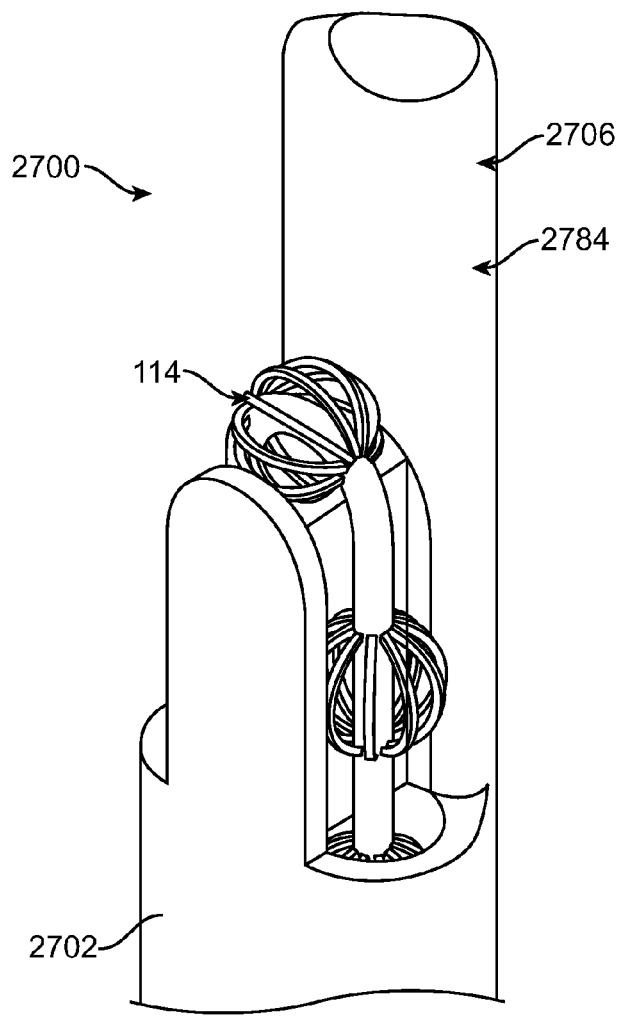
FIG. 27A is a perspective view of a distal portion of an obstruction removal system including a guidewire lumen in accordance with another embodiment of the present invention.
Figure 27B:
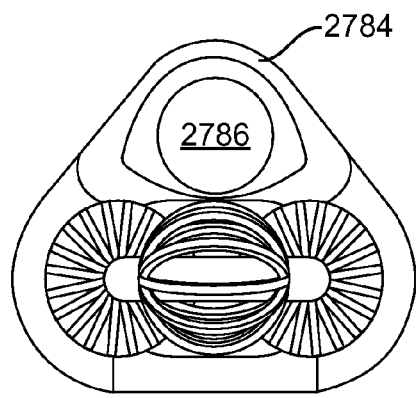
FIG. 27B is a top view of the distal portion of an obstruction removal system illustrated in FIG. 27A.

Another embodiment of an obstruction removal system having a guidewire lumen is illustrated in FIGS. 27A-27B. Catheter shaft 2702 includes a guidewire lumen 2786 for receiving a guidewire (not shown). Guidewire lumen 2786 has a distal portion defined by a guidewire lumen extension 2784 that extends beyond the distal exit and reentry ports of catheter shaft 2702 in order to reduce the incidence of capture devices 114 and/or drive belt 112 from coming into contact with the guidewire. Obstruction removal system 2700 includes three lumens extruded within catheter shaft 2702: the first lumen (not shown) and the second lumen (not shown) for tracking capture devices 114 and drive belt 112 through catheter shaft 102, and guidewire lumen 2786. Guidewire lumen 2786 may extend the entire length of catheter shaft 2702 in an over-the-wire configuration or may alternately extend only within the distal portion of catheter shaft 2702 in a rapid-exchange configuration. In FIGS. 27A-27B, catheter shaft 2702 has a substantially triangular cross-section to accommodate the three lumens. This triangular cross-section minimizes the crossing profile of the catheter shaft 2702. Guidewire lumen 2786 is off-center to catheter shaft 2702 in order to further reduce the incidence of capture devices 114 and/or drive belt 112 from coming into contact with the guidewire. During operation, the distal end 2706 of catheter shaft 2702, which is on guidewire lumen extension 2784, is preferably embedded within the clot. The capture devices 114 exiting from the distal exit port of the catheter shaft 2702 would thus be allowed to come into contact with the proximal end of the clot.

Figures 28A, 28B:
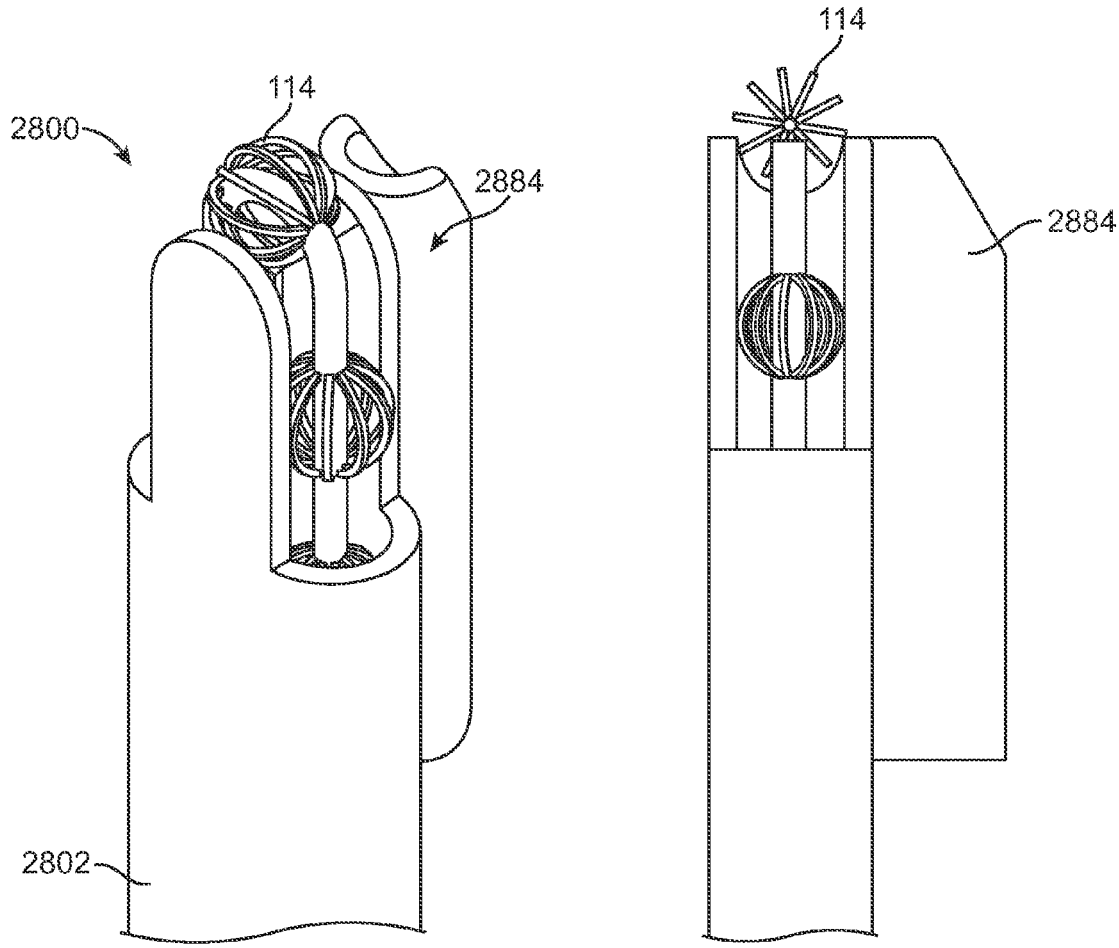
FIG. 28A is a perspective view of a distal portion of an obstruction removal system including a guidewire lumen in accordance with another embodiment of the present invention.
FIG. 28B is a side sectional view of the distal portion of an obstruction removal system illustrated in FIG. 28A.
Figure 28C:
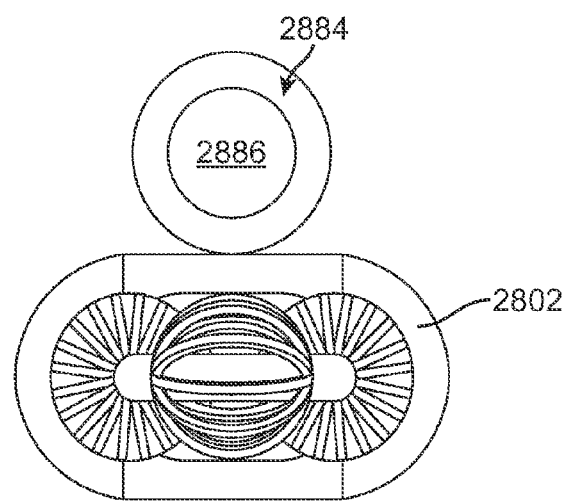
FIG. 28C is a top view of the distal portion of an obstruction removal system illustrated in FIG. 28A.

Another embodiment of an obstruction removal system having a guidewire lumen is illustrated in FIGS. 28A-28C. Catheter shaft 2802 includes a tubular guidewire shaft 2884 that defines guidewire lumen 2886 for receiving a guidewire (not shown). Guidewire shaft 2884 is attached to the outside surface of catheter shaft 2802. In such an embodiment, obstruction removal system 2800 includes three lumens: the first lumen (not shown) and the second lumen (not shown) for tracking capture devices 114 and drive belt 112 through catheter shaft 102, and guidewire lumen 2886. The first lumen and the second lumen are both extruded within catheter shaft 2802, while guidewire lumen 2886 is attached to the outside surface of catheter shaft 2802. In FIGS. 28A-28C, catheter shaft 2802 has a substantially oval or oblong cross-section to accommodate the three lumens. This oval or oblong cross-section minimizes the crossing profile of the catheter shaft 2802. As shown in FIGS. 28A-28C, guidewire shaft 2884 may be a cylindrical hypotube extending along only the distal portion of catheter shaft 2802 in a rapid-exchange configuration. However, as would be understood by one of ordinary skill in the art, guidewire shaft 2884 and guidewire lumen 2886 formed thereby may alternately extend the entire length of catheter shaft 2802 in an over-the-wire configuration. During operation, the guidewire may be pulled proximally within guidewire lumen 2886 in order to prevent interruption with the clot retrieving function of obstruction removal system 2800.

Capture Devices

Figure 4:
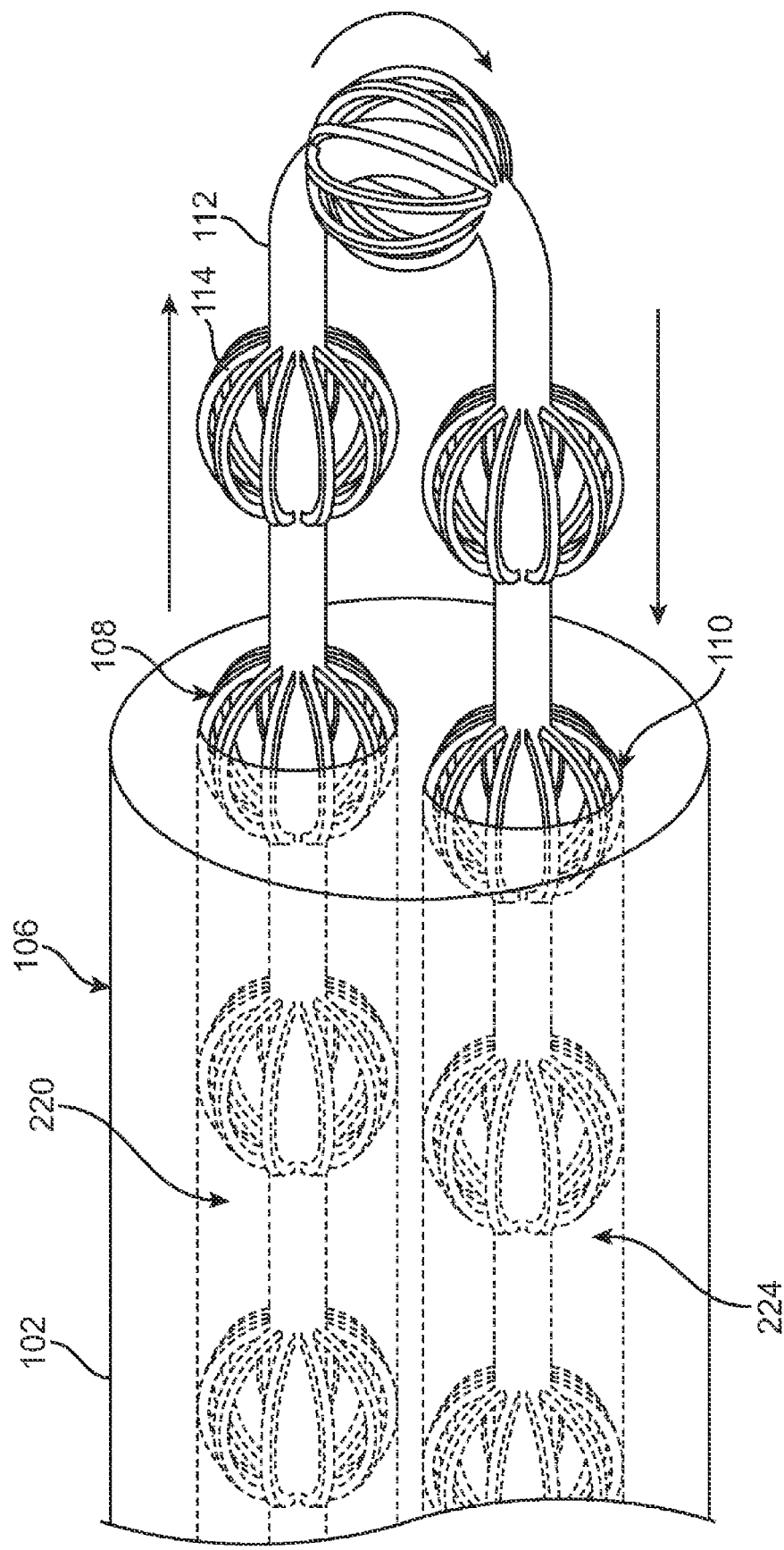
FIG. 4 is an enlarged perspective view of a distal portion of an obstruction removal system in accordance with an embodiment of the present invention.

The plurality of capture devices may assume various forms. FIG. 4 is an enlarged perspective view of distal end 106 of catheter shaft 102 showing capture devices 114 circulating within catheter shaft 102 through a path defined by first lumen 220 and second lumen 224. As shown in FIGS. 4-5, capture devices 114 may be a spherical basket 532 fixed to drive belt 112. The outer diameter of spherical basket 532 is approximately 0.010 inches to 0.020 inches. The relatively smaller size of capture devices 114 minimizes the size of obstruction removal system 100 such that obstruction removal system 100 may fit within relatively small vessels, and at the same time, collectively retrieve relatively large emboli. Baskets 532 may include strands 534 that extend parallel to drive belt 112 and parallel to blood flow when located within the body lumen.

In another embodiment illustrated in FIG. 6, capture devices 614 may be a bowl or umbrella shaped basket 638 fixed to drive belt 112. Baskets 638 may have an outer diameter similar to that of spherical basket 532 of FIG. 5 or may expand to a greater diameter. Baskets 638 may include strands 634 that extend parallel to drive belt 112 and parallel to blood flow when located within the body lumen.

In another embodiment illustrated in FIG. 7, capture devices 714 may be an elongated oval (i.e., watermelon-shaped) basket 740 fixed to drive belt 112. Baskets 740 may have an outer diameter similar to that of spherical basket 532 of FIG. 5 or may have a greater or lesser diameter. Baskets 740 may include strands 734 that extend parallel to drive belt 112 and parallel to blood flow when located within the body lumen.

In another embodiment illustrated in FIG. 8, capture devices 814 may be a spherical basket 832 fixed to drive belt 112. Baskets 832 may have an outer diameter similar to that of spherical basket 532 of FIG. 5. Baskets 832 are formed of a woven or stamped mesh 836 to capture particles of a clot or obstruction.

In another embodiment illustrated in FIG. 9, capture devices 914 may be a bowl or umbrella shaped basket 938 fixed to drive belt 112. Baskets 938 may expand to an outer diameter similar to or greater than that of spherical basket 832 of FIG. 8. Baskets 938 are also formed of a woven or stamped mesh 936 to capture particles of a clot or obstruction.

In another embodiment illustrated in FIG. 10, capture devices 1014 may be an elongated oval (i.e., watermelon-shaped) basket 1040 fixed to drive belt 112. Baskets 1040 may have an outer diameter similar to, or greater or lesser than that of spherical basket 832 of FIG. 8. Baskets 1040 are formed of a woven or stamped mesh 1036 to capture particles of a clot or obstruction.

Figure 31:
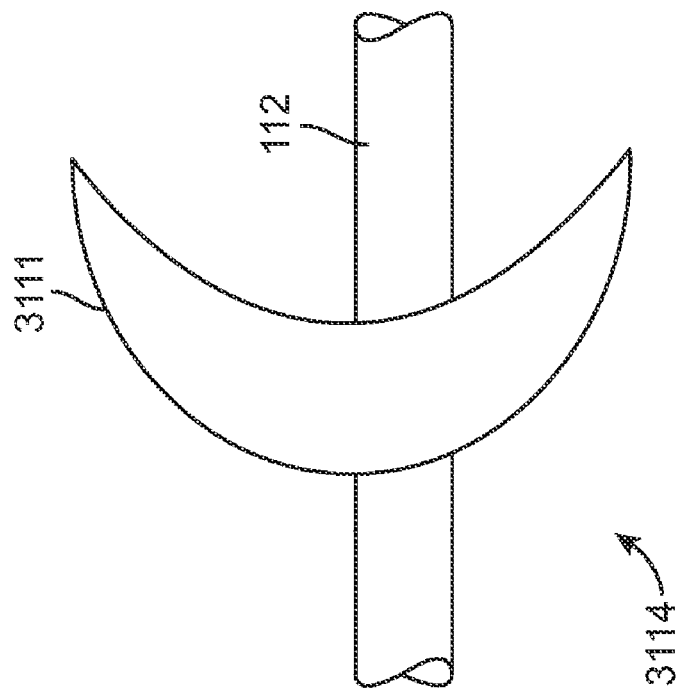
FIG. 31 is a perspective view of a capture device in accordance with another embodiment of the present invention.

In another embodiment illustrated in FIG. 31, capture devices 3114 may be a crescent or scoop shaped basket 3111 fixed to drive belt 112. Baskets 3111 may have an outer diameter similar to that of spherical basket 532 of FIG. 5 or may expand to a greater diameter. Baskets 3111 may be fabricated from a solid piece of material, and/or may include strands or a woven or stamped mesh to capture particles of a clot or obstruction.

Figure 33:
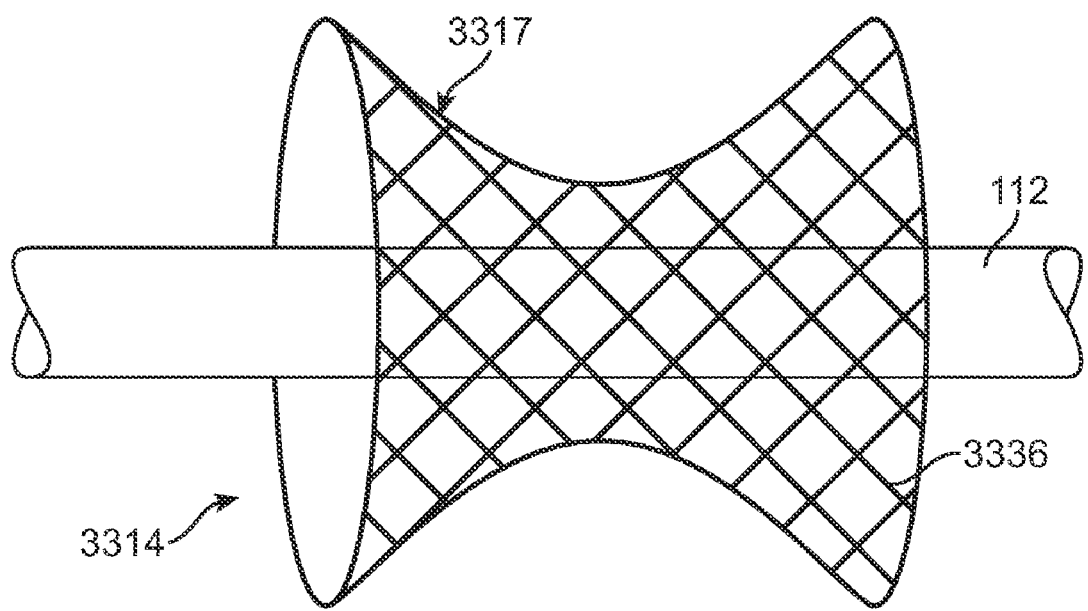
FIG. 33 is a perspective view of a capture device in accordance with another embodiment of the present invention.

In another embodiment illustrated in FIG. 33, capture devices 3314 may be a spool shaped basket 3317 fixed to drive belt 112. Each spool shaped basket 3317 has flared end portions such that the diameter at the center of basket 3317 is smaller than the diameter at the ends of basket 3317. Baskets 3317 may have an outermost diameter similar to that of spherical basket 532 of FIG. 5 or may expand to a greater diameter. Baskets 3317 are formed of a woven or stamped mesh 3336 to capture particles of a clot or obstruction, or may include strands that extend parallel to drive belt 112 and parallel to blood flow when located within the body lumen.

Figure 34:
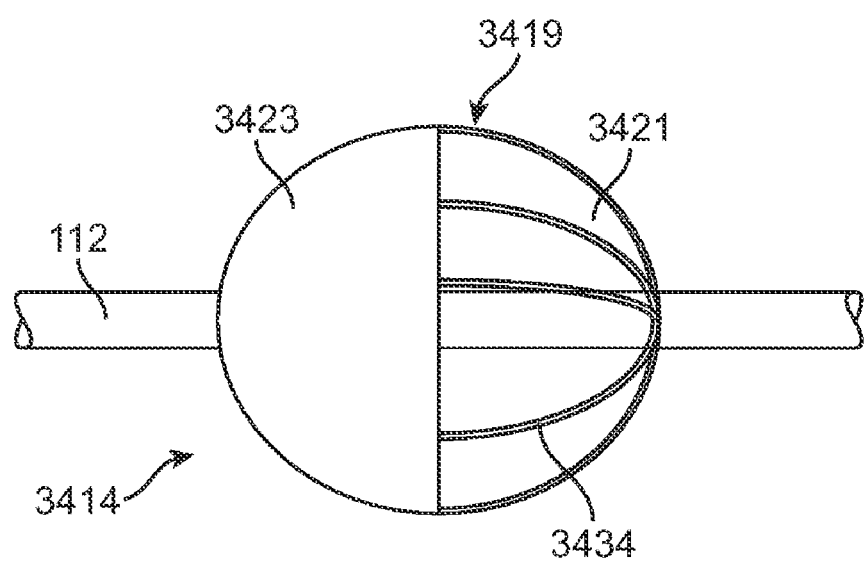
FIG. 34 is a perspective view of a capture device in accordance with another embodiment of the present invention.
Figure 38:
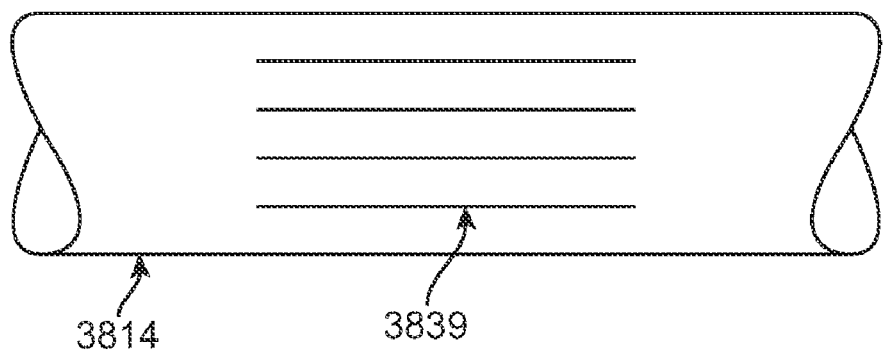
FIG. 38 is a perspective view of a capture device in a straightened or unexpanded configuration in accordance with another embodiment of the present invention.
Figure 39:
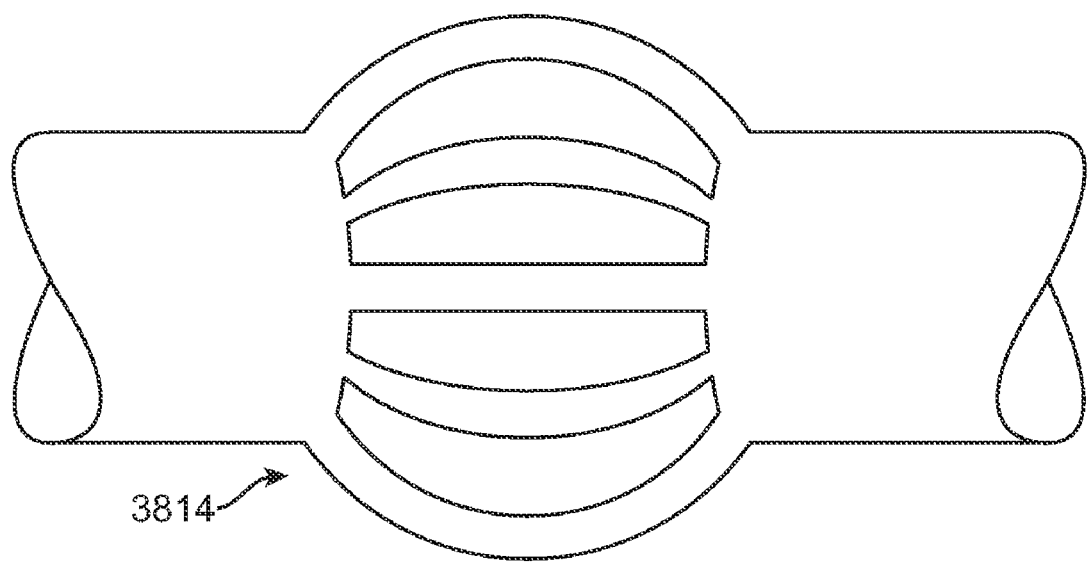
FIG. 39 is a perspective view of the capture device illustrated in FIG. 38 in an expanded configuration.
Figure 40:
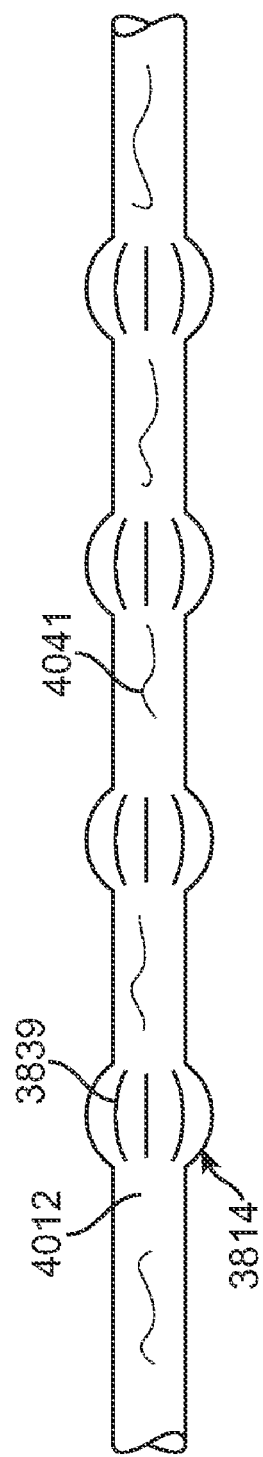
FIG. 40 is a side elevational view of a series of capture devices in accordance with an embodiment of the present invention.

In another embodiment illustrated in FIG. 34, capture devices 3414 may be a spherical basket 3419 fixed to drive belt 112. Baskets 3419 include a closed basket portion 3423 on one half of the spherical structure, and an open filter portion 3421 on the other half of the spherical structure. Baskets 3419 may have an outermost diameter similar to that of spherical basket 532 of FIG. 5 or may expand to a greater diameter. Open filter portion 3421 includes strands 3434 that extend parallel to drive belt 112 and parallel to blood flow when located within the body lumen. Closed basket portion 3423 may be fabricated from a solid piece of material, or may include a woven or stamped mesh to capture particles of a clot or obstruction.

Various embodiments of expandable capture devices according to the present invention are illustrated in FIGS. 38-45B. Illustrated in FIGS. 38-39, capture device 3814 is a tubular segment having parallel slits 3839 that extend longitudinally and are spaced around a circumference thereof. Slits 3839 have a length less than the length of the tubular segment so that when opposing ends of the tubular segment are drawn toward one and other, the tubular segment is compressed such that capture device 3814 radially expands with the strands of material between slits 3839 forming a spherical basket. Capture device 3814 is processed or manufactured so as to remain in the expanded state of FIG. 39. Longitudinal slits 3839 may be laser cut into the tubular segment. The outer diameter of the spherical basket formed by slits 3839 is approximately 0.010 inches to 0.020 inches.

In one embodiment, the tubular segment for forming capture device 3814 may be the drive belt. For example, shown in FIG. 40, capture devices 3814 are formed integrally with drive belt 4012, and made to remain in an expanded state allowing a series of slits 3839 to form a series of spherical baskets therein. Drive belt 4012 may also include a coiled cut 4041 in the straight portion of drive belt 4012 for additional flexibility.

Figure 41:
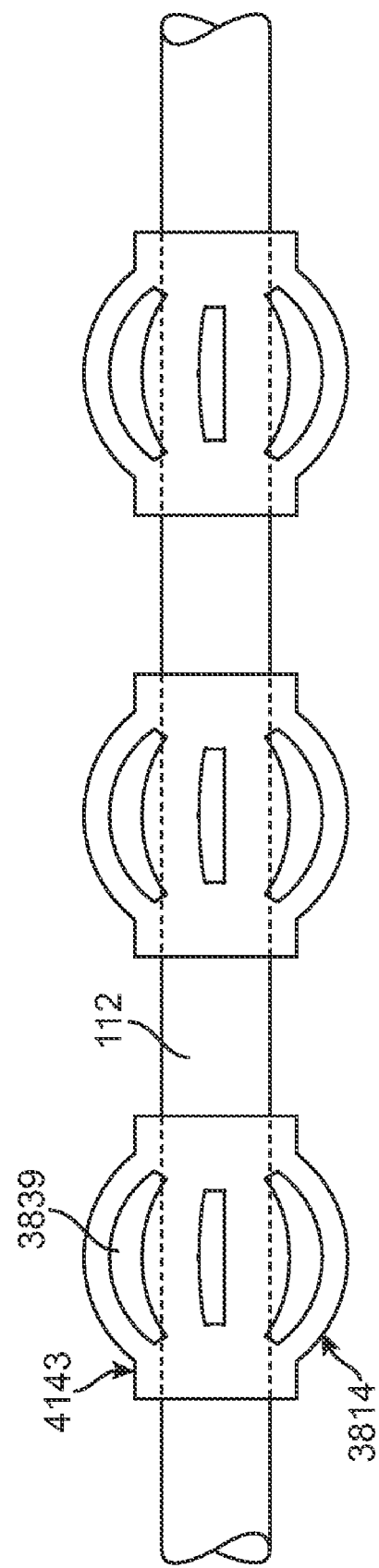
FIG. 41 is a side elevational view of a series of capture devices in accordance with another embodiment of the present invention.

In another embodiment, the tubular segment forms a single capture device 3814 that is attached to the drive belt in an expanded form. For example, as shown in FIG. 41, capture devices 3814 are formed from a tubular segment 4143 when slits 3839 are expanded to form a spherical basket. Tubular segment 4143 is a hollow tube having an inner diameter that is slightly greater than the outer diameter of drive belt 112 so that tubular segment 4143 may be slid over and attached to drive belt 112. Tubular segment 4143 contains one set of longitudinal slits 3839 formed therein. In order to form a plurality of capture devices on drive belt 112, a plurality of spaced apart tubular segments 4143 are positioned in an expanded configuration over drive belt 112.

Figure 42:
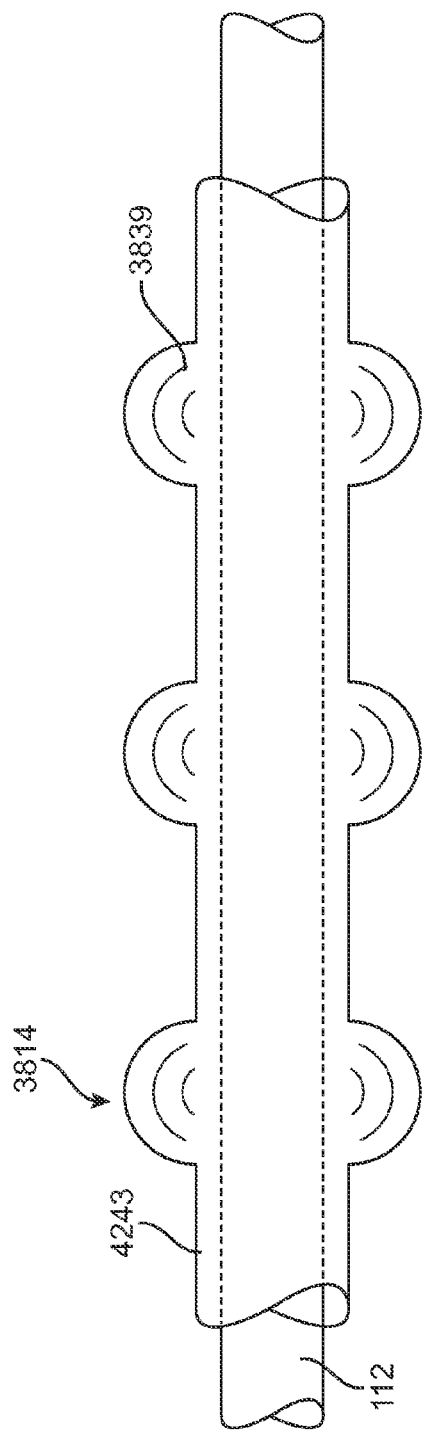
FIG. 42 is a side elevational view of a series of capture devices in accordance with another embodiment of the present invention.
Figure 43:
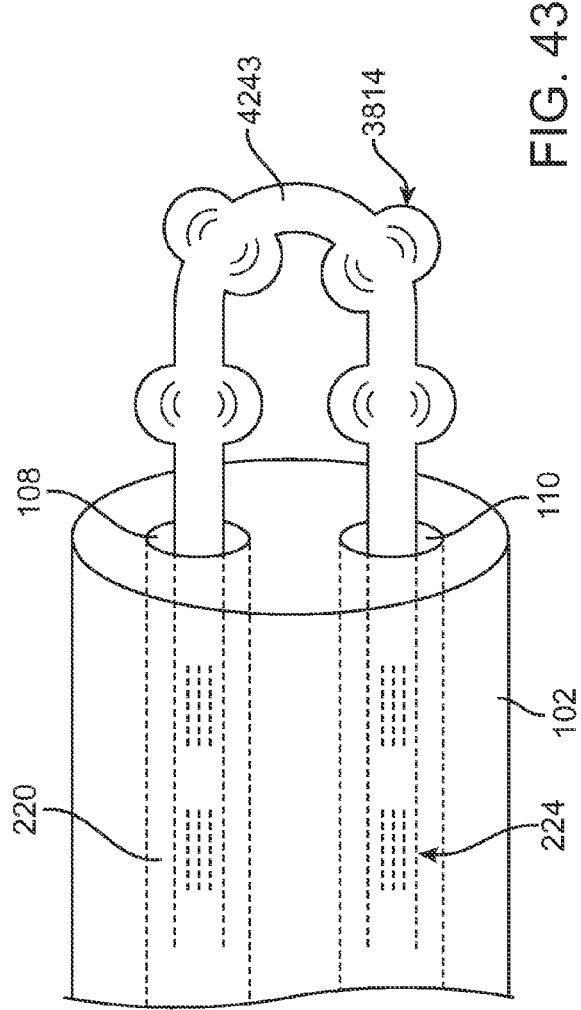
FIG. 43 is an enlarged perspective view of a distal portion of an obstruction removal system in accordance with an embodiment of the present invention.

In yet another embodiment, the tubular segment forms a series of capture devices 3814 and is a separate, continuous tube that is mounted over and/or attached to the drive belt 112. For example, as shown in FIG. 42, a series of capture devices 3814 are formed on a tubular segment 4243. Tubular segment 4243 is slightly longer than drive belt 112 so that when tubular segment 4243 is slid over drive belt 112, compressed and attached to drive belt 112, slits 3839 are compressed and expanded to form spherical baskets. Tubular segment 4243 is a hollow tube having an inner diameter that is slightly greater than the outer diameter of drive belt 112 so that tubular segment 4243 may be slid over and attached to drive belt 112. Tubular segment 4243 contains a plurality of longitudinally spaced sets of slits 3839 formed therein in order to form a plurality of capture devices on drive belt 112.

When either drive belt 4012 or tubular segment 4243 forms capture devices 3814, capture devices 3814 may expand once they exit catheter shaft 102 via distal exit port 108. In one such embodiment illustrated in FIG. 43, catheter shaft 102 surrounds and contains capture devices 3814 in a radially contracted or compressed configuration when the capture devices are located within first lumen 220 of catheter shaft 102 and within second lumen 224 of catheter shaft 102. Traveling in a radially contracted or compressed configuration minimizes the size required for first lumen 220 and second lumen 224, thus minimizing the size of obstruction removal system 100 such that obstruction removal system 100 may fit within relatively small vessels. However, the exposed capture devices 3814 are not contracted by the inner diameters of the catheter lumens between distal exit port 108 and distal reentry port 110. The exposed capture devices 3814 radially expand between distal exit port 108 and distal reentry port 110 so that the strands of material between slits 3839 form a spherical basket.

Figure 44:
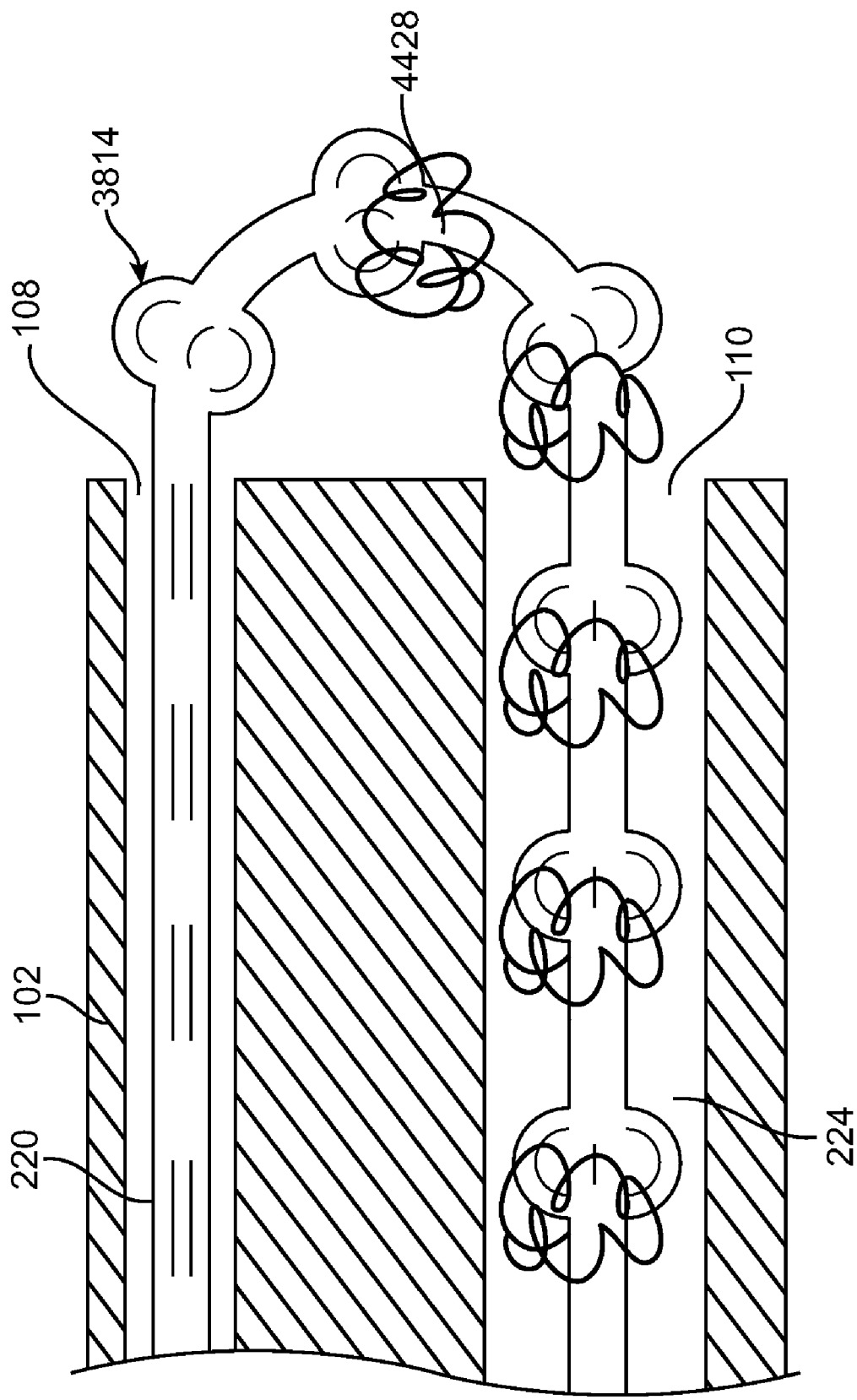
FIG. 44 is a side sectional view of a distal portion of an obstruction removal system in accordance with another embodiment of the present invention.
Figure 45A:
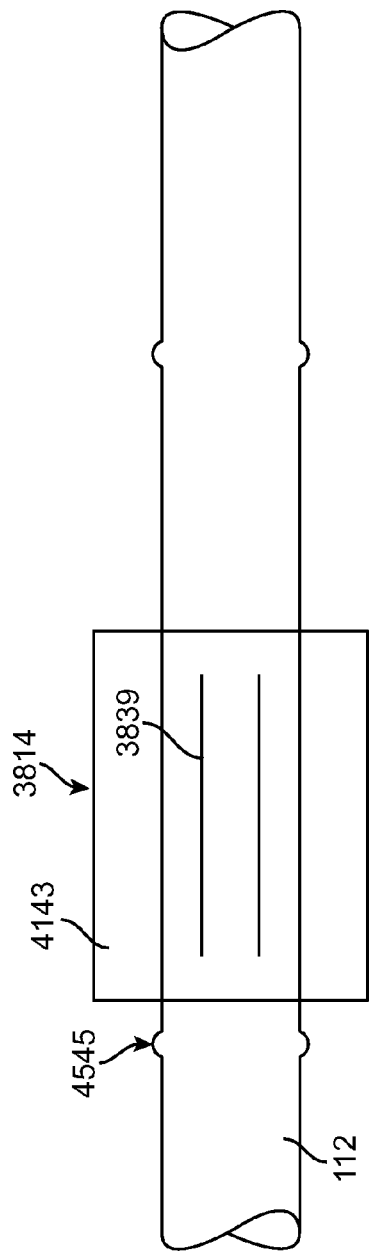
FIG. 45A is a side elevational view of a capture device in a straightened or unexpanded configuration in accordance with an embodiment of the present invention.
Figure 45B:
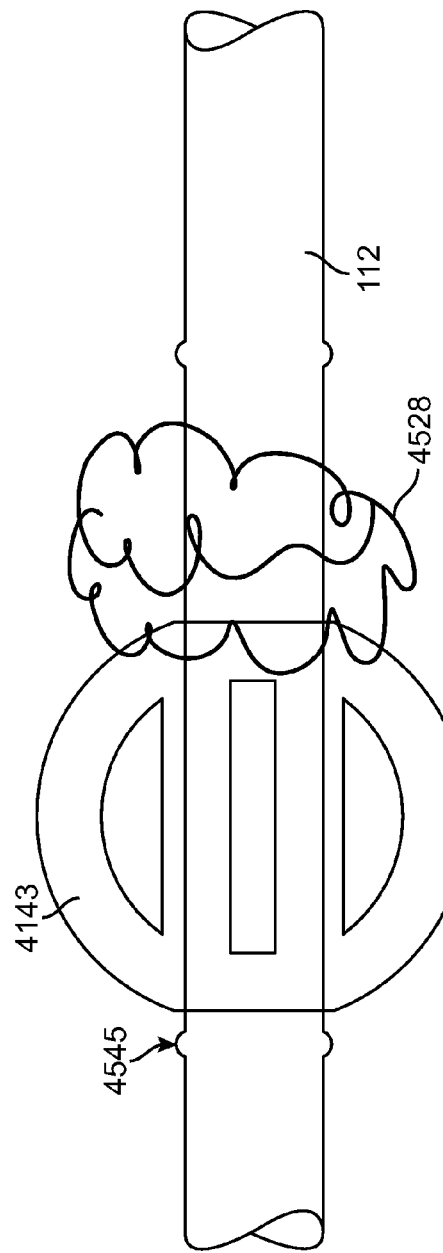
FIG. 45B is a side elevational view of the capture device illustrated in FIG. 45A in an expanded configuration.

In another such embodiment illustrated in FIG. 44, catheter shaft 102 surrounds and contains capture devices 3814 in a radially contracted or compressed configuration when the capture devices are located within first lumen 220 of catheter shaft 102 but capture devices 3814 remain in the expanded configuration when traveling through second lumen 224 of catheter shaft 102. Thus, the size required for first lumen 220 is minimal and thus the overall size of catheter shaft 102 may be reduced and/or the size for a second lumen 224 may be maximized. The exposed capture devices 3814 are not contracted by the inner diameter of first lumen 220 once they exit distal exit port 108. The exposed capture devices 3814 radially expand once they exit distal exit port 108 so that the strands of material between slits 3839 form a spherical basket. Upon re-entry into catheter 102 via a distal reentry port 110, second lumen 224 is of such a size to allow capture devices 3814 to remain in their expanded configuration as they travel through second lumen 224 so that the captured clot particles 4428 are retained in capture devices 3814.

When tubular segment 4143 forms capture device 3814, capture devices 3814 may be loosely fixed on drive belt 112 between two stoppers so that capture device 3814 expands once it encounters a portion of clot or obstruction. Illustrated in FIG. 45A, tubular segment 4143 having one set of slits 3839 formed therein is slid over drive belt 112 and located between two annular stops 4545. The annular stops 4545 are separated from each other a sufficient distance to allow tubular segment 4143 to travel through catheter shaft 102 in a straightened configuration. Traveling in a straightened configuration minimizes the size required for first lumen 220 of catheter shaft 102 as described above with respect to FIG. 44. However, shown in FIG. 45B, compression and subsequent expansion of tubular segment 4143 occurs when segmented tubular segment 4143 encounters a portion of clot or obstruction 4528. The clot material causes capture devices 3814 to radially expand so that the strands of material between slits 3839 form a spherical basket. Upon re-entry into catheter 102 via a distal reentry port 110, capture device 3814 remains in a semi-expanded configuration with the clot particle 4528 captured within the slits 3839 as it travels through second lumen 224 so that the captured clot particles are retained in capture device 3814.

FIGS. 5-10, 31, 33-34, and 38-39 illustrate that the capture devices may be basket or cage-like devices fixed to drive belt 112. The shape of the capture devices may be, for example, cylindrical, spherical, bowl or umbrella shaped, elongated oval shaped (i.e., watermelon-shaped), crescent or scoop shaped, or spool shaped. In each of these embodiments, it will be apparent to those of ordinary skill in the art that portions or particles of a clot or obstruction may be ensnared or caught within the inner area of the capture devices (that is, the captured clot particles are contained within the capture devices). However, it will be apparent to those of ordinary skill in the art that the capture devices may have any suitable configuration that will retrieve the obstruction material in a bit-by-bit or piecemeal fashion.

Figure 11:
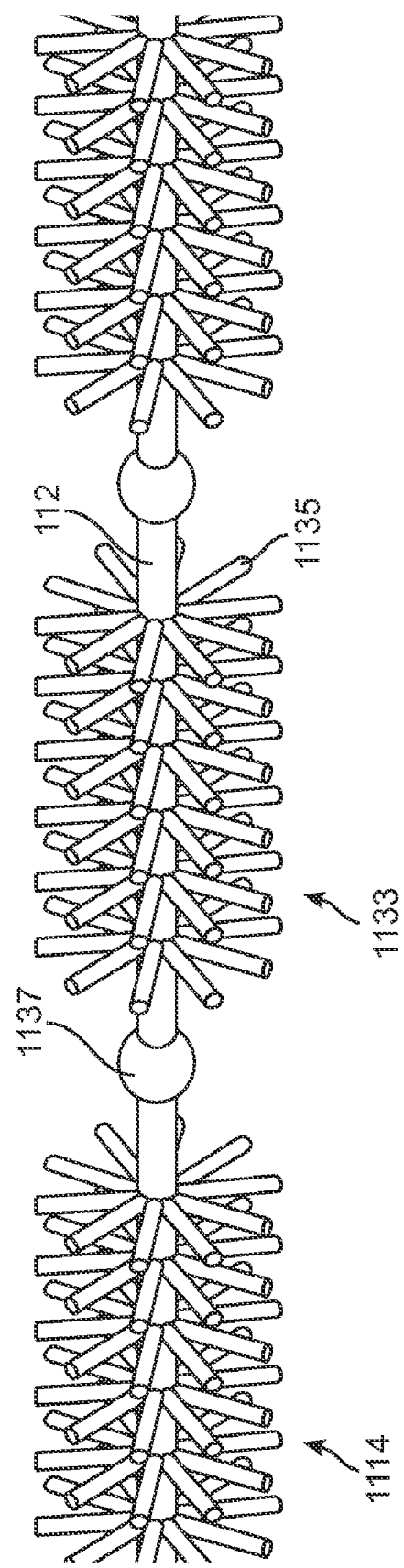
FIG. 11 is a perspective view of a capture device in accordance with another embodiment of the present invention.

Alternatively or in addition, the capture devices may operate as an interference device that detaches or separates portions or particles of a clot or obstruction and then operates to push or pull these detached clot portions or particles into the second lumen of the catheter (that is, the captured clot particles are advanced by the capture devices). For example, in another embodiment of the present invention illustrated in FIG. 11, capture devices 1114 may be a hairbrush-like interference device 1133 fixed to drive belt 112. Hairbrush-like interference device 1133 has an outer diameter that may be similar to that of spherical basket 532 of FIG. 5. Hairbrush-like interference device 1133 includes bristles 1135 that radially extend from drive belt 112 to ensnare or catch a portion of a clot or obstruction. Bristles 1135 may be formed of any suitable material, including but not limited to PEBAX, nylon, polyimide, PEEK, polyethylene terephalate (PET) polyurethane, polyethylene, polypropolyne, stainless steel, nickel titanium, MP35N, and tantalum. As drive belt 112 and hairbrush-like interference device 1133 located thereon pass over a target clot, clot particles are ensnared or caught in bristles 1135. Spaced apart engaging protrusions 1137 may be present between hairbrush-like interference devices 1133 for engaging a pulley of the driving mechanism in order to pull drive belt 112 at a constant speed and for providing room for larger trapped clot particles that may be attached to the drive belt 112. Although shown in conjunction with hairbrush-like interference devices 1133, protrusions 1137 may be utilized between any type of capture devices. Protrusions 1137 will be further explained with reference to FIG. 30 below.

Figure 32:
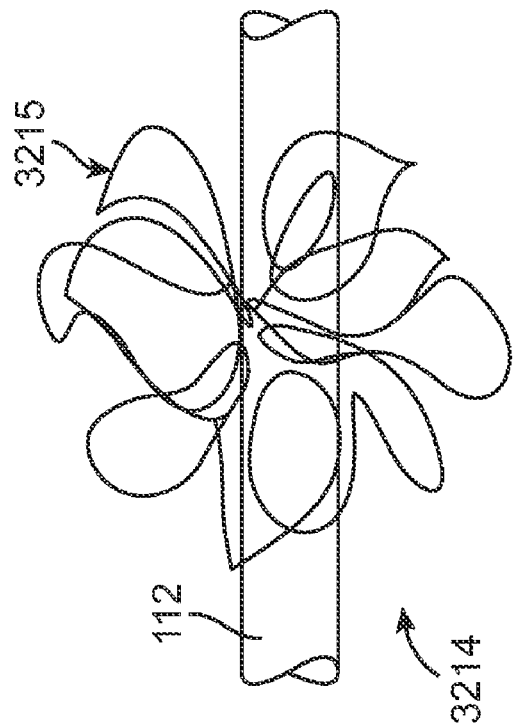
FIG. 32 is a perspective view of a capture device in accordance with another embodiment of the present invention.

In another embodiment of the present invention illustrated in FIG. 32, capture devices 3214 may be a wire-brush interference device 3215 fixed to drive belt 112. Wire-brush interference device 3215 has an outer diameter that may be similar to that of spherical basket 532 of FIG. 5. Wire-brush interference device 3215 includes a plurality of curly strands that extend from drive belt 112 to ensnare or catch a portion of a clot or obstruction. The strands may be formed of any suitable material, including but not limited to stainless steel, nickel titanium, MP35N, tantalum, PEBAX, nylon, polyimide, PEEK, polyethylene terephalate (PET) polyurethane, polyethylene, and polypropylene. As drive belt 112 and wire-brush interference device 3215 located thereon pass over a target clot, clot particles are ensnared or caught in the strands.

In another embodiment of the present invention illustrated in FIG. 35, capture devices 3514 may be a bead-like interference device 3525 fixed to drive belt 112. Bead-like interference device 3525 is a solid polymeric sphere attached to or integral with drive belt 112. The polymeric sphere may be formed of any suitable material, including but not limited to PEBAX, nylon, polyimide, PEEK, polyethylene terephalate (PET) polyurethane, polyethylene, and polypropolyne. Bead-like interference device 3525 has an outer diameter that may be similar to that of spherical basket 532 of FIG. 5 or may have a greater or lesser diameter. The plurality of bead-like interference devices 3525 detach or separate portions or particles of a clot or obstruction and then operate to push or pull these detached clot portions or particles into the second lumen of the catheter. In other words, the captured clot particles are advanced by bead-like interference devices 3525.

In another embodiment of the present invention illustrated in FIG. 36, capture devices 3614 may be a balloon interference device 3629 fixed to drive belt 112. Balloon interference device 3629 is a polymeric balloon attached to or integral with drive belt 112. The polymeric balloon may be formed of any suitable material, including but not limited to PEBAX, nylon, polyethylene terephalate (PET) polyurethane, polyethylene, and polypropolyne. Balloon interference device 3629 has an outer diameter that may be similar to that of spherical basket 532 of FIG. 5 or may have a greater or lesser diameter. The plurality of balloon interference devices 3629 detach or separate portions or particles of a clot or obstruction and then operate to push or pull these detached clot portions or particles into the second lumen of the catheter. In other words, the captured clot particles are advanced by balloon interference devices 3629.

In another embodiment of the present invention illustrated in FIG. 37, capture devices 3714 may be a burr-like interference device 3731 fixed to drive belt 112. Burr-like interference device 3731 is a solid polymeric portion having a jagged, raised and/or an abrasive outer surface for improved cutting into a portion of a clot or obstruction. The polymeric burr may be formed of any suitable material, including but not limited to PEBAX, nylon, polyethylene terephalate (PET) polyurethane, polyethylene, and polypropolyne. Burr-like interference device 3731 has an outer diameter that may be similar to that of spherical basket 532 of FIG. 5 or smaller than that of spherical basket 532 or may have a greater or lesser diameter.

The capture devices illustrated in FIGS. 5-11, 31-34, and 38-42 above may be fabricated from a flexible material that allows the capture devices to deploy or expand upon exiting first lumen 220 of catheter shaft 102 and contract or compress upon re-entry into second lumen 224 of catheter shaft 102. For example, the capture devices may be constructed out of a spring-type or superelastic material such as nickel-titanium (nitinol), a nickel-tin alloy, a shape memory material, and other superelastic materials. In such an embodiment, catheter shaft 102 surrounds and contains at least portion of the capture devices in a contracted or compressed configuration when the capture devices are located within first lumen 220 of catheter shaft 102. Once the capture devices exit catheter shaft 102 via distal exit port 108, the capture devices are released to assume their expanded or deployed configuration. Upon re-entry into catheter shaft 102 via distal reentry port 110, the capture devices resume a contracted or compressed position in order to advance through second lumen 224 of catheter shaft 102. Constructing the capture devices out of a compressible material minimizes the size required for first lumen 220 and second lumen 224, thus minimizing the size of obstruction removal system 100 such that obstruction removal system 100 may fit within relatively small vessels. However, the capture devices may also be formed from a more rigid material. For example, suitable metallic materials include stainless steel, nickel-cobalt alloy such as MP35N, and cobalt-chromium. For increased radiopacity, the capture devices may be formed from or to include tantalum, titanium, platinum, gold, silver, palladium, iridium, and the like. In another embodiment, a wire formed from tantalum, titanium, platinum, gold, silver, palladium, iridium, and the like may be wrapped or coiled about drive belt 112 and/or the capture devices to increase the radiopacity thereof.

Figure 12:
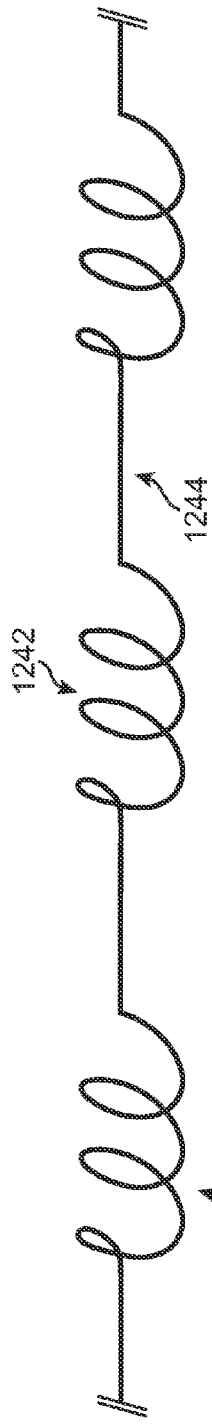
FIG. 12 is a side elevational view of a wire forming a plurality of capture devices in accordance with an embodiment of the present invention.
Figure 13:
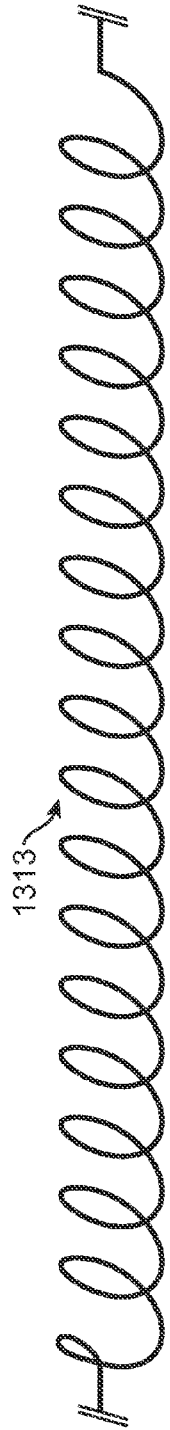
FIG. 13 is a side elevational view of a wire forming a plurality of capture devices in accordance with another embodiment of the present invention.
Figure 14:
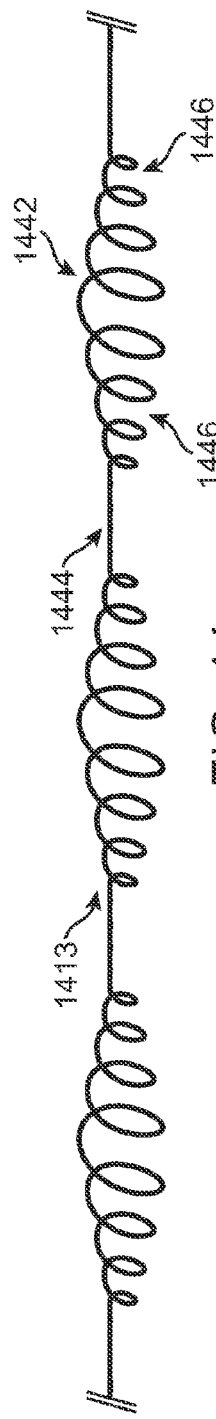
FIG. 14 is a side elevational view of a wire forming a plurality of capture devices in accordance with another embodiment of the present invention.
Figure 15:
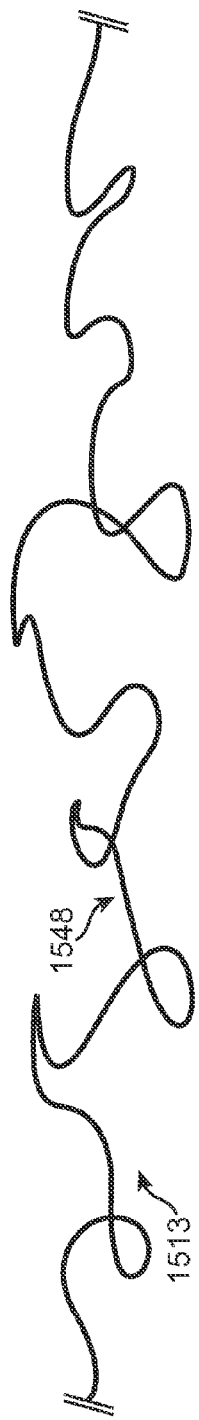
FIG. 15 is a side elevational view of a wire forming a plurality of capture devices in accordance with another embodiment of the present invention.

In another embodiment of the present invention, drive belt 112 and the plurality of capture devices 114 may be an integral or one-piece conveyor or circulating element having integral curly, protuberant, or coiled sections formed by a wire element that also comprises the drive belt. For example, as shown in FIG. 12, conveyor or circulating element 1213 is a wire element having a plurality of "capture devices" formed by integral coiled sections 1242 thereof that are separated by straight sections 1244. In another embodiment shown in FIG. 13, the conveyor or circulating element 1313 is a continuous wire coil element. In another embodiment shown in FIG. 14, conveyor or circulating element 1413 is a wire element having a plurality of "capture devices" formed by integral coiled sections 1442 thereof with straight sections 1444 there between. Coiled sections 1442 have tapered ends 1446 on both sides thereof. In yet another embodiment shown in FIG. 15, conveyor or circulating element 1513 is a wire element having a plurality of "capture devices" formed by integral random protuberant sections 1548 thereof. It will be apparent to those of ordinary skill in the art that when the conveyor or circulating element is a wire, it may be formed into various configurations to form capture devices in addition to those embodiments illustrated in FIGS. 12-15.

The integral conveyor or circulating elements illustrated in FIGS. 12-15 may be constructed out of any appropriate material. For example, suitable metallic materials include stainless steel, nickel-cobalt alloy such as MP35N, and cobalt-chromium. For increased radiopacity, the integral conveyor or circulating elements may be constructed from or to include tantalum, titanium, platinum, gold, silver, palladium, iridium, and the like. In another embodiment, a wire formed from tantalum, titanium, platinum, gold, silver, palladium, iridium, and the like may be wrapped or coiled about the integral conveyor or circulating elements to increase the radiopacity thereof.

In another embodiment, the integral conveyor or circulating elements may be constructed out of a spring-type or superelastic material such as nickel-titanium (nitinol), a nickel-tin alloy, a shape memory material, and other superelastic materials. Deployment of the capture devices may be effected by utilizing the superelastic or shape memory characteristics of a material. More particularly, the integral conveyor or circulating elements may have two states of size or shape, a straightened configuration sufficient for delivery to the treatment site and a deployed or expanded configuration forming the capture devices in order to capture or retrieve a portion of a clot or obstruction at the treatment site. In one embodiment, the deployed or expanded configuration of the integral conveyor or circulating elements may be achieved by utilizing elastic or superelastic characteristics of a material. The integral conveyor or circulating elements may be mechanically deformed into the straightened configuration when located within the first lumen of the catheter. Once the integral conveyor or circulating elements exit the catheter via the distal exit port, the integral conveyor or circulating elements elastically retain their shape and thus assume their expanded or deployed configuration. In another embodiment, the deployed or expanded configuration of the integral conveyor or circulating elements may be achieved by utilizing temperature-dependent characteristics of a material. More particularly, some shape memory metals have the ability to return to a defined shape or size when subjected to certain thermal or stress conditions. Shape memory metals are generally capable of being deformed at a relatively low temperature and, upon exposure to a relatively higher temperature, return to the defined shape or size they held prior to the deformation. The integral conveyor or circulating elements may be deformed into the straightened configuration when located within the first lumen of the catheter. Once the integral conveyor or circulating elements exit the catheter via the distal exit port, the integral conveyor or circulating elements may assume their "remembered" deployed or expanded configuration once exposed to a higher temperature, i.e., body temperature, in vivo.

Figure 16:
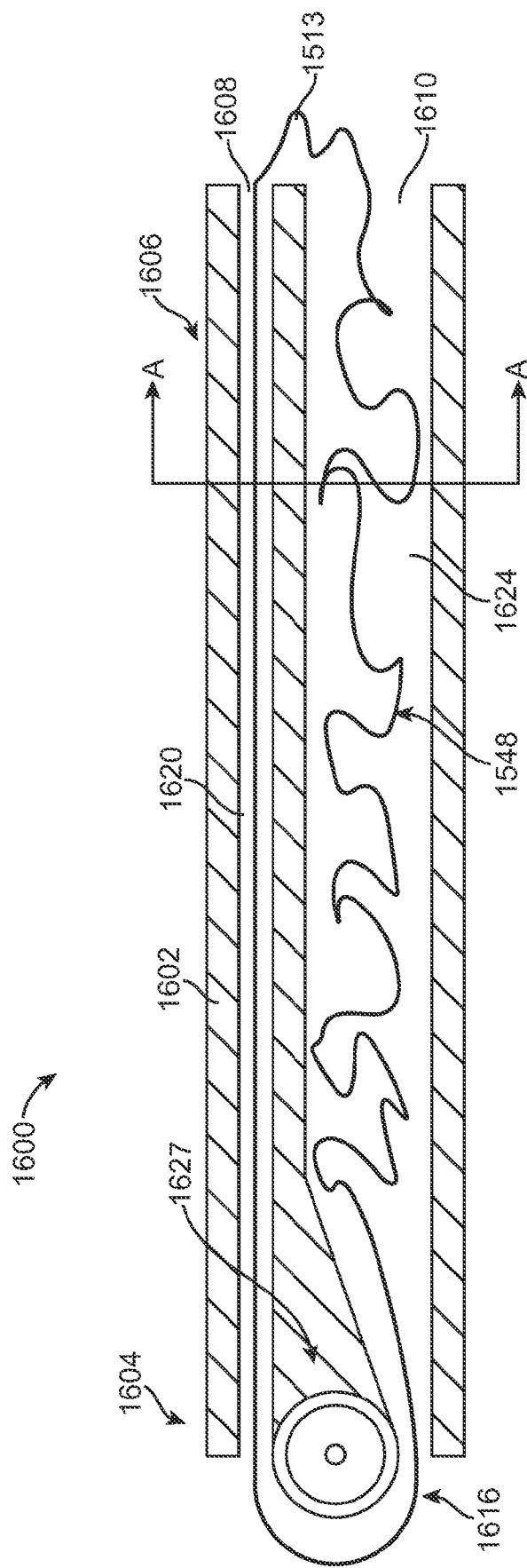
FIG. 16 is a sectional view of an obstruction removal system in accordance with another embodiment of the present invention.
Figure 16A:
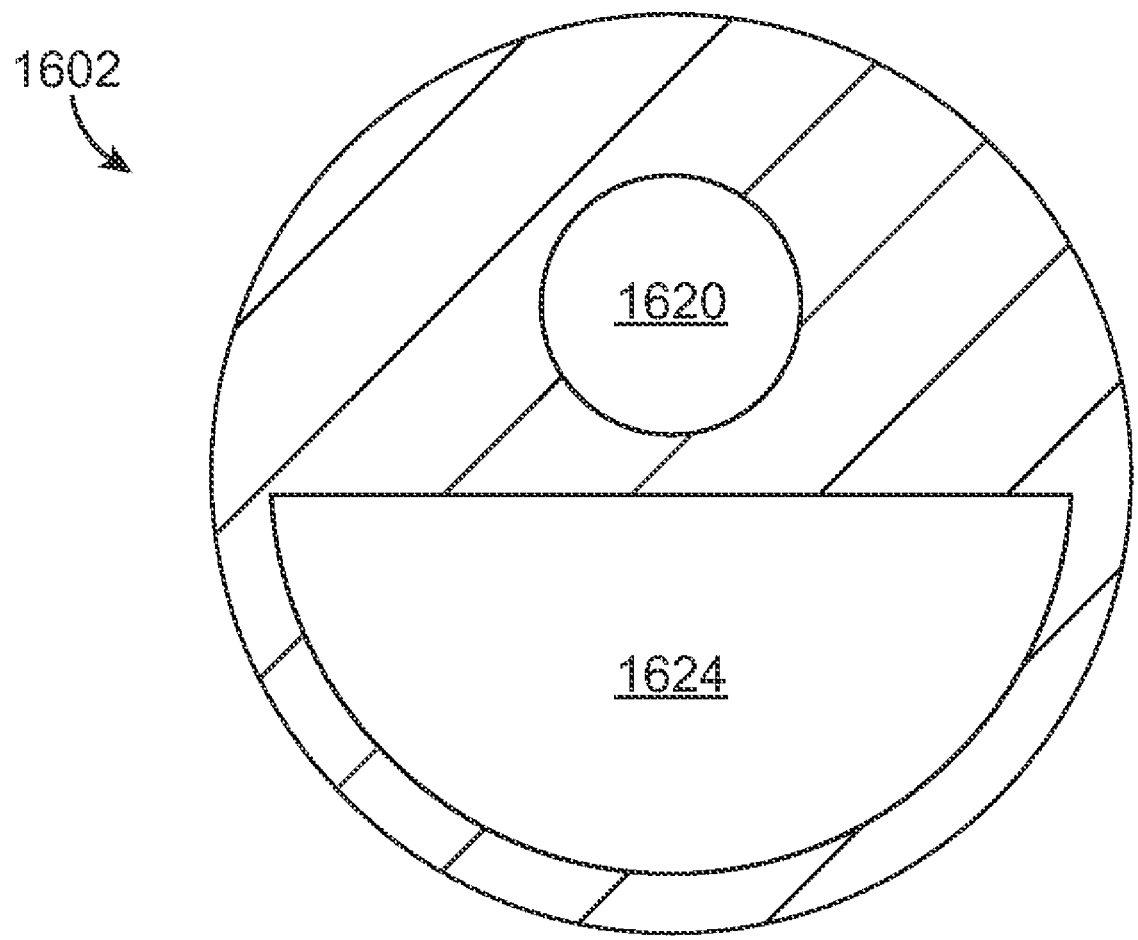
FIG. 16A is a cross-sectional view of the obstruction removal system taken along line A-A of FIG. 16.

The advantages of utilizing a superelastic or shape memory material for the integral conveyor or circulating elements are illustrated in FIGS. 16-16A. FIG. 16 is a sectional view of a obstruction removal system 1600 in accordance with another embodiment of the present invention, while FIG. 16A is a cross-sectional view taken along line A-A of FIG. 16. Similar to the embodiment depicted in FIG. 15, integral conveyor or circulating element 1513 is a wire element with a plurality of capture devices comprised of integral random protuberant sections 1548 formed therein. Integral conveyor or circulating element 1513 is formed of a material having superelastic or shape memory characteristics as described above. The superelastic or shape memory characteristics enable conveyor or circulating element 1513 to travel in a deformed, straightened state within a first lumen 1620 of catheter 1602. Thus, the size required for first lumen 1620 is minimal and thus the overall size of catheter 1602 may be reduced and/or the size for a second lumen 1624 may be maximized. When conveyor or circulating element 1513 exits a distal portion 1606 of catheter 1602 via a distal exit port 1608, protuberant capture devices 1548 may assume their "remembered" deployed or expanded configuration. Upon re-entry into catheter 1602 via a distal reentry port 1610, conveyor or circulating element 1513 remains in its protuberant configuration as it travels through second lumen 1624 so that the captured clot particles are retained in capture devices 1548. In order to ensure that loose clot particles do not migrate downstream, the second lumen 1624 may contain a negative pressure or vacuum for pulling the captured clot particles proximally as described herein with respect to FIG. 46 and/or FIG. 30. The negative pressure or vacuum keeps second lumen 1624 free from clot particles that may dislodge during the circulation of conveyor or circulating element 1513 through second lumen 1624, thus keeping second lumen 1624 clear of debris or self-cleaning. Further, the negative pressure at the distal reentry port 1610 of second lumen 1624 may pull the clot towards conveyor or circulating element 1513 thus facilitating the retrieval of a small portion of the clot or obstruction in order to remove the source of vascular occlusion in a bit-by-bit or piecemeal fashion. At a proximal end 1604 of catheter 1602, catheter 1602 includes a transition section 1627 for transitioning conveyor or circulating element 1513 from second lumen 1624 into a drive mechanism 1616. Transition section 1627 has a tapered shape in order to funnel conveyor or circulating element 1513 from second lumen 1624 into drive mechanism 1616. Although FIGS. 16-16A have been described utilizing conveyor or circulating element 1513 with integral random protuberant or curly sections 1548 formed therein, it will be apparent to those skilled in the art that the conveyor or circulating element may have other deployed or expanded configurations such as those described above with respect to FIGS. 12-14. For example, the conveyor or circulating element may assume a "remembered" continuous or periodic coiled shape once it exits catheter 1602 via distal exit port 1608.

As shown above, the plurality of capture devices may assume various forms. For example, the plurality of capture or interference devices may be basket or cage-like devices fixed to the drive belt that operate to catch portions or particles of a clot or obstruction within the inner area of the capture devices (that is, contained within the capture devices). In other embodiments, the plurality of capture devices may operate as interference devices that detach or separate portions or particles of a clot or obstruction and then operate to push or pull these detached clot portions or particles into the second lumen of the catheter (that is, the captured clot particles are advanced by the capture devices). In yet another embodiment, the plurality of capture devices may be formed by integral curly, protuberant, or coiled sections of a conveyor or circulating element that operate to contain and/or advance portions or particles of a clot or obstruction. "Captured" clot or obstruction particles as used herein is intended to refer to both scenarios, i.e., particles contained within the capture devices and particles advanced by the capture devices.

As previously stated, the geometry and size of the capture or interference devices may be varied to optimize the clot or obstruction retrieval. In addition, the number of such devices and the spacing between adjacent devices may also be varied to optimize the clot or obstruction retrieval. For example, the spacing between adjacent capture devices may be regular or evenly-spaced along the length of the drive belt or may be irregular or unevenly-spaced along the length of the drive belt. In addition, the plurality of capture devices may extend along the entire length of the drive belt, or may extend along only portion of the drive belt.

Drive Mechanisms

Embodiments of the obstruction removal system of the present invention may include one or more drive mechanisms on its proximal end for driving the drive belt and capture devices located thereon through the multi-lumen catheter. A drive mechanism operates to essentially pull the plurality of capture devices through the first lumen of the catheter such that they exit the catheter via a distal exit port and pull the plurality of capture devices, having captured clot particles therein, through a second lumen of the catheter via distal reentry port. The plurality of capture devices operate in a circulating or conveyor-like manner, meaning that the drive mechanism continuously moves and advances the capture devices through a circuit defined by the lumens of the catheter. After a series of passes, the plurality of capture devices collectively removes the entire source of the vascular occlusion.

In one embodiment, the drive mechanism may be a mechanical pulley system manually operated by the device operator which advances drive belt 112 and the capture devices located thereon through catheter shaft 102 in a circulating manner. Referring to FIGS. 17A-17B, drive mechanism 1716 is a pulley system located within a housing 1750 located at proximal end 104 of catheter shaft 102. Housing 1750 also houses a guide or divider 1759 which guides drive belt 112 from catheter shaft 102 to a first pulley 1754. A knob 1751 having a handle 1752 thereon is located outside housing 1750 such that an operator may manually control the pulley system. Knob 1751 has a centrally located hole 1753 which receives and is joined to a connector shaft 1756 extending from first pulley 1754. When an operator turns knob 1751 in a first direction via handle 1752, first pulley 1754 also turns in the first direction since first pulley 1754 is fixedly connected to knob 1751 via connector shaft 1756. By turning knob 1751, first pulley 1754 thus drives drive belt 112 and the capture devices located thereon through catheter shaft 102 in a circulating manner.

Figure 29:
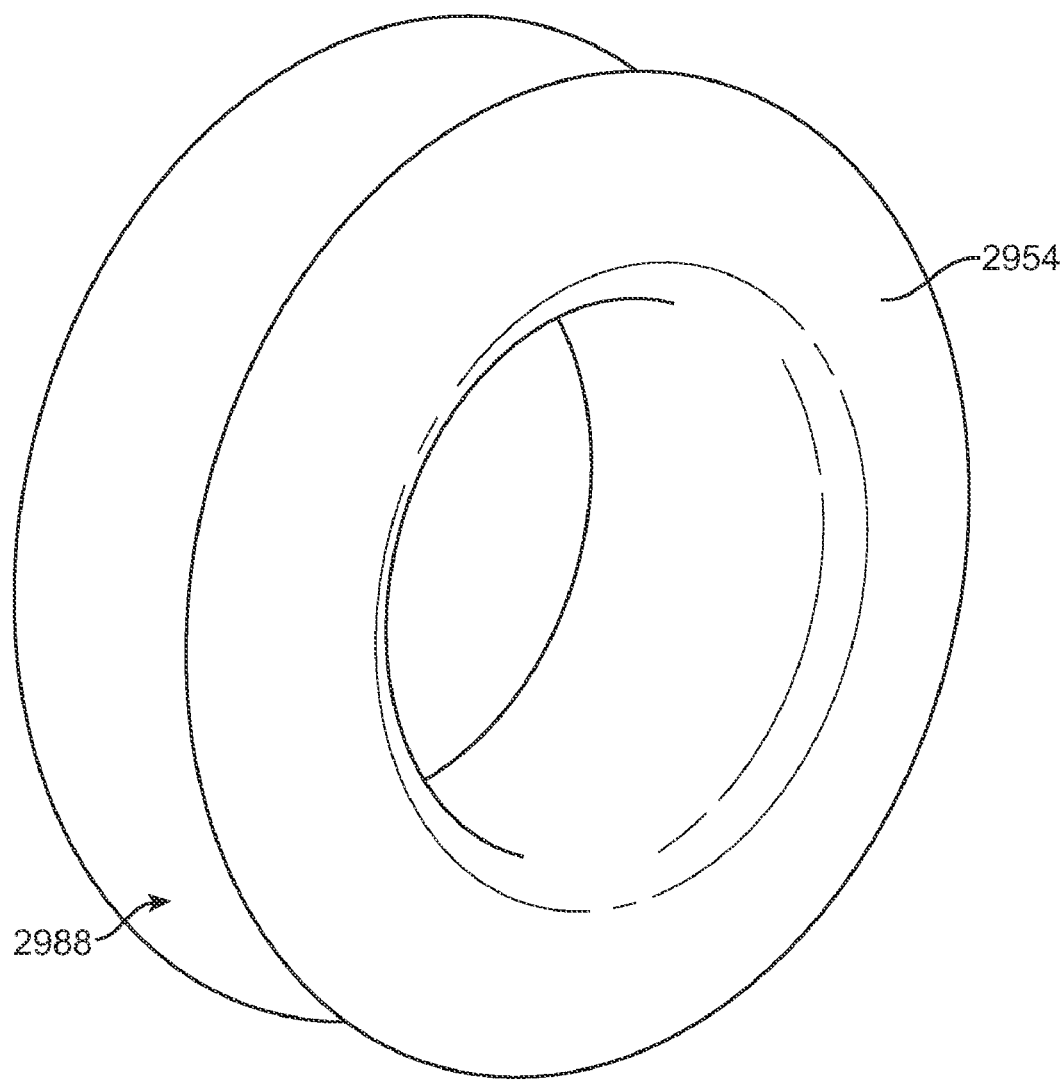
FIG. 29 is a perspective view of a pulley utilized in an obstruction removal system in accordance with another embodiment of the present invention.

In one embodiment of the present invention, the first pulley may be modified to accommodate three-dimensional capture devices affixed to drive belt 112. For example, referring now to FIG. 29, a first pulley 2954 may include a groove 2988 formed therein in order to accommodate three-dimensional capture devices affixed to drive belt 112. The capture devices may be basket or cage-like devices fixed to drive belt 112 as illustrated in FIGS. 5-10, 31, 33-34, and 38-39. Alternatively, the capture devices may be interference devices fixed to drive belt 112 as illustrated in FIGS. 11, 32, and 35-37. These three-dimensional capture devices may be formed of a compressible material as described above, and thus may compress in size when they are passed through the pulley system. Groove 2988 of first pulley 2954 will be of sufficient size to allow the three-dimensional capture devices to pass through the pulley system and thus circulate through catheter shaft 102.

Figure 47:
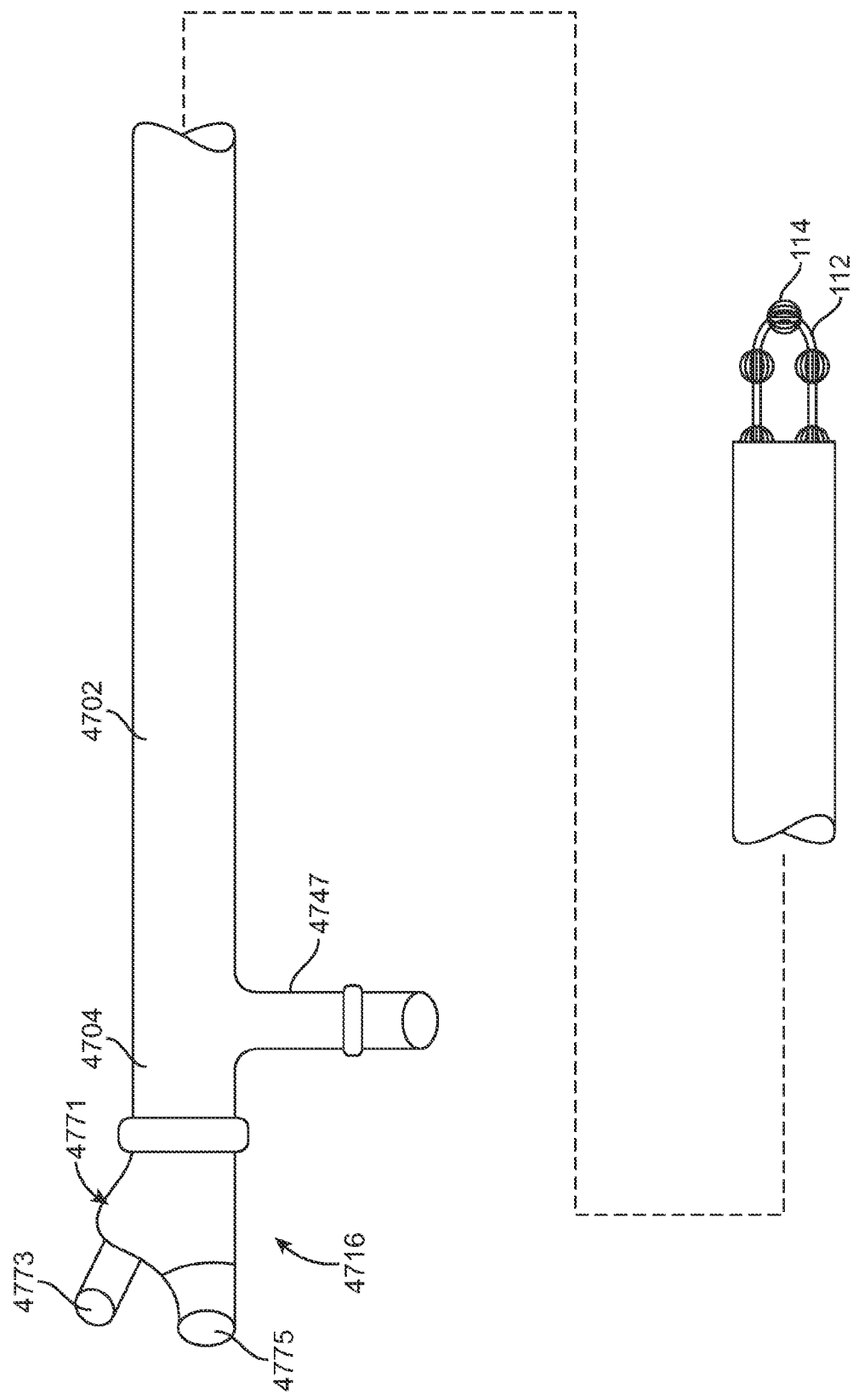
FIG. 47 is a side elevational view of an obstruction removal system in accordance with another embodiment of the present invention.
Figure 48:
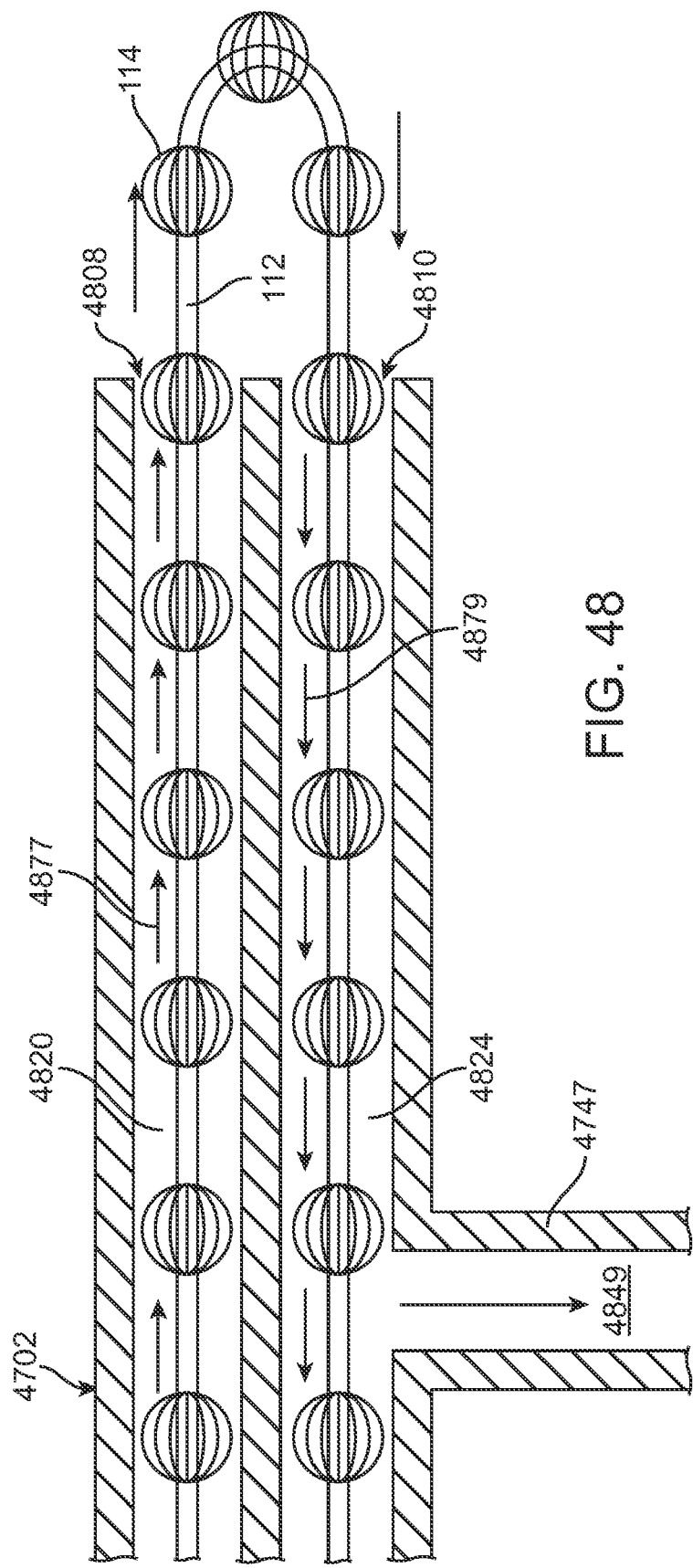
FIG. 48 is a side sectional view of the distal portion of the obstruction removal system illustrated in FIG. 47.

In another embodiment, the drive mechanism may be an aspiration or vacuum source and/or a pressurization source at the proximal end of the obstruction removal system in order to advance drive belt 112 and the capture devices located thereon through catheter shaft 102 in a circulating manner. Referring to FIGS. 47-48, drive mechanism 4716 includes a hub 4771 located at the proximal end 4704 of catheter shaft 4702. Hub 4771 includes a pressure port 4773 for receiving a source of pressurization and a vacuum port 4775 for receiving a vacuum source. Catheter shaft 4702 may also include a vacuum shaft 4747 forming a clot particle reservoir 4849 therein adjacent to proximal end 4704 of catheter shaft 4702. Clot particle reservoir 4849 is in fluid communication with second lumen 4824 of catheter shaft 4702. A source of pressurization connected via pressure port 4773 pushes capture devices 114 through first lumen 4820 and distal exit port 4808 of catheter shaft 4702 as shown by directional arrows 4877 on FIG. 48. In the alternative or in addition to, a vacuum source connected via vacuum port 4775 pulls capture devices 114 through second lumen 4824 of catheter shaft 4702 as shown by directional arrows 4879 on FIG. 48. The vacuum source also provides a suction force along second lumen 4824 for pulling the captured clot particles proximally into clot particle reservoir 4849. As such, the vacuum source keeps second lumen 4824 free from clot particles that may dislodge from capture devices 114 as they travel through second lumen 4824, thus keeping second lumen 4824 clear of debris or self-cleaning. Further, the vacuum source creates a negative pressure at the distal reentry port 4810 of second lumen 4824 and thus may pull clot material towards capture devices 114 thus facilitating the retrieval of a small portion of the clot or obstruction in order to remove the source of vascular occlusion. The vacuum source may be any system capable of providing a negative pressure or suction force.

Figure 49:
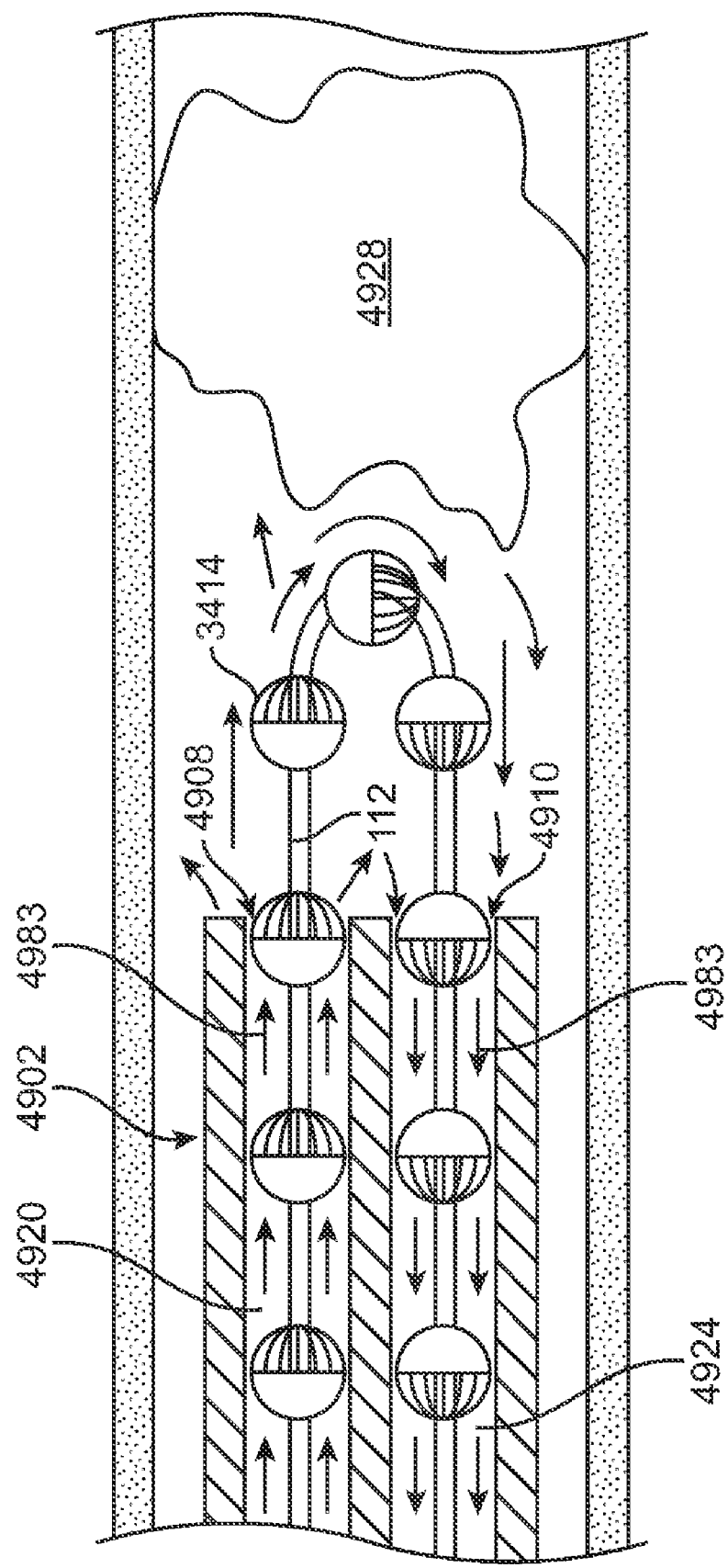
FIG. 49 is a side sectional view of a distal portion of an obstruction removal system in accordance with another embodiment of the present invention.

The source of pressurization may be any system capable of providing a pressure force, and may, for example, be accomplished utilizing a fluid such as saline as shown in FIG. 49. The fluid may aid in the breakdown of the clot or obstruction 4928 in addition to the mechanical breakdown provided by the capture devices. The fluid flow pushes capture devices 3414 through first lumen 4920, distal exit port 4908, distal re-entry port 4910, and second lumen 4924 of catheter shaft 4902 as shown by directional arrows 4983 on FIG. 49 in order to advance drive belt 112 and the capture devices located thereon through catheter shaft 4902 in a circulating manner. Although FIG. 49 has been described utilizing capture devices 3414 described above in relation to FIG. 34, it will be apparent to those skilled in the art that the use of a fluid may be utilized with any embodiment described herein.

Figure 20B:
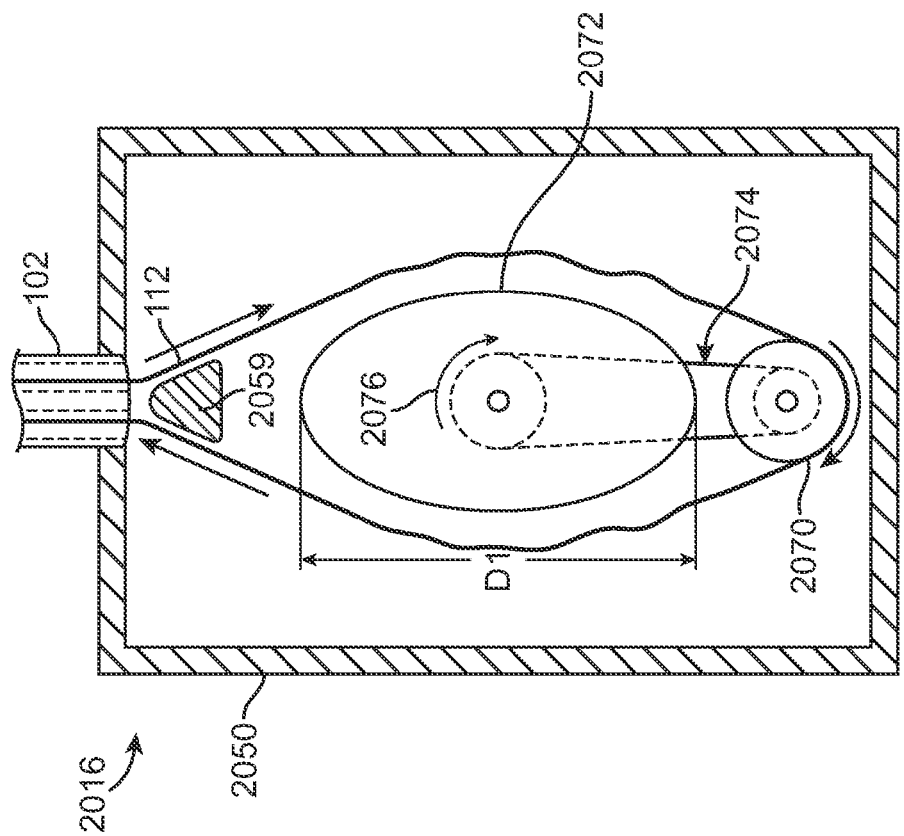
FIG. 20B is another sectional view of the proximal portion of an obstruction removal system illustrated in FIG. 20A.
Figure 20A:
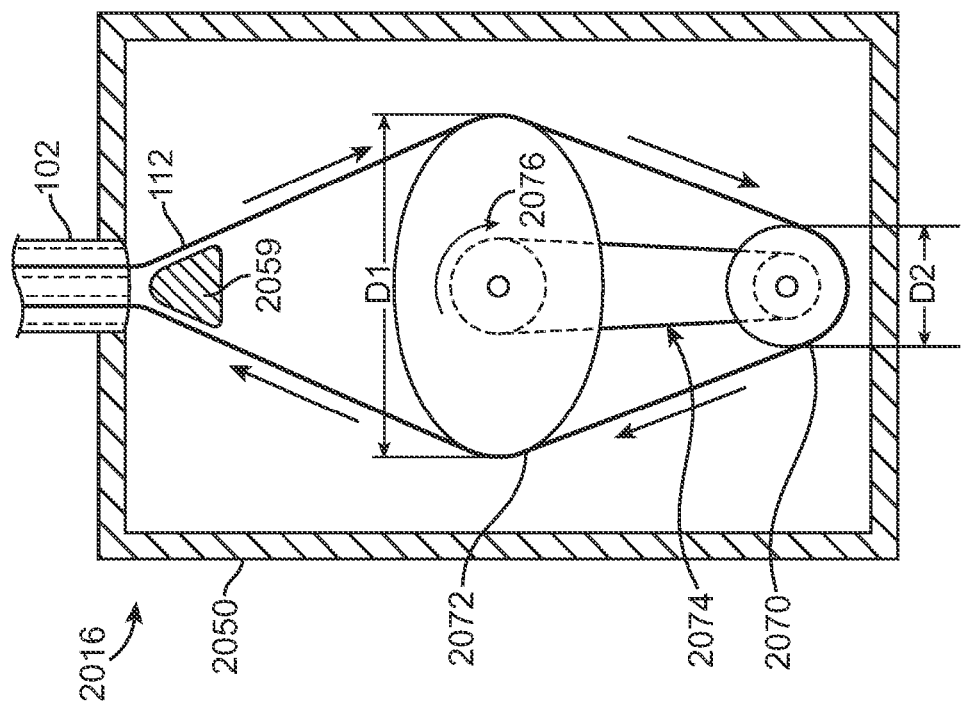
FIG. 20A is a sectional view of a proximal portion of an obstruction removal system in accordance with another embodiment of the present invention.

In another embodiment of the present invention, the drive mechanism may be a mechanical double-pulley system manually operated by the device operator which advances drive belt 112 and the capture devices located thereon through catheter shaft 102 in a circulating manner. The double-pulley drive mechanism may include a loosening mechanism that operates similar to a cam device in order to create slack in the drive belt, which may aid in capturing or interfering with the clot or obstruction. More particularly, FIGS. 20A-20B illustrate a drive mechanism 2016 including a first pulley 2070 and a second pulley 2072 within a housing 2050 located at proximal end 104 of catheter shaft 102. Housing 2050 also houses a guide or divider 2059, which guides drive belt 112 from catheter shaft 102 to the mechanical double-pulley system. A knob (not shown) is located outside housing 2050 such that an operator may manually control the double-pulley system. The knob is connected to second pulley 2072. When an operator turns the knob in a first direction indicated by directional arrow 2076, second pulley 2072 also turns in the first direction since second pulley 2072 is fixedly connected to the knob. A belt 2074 passes between first pulley 2070 and second pulley 2072 in order to transmit the rotational motion created by the knob from second pulley 2072 to first pulley 2070. By turning the knob, second pulley 2072 causes first pulley 2070 to also rotate in the first direction via belt 2074. When first pulley 2070 rotates in the first direction, first pulley 2070 drives drive belt 112 and the capture devices located thereon through catheter shaft 102 in a circulating manner.

Second pulley 2072 is an oblong shape, meaning that its diameter D1 is elongated in one direction. First pulley 2070 is a circular shape having a diameter D2. As apparent from FIG. 20A, diameter D2 of first pulley 2070 is less than elongated diameter D1 of second pulley 2072. When second pulley 2072 is turned or rotated as described above, the oblong shape of second pulley 2072 creates slack in drive belt 112. Drive belt 112 is taut over second pulley 2072 when drive belt 112 contacts elongated diameter D1 of second pulley 2072 during its rotation as shown in FIG. 20A. However, drive belt 112 is loose, i.e., slack in drive belt 112 is created, when second pulley 2072 rotates such that drive belt 112 does not contact elongated diameter D1 of second pulley 2072 as shown in FIG. 20B. When drive belt 112 and the plurality of capture devices 114 is an integral or one-piece conveyor or circulating element having integral curly, protuberant, or coiled sections formed by a wire element that also comprises the drive belt as described above in relation to FIGS. 12-15, the looseness or slack created in the integral or one-piece conveyor may improve the ability of the capture devices to capture or interfere with the clot or obstruction. Since the slack releases tension in the integral or one-piece conveyor, the slack allows recoil of the wire element in order to form the capture devices for effective clot capture. The mechanical double-pulley system of FIGS. 20A-20B may utilize any of cleaning mechanisms described herein to clean captured clot particles from the drive belt and the capture devices located thereon as they pass through the proximal end of the obstruction removal system.

Figure 50:
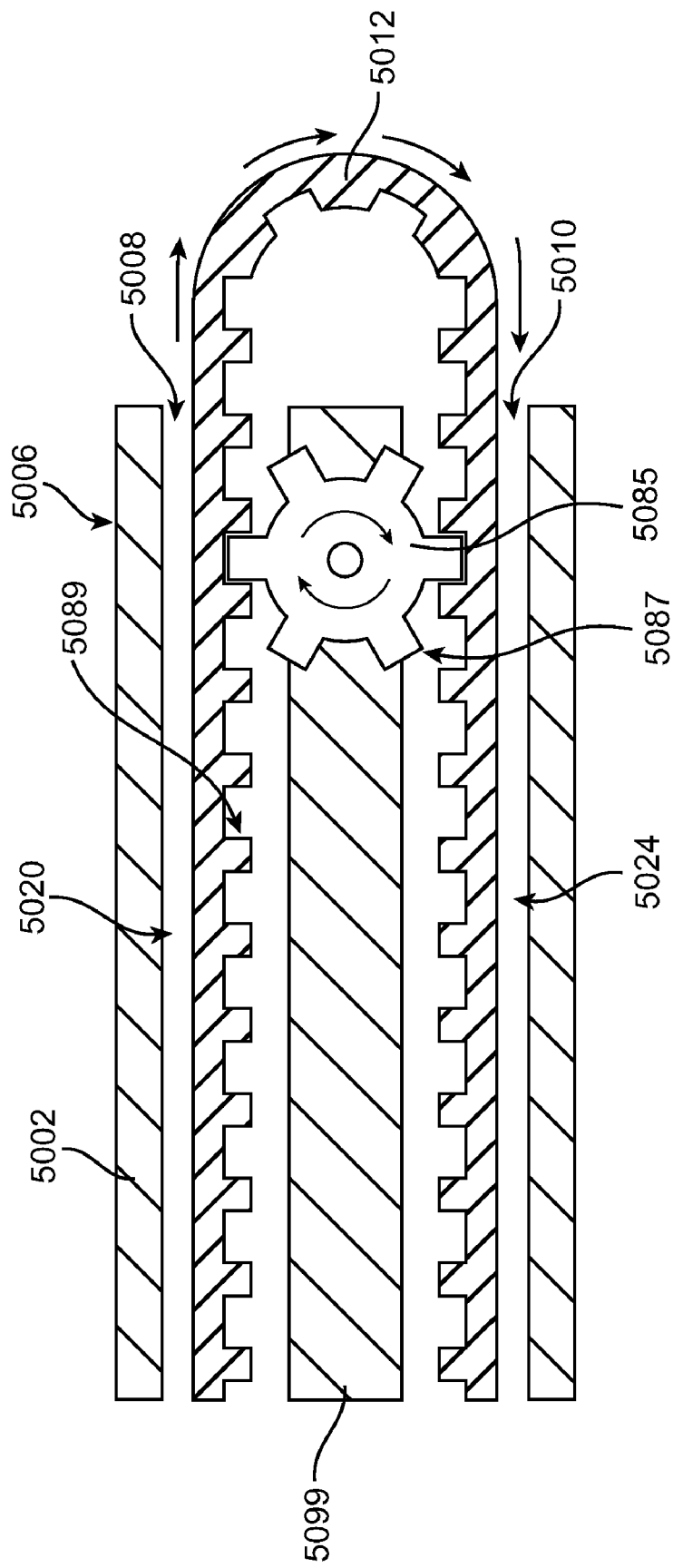
FIG. 50 is a side sectional view of a distal portion of an obstruction removal system in accordance with another embodiment of the present invention.

In another embodiment of the present invention, a loosening mechanism may be utilized within the catheter shaft at the distal end thereof in order to create a pre-defined amount of slack in the drive belt, which may aid in capturing or interfering with the clot or obstruction. More particularly, FIG. 50 is a side sectional view of a distal portion 5006 of a catheter shaft 5002 in accordance with another embodiment of the present invention. FIG. 50 illustrates a drive belt 5012 circulating through a first lumen 5020 of catheter shaft 5002, exiting out of distal exit port 5008, returning into catheter shaft 5002 via distal re-entry port 5010, and through a second lumen 5024 of catheter shaft 5002. Drive belt 5012 is illustrated in FIG. 50 without a plurality of capture devices thereon for sake of clarity, but it is to be understood that drive belt 5012 carries a plurality of capture devices as described herein through catheter shaft 5002 in a circulating manner. A gear 5085 is located within catheter shaft 5002 on a middle portion 5099 of catheter shaft 5002. Middle portion 5099 of catheter shaft 5002 is located between first lumen 5020 and second lumen 5024 of catheter shaft 5002. Gear 5085 includes protrusions or teeth 5087 and drive belt 5012 includes mating protrusions or teeth 5089. Teeth 5087 of gear 5085 are of such form, size, and spacing that they mesh or cooperate with teeth 5089 of drive belt 5012. Due to the incremental spacing of teeth 5087, gear 5085 provides a means of moving drive belt 5012 in such a way that the exposed portion of drive belt 5012 (the portion of drive belt 5012 extending outside of catheter shaft 102 between distal exit port 5008 and distal reentry port 5010) has a pre-defined amount of slack. The looseness or slack created in drive belt 5012 may improve the ability of the capture devices to capture or interfere with the clot or obstruction. Since the slack releases tension in the exposed portion of drive belt 5012, the slack allows recoil of drive belt 5012 for effective clot capture. A pulley system, such as for example that shown in FIGS. 17A-17B described above, may be utilized at the proximal end of catheter shaft 5002 for advancing drive belt 5012 through catheter shaft 5002 in a circulating manner. When such a pulley system is utilized, the portion of drive belt 5012 located within second lumen 5024 is under tension (the active side of the loop) while the portion of drive belt 5012 located within first lumen 5020 is not under tension (the passive side of the loop). Operating the pulley system causes the portion of drive belt 5012 located within first lumen 5020 to advance through first lumen 5020, causing gear 5085 to rotate at the same rate. Rotation of gear 5085 maintains a pre-defined amount of slack in the exposed portion of drive belt 5012 as described above.

Figure 19B:
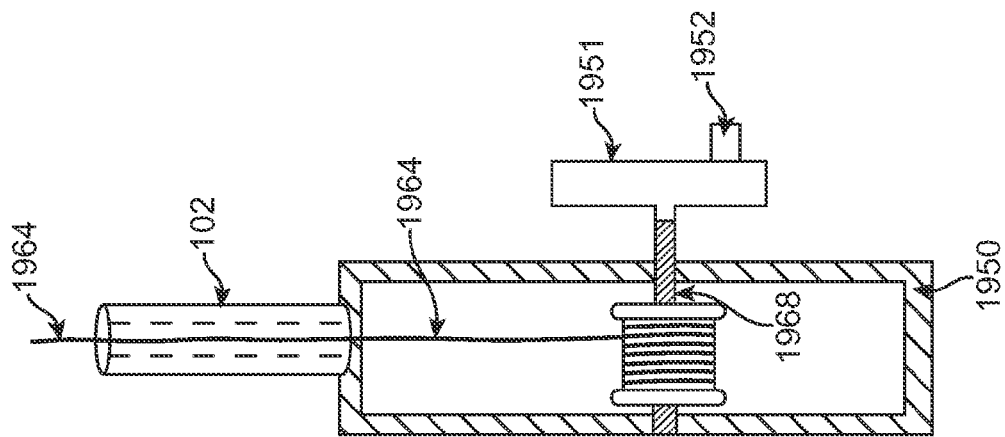
FIG. 19B is another sectional view of the proximal portion of an obstruction removal system illustrated in FIG. 19A.
Figure 19A:
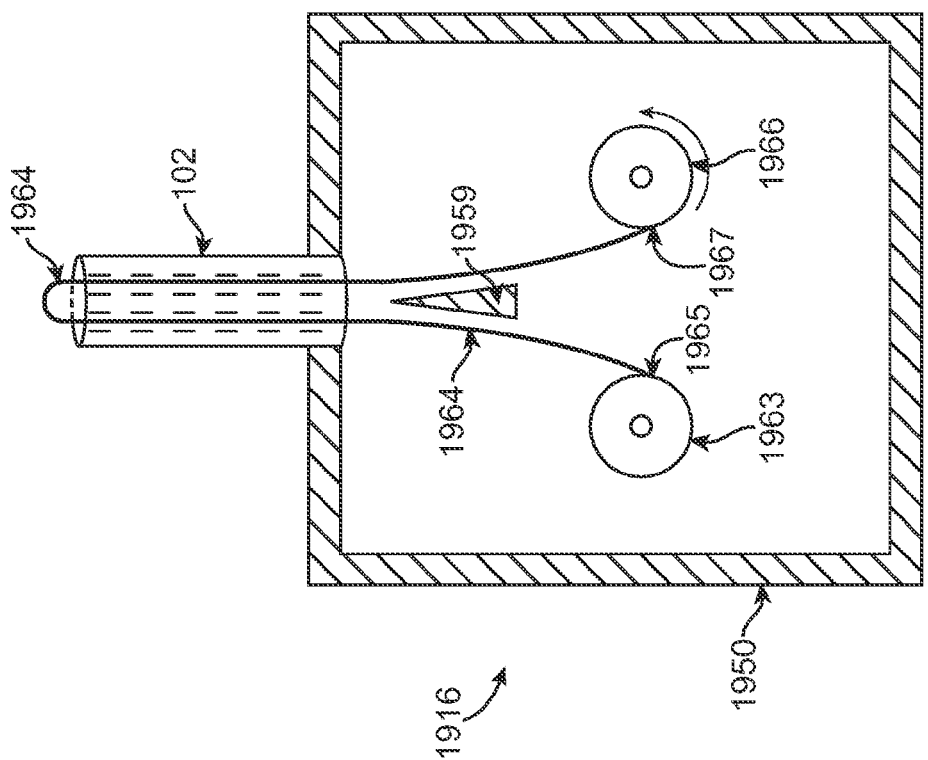
FIG. 19A is a sectional view of a proximal portion of an obstruction removal system in accordance with another embodiment of the present invention.

Another embodiment of the present invention is illustrated in FIGS. 19A-19B in which a wire and capture devices thereon do not operate in circulating manner. In the embodiment shown in FIGS. 19A-19B, drive mechanism 1916 for passing a linear band 1964 through catheter shaft 102 is a dual-spool arrangement. The dual-spool arrangement may be located within a housing 1950 located at the proximal end of catheter shaft 102. Housing 1950 also houses a guide or divider 1959 which guides band 1964 from catheter shaft 102 to the dual-spool arrangement. The dual-spool arrangement includes a first spool 1963 and a second spool 1966. A first end 1965 of band 1964 is attached to first spool 1963, and a second end 1967 of band 1964 is attached to second spool 1966. Band 1964 is wrapped around first spool 1963 prior to usage such that there is no slack in band 1964 when it is located through the lumens of catheter shaft 102. A knob 1951 having handle 1952 thereon is located outside housing 1950 such that an operator may manually control the dual-spool arrangement. Knob 1951 is joined to a connector shaft 1968 extending from second spool 1966. When an operator turns knob 1951 in a first direction via handle 1952, second spool 1966 also turns in the first direction since second spool 1966 is connected to knob 1951 via connector shaft 1968. By turning knob 1951, second spool 1966 causes band 1964 to be advanced through catheter shaft 102. Band 1964 is collected or gathered around second spool 1966 as band 1964 is run through catheter shaft 102. In this embodiment, the captured clot particles do not have to be removed from band 1964 and the capture devices located thereon since band 1964 operates in a non-circulating manner. However, if desired, a vacuum or fluid may be used to clean the captured clot particles from band 1964 and the capture devices as they are wound onto second spool 1966. The embodiment illustrated in FIGS. 19A-19B is preferably utilized when drive belt 112 and the plurality of capture devices 114 is an integral or one-piece conveyor or circulating element having integral curly, protuberant, or coiled sections formed by a wire element that also comprises the drive belt as described above in relation to FIGS. 12-15. In addition, the embodiment illustrated in FIGS. 19A-19B may also be utilized with interference devices fixed to the drive belt as described above in relation to FIGS. 11, 32, and 35-57. These embodiments of capture devices are preferred since other three-dimensional designs for the capture devices may get tangled together and make the dual-spool arrangement nonfunctional.

Cleaning Mechanisms

Figure 46:
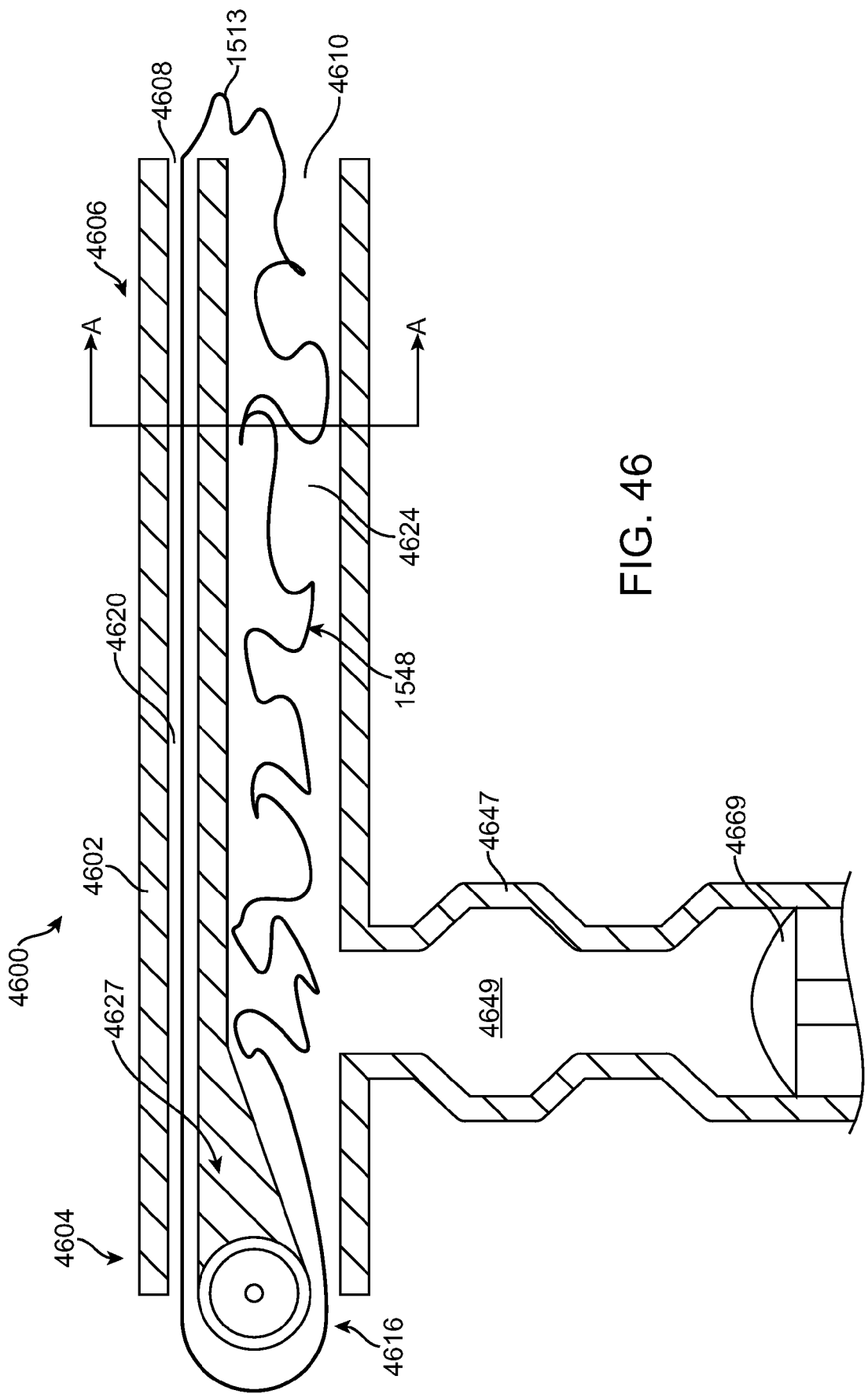
FIG. 46 is a sectional view of an obstruction removal system in accordance with another embodiment of the present invention.

Since the drive belt and the capture devices located thereon are driven through the catheter shaft in a circulating manner, the obstruction removal system also includes one or more means of removing captured clot particles from the capture devices so that the captured clot particles do not clog the obstruction removal system. In one embodiment of the present invention shown in FIG. 46, a vacuum shaft 4647 forming a clot particle reservoir 4649 therein is provided at proximal portion 4604 of catheter shaft 4602. FIG. 46 is a sectional view of an obstruction removal system 4600 in accordance with another embodiment of the present invention. Similar to the embodiment depicted in FIGS. 15-16, integral conveyor or circulating element 1513 is a wire element with a plurality of capture devices comprised of integral random protuberant sections 1548 formed therein. Integral conveyor or circulating element 1513 is formed of a material having superelastic or shape memory characteristics as described above. The superelastic or shape memory characteristics enable conveyor or circulating element 1513 to travel in a deformed, straightened state within a first lumen 4620 of catheter shaft 4602. When conveyor or circulating element 1513 exits distal end 4606 of catheter shaft 4602 via a distal exit port 4608, protuberant capture devices 1548 may assume their "remembered" deployed or expanded configuration. Upon re-entry into catheter shaft 4602 via a distal reentry port 4610, conveyor or circulating element 1513 remains in its protuberant configuration as it travels through second lumen 4624 so that the captured clot particles are retained in capture devices 1548. In order to ensure that loose clot particles do not migrate downstream, aspiration of second lumen 4624 is provided via a vacuum source 4669 provided at the end of vacuum shaft 4647. Vacuum source 4669 provides a suction force along second lumen 4624 for pulling the captured clot particles proximally into clot particle reservoir 4649. Clot particle reservoir 4649 is in fluid communication with second lumen 4624 of catheter shaft 4602. As such, vacuum source 4669 keeps second lumen 4624 free from clot particles that may dislodge during the circulation of conveyor or circulating element 1513 through second lumen 4624, thus keeping second lumen 4624 clear of debris or self-cleaning. Further, vacuum source 4669 creates a negative pressure at the distal reentry port 4610 of second lumen 4624 and thus may pull clot material towards conveyor or circulating element 1513 thus facilitating the retrieval of a small portion of the clot or obstruction in order to remove the source of vascular occlusion in a bit-by-bit or piecemeal fashion. Vacuum source 4669 may be any system capable of providing a negative pressure or suction force, including for example a syringe. At proximal portion 4604 of catheter shaft 4602, catheter shaft 4602 includes a transition section 4627 for transitioning conveyor or circulating element 1513 from second lumen 4624 into a drive mechanism 4616. Transition section 4627 has a tapered shape in order to funnel conveyor or circulating element 1513 from second lumen 4624 into drive mechanism 4616. Although FIG. 46 has been described utilizing conveyor or circulating element 1513 with integral random protuberant or curly sections 1548 formed therein, it will be apparent to those skilled in the art that the vacuum shaft and resulting aspiration may be utilized with any embodiment described herein.

In another embodiment, a vacuum and/or fluid may be utilized to clean captured clot particles from the drive belt and the capture devices located thereon as they pass through the proximal end of the obstruction removal system. A vacuum or aspirator that employs a suction force may be applied at the proximal end of the obstruction removal system in order to clean the captured clot particles from the drive belt and the capture devices as they pass through the drive mechanism. Further, a fluid under pressure may be applied at the proximal end of the obstruction removal system in order to clean the captured clot particles from the drive belt and the capture devices as they pass through the drive mechanism.

Figure 30:
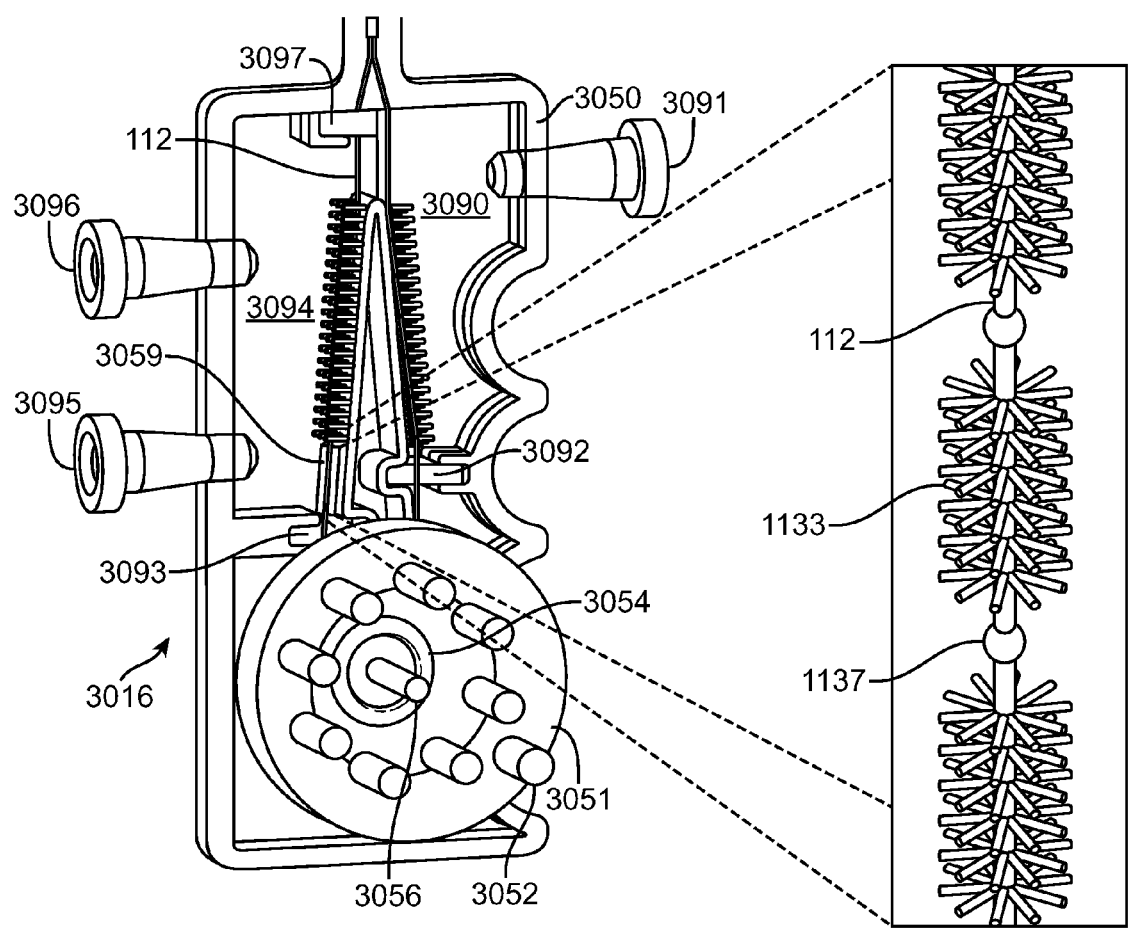
FIG. 30 is a perspective view of a proximal portion of an obstruction removal system in accordance with an embodiment of the present invention.

More particularly, as illustrated in FIG. 30, the drive mechanism may be a mechanical pulley system manually operated by the device operator which advances drive belt 112 and the capture devices located thereon through catheter shaft 102 in a circulating manner. In the embodiment depicted in FIG. 30, the capture devices are hairbrush-like interference devices 1133 described above with respect to FIG. 11. Drive mechanism 3016 is a pulley system located within a housing 3050 located at proximal end 104 of catheter shaft 102. Housing 3050 also houses a guide or divider 3059 which guides drive belt 112 from catheter shaft 102 through a vacuum chamber 3090 to a pulley 3054, and through a rinse chamber 3094. A knob 3051 having a handle 3052 thereon is located outside housing 3050 such that an operator may manually control the pulley system. Knob 3051 has a centrally located hole (not shown) which receives and is joined to a connector shaft 3056 extending from pulley 3054. When an operator turns knob 3051 in a first direction via handle 3052, pulley 3054 also turns in the same direction since pulley 3054 is fixedly connected to knob 3051 via connector shaft 3056. By turning knob 3051, pulley 3054 thus drives drive belt 112 and the hairbrush-like interference devices 1133 located thereon through catheter shaft 102 in a circulating manner. The hairbrush-like interference devices 1133 are pulled through the second lumen of catheter 102 and passes the guide or divider 3059 in the vacuum chamber 3090, dislodging the clot particles off the hairbrush-like interference devices 1133 into the vacuum chamber 3090. The hairbrush-like interference devices 1133 then pass through a first one-way valve 3092 and around pulley 3054. Protrusions 1137 located on drive belt 112 between the hairbrush-like interference devices 113 engage pulley 3054 and thus pull drive belt 112 at a constant speed. The hairbrush-like interference devices 1133 then pass through a second one-way valve 3093 in order to enter rinsing chamber 3094. The hairbrush-like interference devices 1133 pass over or through guide or divider 3059 while in rinsing chamber 3094 and then pass through a third one-way valve 3097 in order to enter catheter shaft 102.

Vacuum chamber 3090 contains a connector or port 3091 for connection to a vacuum source (not shown). The vacuum source creates a vacuum in the vacuum chamber 3090 and in the second lumen of catheter 102. The negative pressure or vacuum keeps the second lumen free from clot particles that may dislodge during the circulation of obstruction removal system 100, thus keeping the second lumen clear of debris or self-cleaning. First one-way valve 3092 maintains the vacuum in the vacuum chamber 3090.

Rinse chamber 3094 contains a first connector or port 3095 and a second connector or port 3096 for circulating a rinsing fluid. First connector 3095 is the fluid entry port and second connector 3096 is the fluid exit port. However, one of ordinary skill in the art will recognize that the connectors may be interchanged such that first connector 3095 is the fluid exit port and second connector 3096 is the fluid entry port. The hairbrush-like interference devices 1133 pass over or through the guide or divider 3059 in the rinsing chamber 3094 in order to ensure that the captured clot particles are removed from the hairbrush-like interference devices 1133 before the capture devices are re-circulated through catheter shaft 102. Drive belt 112 enters catheter shaft 102 through third one-way valve 3097 and into the first lumen of catheter shaft 102. One-way valves 3093 and 3097 prevent the fluid from exiting rinsing chamber 3094, except through fluid entry port 3095 and fluid exit port 3096.

Another embodiment of a drive mechanism 1716 for removing captured clot particles from the capture devices is shown in FIGS. 17A-17B. Drive mechanism 1716 includes a second collinear pulley 1757 that is provided to squeegee captured clot particles from the capture devices (not shown). First pulley 1754 includes protrusions or teeth 1755 and second pulley 1757 includes mating protrusions or teeth 1758. Teeth 1755 of first pulley 1754 are of such form, size, and spacing that they mesh with teeth 1758 of second pulley 1757.

In other words, first pulley 1754 and second pulley 1757 cooperate similar to two mating gears. Teeth 1755 and 1758 of first and second pulleys 1754 and 1757, respectively, mesh together at an intersection 1760. Teeth 1755 of first pulley 1754 mesh with teeth 1758 of second pulley 1757 in order to drive second pulley 1758 in an opposite direction. Otherwise stated, when first pulley 1754 is turned in a first direction via manually operated knob 1751, such turning causes second pulley 1757 to turn in a separate opposite direction. For example, if an operator turns knob 1751 and consequently first pulley 1754 in a clockwise direction, second pulley 1757 will turn in a counter clockwise direction. Further, teeth 1755 of first pulley 1754 prevent slippage of second pulley 1757. As drive belt 112 and the capture devices located thereon pass through intersection 1760, the captured clot particles located within the capture devices are pushed or squeezed off drive belt 112 and into housing 1750. Additional cleaning mechanisms, such as a vacuum and/or fluid described above, may also be used to clean the captured clot particles from drive belt 112 and the capture devices as they pass through the pulley system.

Another embodiment for removing captured clot particles from the capture devices is shown in FIGS. 18A-18B. Drive mechanism 1816 is a single pulley system. A single pulley 1854 functions similar to first pulley 1754. A guide or divider 1859 guides drive belt 112 from catheter shaft 102 to first pulley 1854. However, rather than a second collinear pulley, drive mechanism 1816 includes a brush 1861 that removes the captured clot from the capture devices prior to reaching single pulley 1854. Brush 1861 includes a plurality of bristles 1862 that are attached to the outside surface of divider 1859. Bristles 1862 extend from divider 1859 and may be formed of any suitable material, including but not limited to PEBAX, nylon, polyimide, PEEK, polyethylene terephalate (PET) polyurethane, polyethylene, polypropylene, stainless steel, nickel titanium, MP35N, and tantalum. As drive belt 112 and the capture devices located thereon pass over brush 1861, the captured clot particles located within the capture devices are ensnared or caught in bristles 1862. Additional cleaning mechanisms, such as a vacuum and/or fluid described above, may also be used to clean the captured clot particles from drive belt 112 and the capture devices as they pass through the single pulley system.

Additional Embodiments

Figure 52:
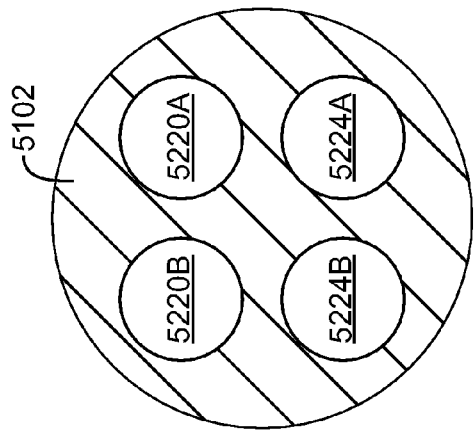
FIG. 52 is a cross-sectional view of the catheter shaft of the obstruction removal system of FIG. 51.
Figure 51:
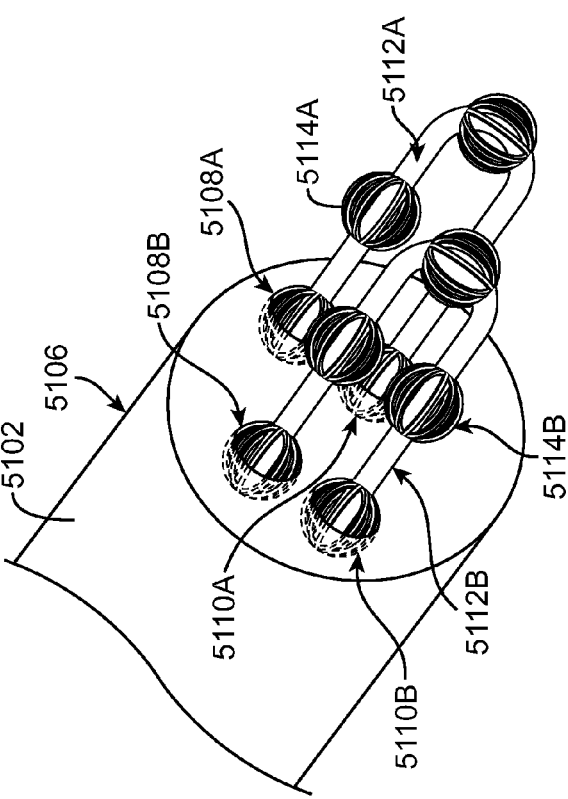
FIG. 51 is a perspective view of a distal portion of an obstruction removal system having two drive belts in accordance with an embodiment of the present invention.
Figure 54:
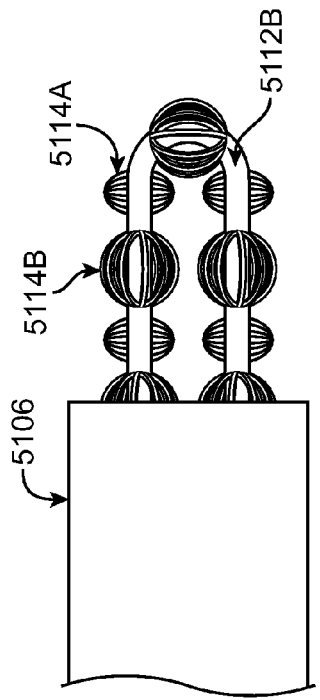
FIG. 54 is a side view of the distal portion of the obstruction removal system of FIG. 51 in accordance with another embodiment of the present invention.
Figure 53:
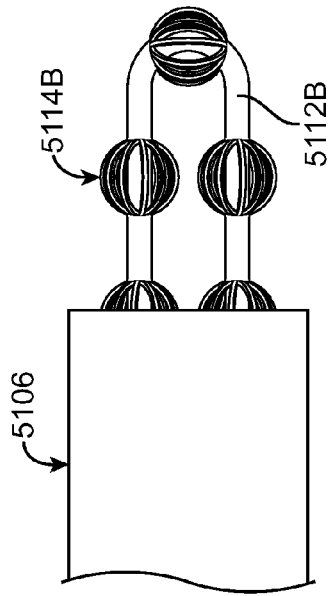
FIG. 53 is a side view of the distal portion of the obstruction removal system of FIG. 51 in accordance with an embodiment of the present invention.

Embodiments of the present invention have been described herein as including a single drive belt for carrying a plurality of capture devices in a circulating manner through an obstruction removal system. However, more than one drive belt having a plurality of capture devices thereon may be used to capture an obstruction. For example, FIG. 51 is a perspective view of a distal portion 5106 of a catheter shaft 5102. FIG. 52 is a cross-sectional view of catheter shaft 5102, wherein the drive belts and capture devices have not been shown for clarity. Catheter shaft 5102 has four parallel lumens extending there through for circulating two drive belts, first drive belt 5112A and a second drive belt 5112B, in a circulating manner through the obstruction removal system. First drive belt 5112A carrying capture devices 5114A extend through a first lumen 5220A of catheter shaft 5102, exit catheter shaft 5102 via distal exit port 5108A, pass through a clot or obstruction while retrieving small particles of the obstruction, pull the captured clot particles through distal reentry port 5110A, and extend through a second lumen 5224A of catheter shaft 5102. Similarly, second drive belt 5112B carrying capture devices 5114B extend through a first lumen 5220B of catheter shaft 5102, exit catheter shaft 5102 via distal exit port 5108B, pass through a clot or obstruction while retrieving small particles of the obstruction, pull the captured clot particles through distal reentry port 5110B, and extend through a second lumen 5224B of catheter shaft 5102. Utilizing multiple drive belts increase the number of capture devices passing through the clot or obstruction, and thus may assist in removing the entire mass of the clot or obstruction in a relatively shorter time. In addition, the multiple drive belts and capture devices are parallel to each other and thus will evenly remove the side portions of the clot or obstruction. Capture devices 5114A of first drive belt 5112A may encounter the clot or obstruction at the same time as capture devices 5114B of second drive belt 5112B, as shown in the side view of distal catheter portion 5106 in FIG. 53. Alternatively, as shown in FIG. 54, capture devices 5114A of first drive belt 5112A may alternate with capture devices 5114B of second drive belt 5112B, such that the capture devices do not encounter the clot or obstruction at the same time.

Figure 56:
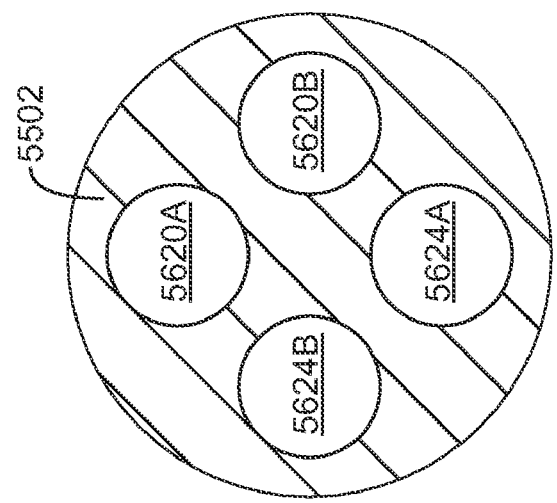
FIG. 56 is a cross-sectional view of the catheter shaft of the obstruction removal system of FIG. 55.
Figure 55:
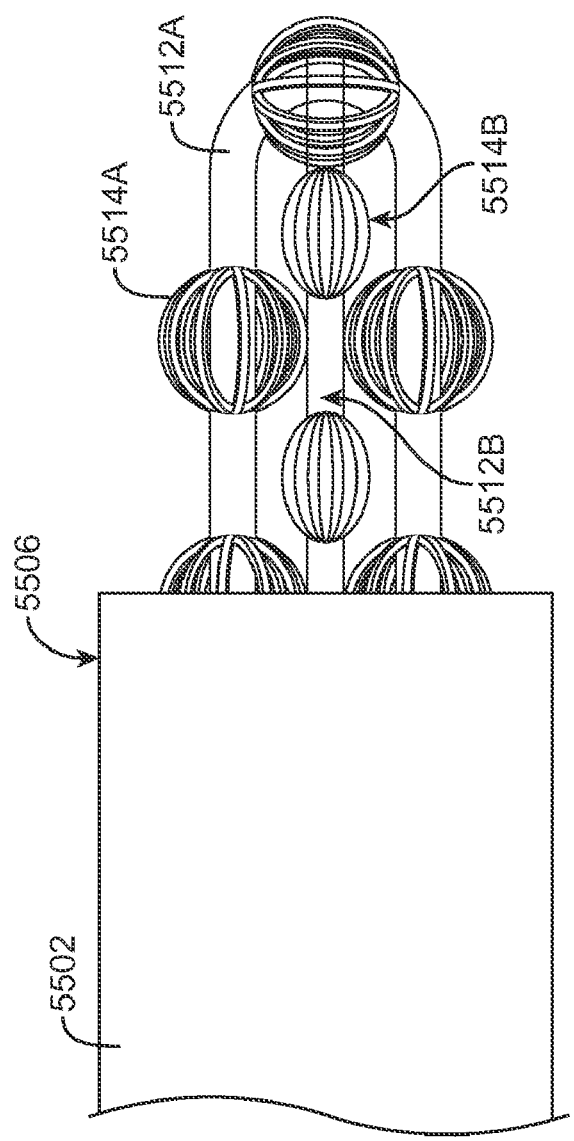
FIG. 55 is a perspective view of a distal portion of an obstruction removal system having two drive belts in accordance with another embodiment of the present invention.

Another embodiment of the present invention including more than one drive belt with a plurality of capture devices thereon is illustrated in FIGS. 55-56. FIG. 55 is a side view of a distal portion 5506 of a catheter shaft 5502. FIG. 56 is a cross-sectional view of catheter shaft 5502, wherein the drive belts and capture devices have not been shown for clarity. Catheter shaft 5502 has four parallel lumens extending there through for circulating two drive belts, first drive belt 5512A and a second drive belt 5512B, in a circulating manner through the obstruction removal system. Rather than extending parallel to each other as shown in the embodiment of FIGS. 51-54, drive belts 5512A and 5512B exit the distal portion 5506 in a crossing or overlapping pattern. For example, first drive belt 5512A is shown as extending over a "vertical" path when it exits catheter shaft 5502 while second drive belt 5512B is shown as extending over a "horizontal" path when it exits catheter shaft 5502. First drive belt 5512A carrying capture devices 5514A extend through a first lumen 5620A of catheter shaft 5502, exit catheter shaft 5502 via a distal exit port (not shown), pass through a clot or obstruction while retrieving small particles of the obstruction, pull the captured clot particles through a distal reentry port (not shown), and extend through a second lumen 5624A of catheter shaft 5502. Similarly, second drive belt 5512B carrying capture devices 5514B extend through a first lumen 5620B of catheter shaft 5502, exit catheter shaft 5502 via a distal exit port (not shown), pass through a clot or obstruction while retrieving small particles of the obstruction, pull the captured clot particles through a distal reentry port (not shown), and extend through a second lumen 5624B of catheter shaft 5502. In this embodiment, the multiple drive belts and capture devices are perpendicular to each other and thus will evenly remove the clot or obstruction.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method for removing an obstruction within a body lumen, the method comprising the steps of:
   tracking an obstruction removal system through the body lumen to the obstruction over an indwelling guidewire, wherein the obstruction removal system includes a catheter shaft having a proximal end and a distal end, the catheter shaft defining a first lumen having a distal exit port and a second lumen having a distal reentry port and a third lumen extending along at least a distal portion of the catheter shaft, wherein the first lumen and the second lumen extend side-by-side from the proximal end to the distal end of the catheter shaft, and a drive belt having a plurality of capture devices occurring along at least a portion thereof, wherein the drive belt extends through each of the first and second lumens to form a loop that extends from the proximal and distal ends of the catheter shaft and wherein the guidewire extends through the third lumen while the obstruction removal system is being tracked through the body lumen to the obstruction;
   positioning the obstruction removal system such that the distal end of the catheter shaft is near the obstruction within the body lumen;
   circulating the drive belt through the catheter shaft such that the plurality of capture devices advance through the first lumen, exit the catheter shaft through the distal exit port, travel through the obstruction distal of the catheter shaft, reenter the catheter shaft through the distal reentry port and advance through the second lumen;
   removing at least a portion of the obstruction from the body lumen in a bit-by-bit fashion as each capture device travels distal of the catheter shaft between the distal exit port and the distal reentry port of the catheter shaft; and
   removing substantially the entire obstruction from the body lumen after the plurality of capture devices are circulated through the catheter shaft in a series of passes.

2. The method of claim 1, wherein the plurality of capture devices are formed by integral sections of the drive belt.

3. The method of claim 2, wherein the drive belt is a wire constructed out of an elastic or shape memory material such that the drive belt has a first straightened configuration and a second expanded configuration forming the plurality of capture devices.

4. The method of claim 1, wherein the plurality of capture devices are a plurality of basket-like devices attached to the drive belt.

5. The method of claim 4, wherein each of the plurality of basket-like devices has a shape selected from a group consisting of a cylinder, a sphere, a bowl, an elongated oval, a crescent, and a spool having flared end portions.

6. The method of claim 1, wherein the plurality of capture devices are a plurality of interference devices attached to the drive belt, each of the plurality of interference devices selected from a group consisting of a bead-like device, a balloon-like device, and a burr-like device.

7. The method of claim 1, wherein the plurality of capture devices are a plurality of interference devices attached to the drive belt, each of the plurality of interference devices selected from a group consisting of a hairbrush-like device having radially extending bristles and a wire-brush device having looping strands.

8. The method of claim 1, wherein the step of positioning includes contacting the obstruction with the distal end of the catheter shaft.

9. The method of claim 1, wherein the step of circulating includes passing the capture devices on the drive belt through a vacuum chamber and a rinse chamber of a housing, wherein the housing is attached to the proximal end of the catheter shaft and remains external of the patient.

10. The method of claim 9, wherein the housing includes a drive mechanism that includes a pulley over which the drive belt is looped such that the step of circulating includes manually rotating the pulley.

11. A method for removing an obstruction within a body lumen, the method comprising the steps of:
    tracking an obstruction removal system through the body lumen to the obstruction over a previously placed guidewire, wherein the obstruction removal system includes
    a catheter shaft defining a first lumen having a distal exit port, a second lumen having a distal reentry port and a third lumen, wherein the first, second and third lumens extend from a proximal end to a distal end of the catheter shaft and wherein the guidewire extends through the third lumen at least while the obstruction removal system is being tracked through the body lumen to the obstruction, and
    a drive belt having a plurality of capture devices positioned along at least a portion thereof, wherein the drive belt extends through the full length of the first and second catheter shaft lumens to form an endless loop;
    positioning the obstruction removal system such that the catheter shaft distal exit port and distal entry port are positioned proximate to the obstruction within the body lumen;
    circulating the drive belt through the catheter shaft such that the plurality of capture devices advance through the first lumen, exit the catheter shaft through the distal exit port, travel through the obstruction distal of the catheter shaft, reenter the catheter shaft through the distal reentry port and advance through the second lumen;
    removing at least a portion of the obstruction from the body lumen in a bit-by-bit fashion as each capture device travels distal of the catheter shaft between the distal exit port and the distal reentry port of the catheter shaft; and
    removing substantially the entire obstruction from the body lumen after the plurality of capture devices are circulated through the catheter shaft in a series of passes.

12. The method of claim 11, wherein the step of positioning includes advancing the obstruction removal system such that the catheter shaft distal end touches the obstruction.

13. The method of claim 11, wherein the looped drive belt is coupled to a drive mechanism located within a housing attached to the catheter shaft proximal end.

14. The method of claim 13, further comprising:
    cleaning obstruction particulate from the capture devices as the capture devices circulate through the housing.

15. The method of claim 14, wherein the step of cleaning includes passing the capture devices on the drive belt through a vacuum chamber and a rinse chamber of the housing.

16. The method of claim 11, wherein the plurality of capture devices are a plurality of interference devices attached to the drive belt, each of the plurality of interference devices selected from a group consisting of a hairbrush-like device having radially extending bristles and a wire-brush device having looping strands.

* * * * *